United States Patent
Borody

(10) Patent No.: US 11,123,377 B2
(45) Date of Patent: *Sep. 21, 2021

(54) COMPOSITIONS FOR FECAL FLORAL TRANSPLANTATION AND METHODS FOR MAKING AND USING THEM AND DEVICE FOR DELIVERING THEM

(71) Applicant: Finch Therapeutics Holdings LLC, Somerville, MA (US)

(72) Inventor: Thomas J. Borody, Five Dock (AU)

(73) Assignee: Finch Therapeutics Holdings LLC, Somerville, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/180,704

(22) Filed: Nov. 5, 2018

(65) Prior Publication Data

US 2019/0134106 A1 May 9, 2019

Related U.S. Application Data

(63) Continuation of application No. 15/887,651, filed on Feb. 2, 2018, now Pat. No. 10,821,138, which is a continuation of application No. 15/155,628, filed on May 16, 2016, now Pat. No. 9,901,603.

(60) Provisional application No. 62/161,826, filed on May 14, 2015.

(51) Int. Cl.
| | |
|---|---|
| *A61K 35/74* | (2015.01) |
| *A61K 35/742* | (2015.01) |
| *A61K 9/19* | (2006.01) |
| *A61K 47/26* | (2006.01) |
| *A61K 35/747* | (2015.01) |
| *A61K 35/745* | (2015.01) |
| *A61K 47/10* | (2017.01) |
| *A61K 9/48* | (2006.01) |

(52) U.S. Cl.
CPC ........... *A61K 35/74* (2013.01); *A61K 9/19* (2013.01); *A61K 9/4858* (2013.01); *A61K 35/742* (2013.01); *A61K 35/745* (2013.01); *A61K 35/747* (2013.01); *A61K 47/10* (2013.01); *A61K 47/26* (2013.01)

(58) Field of Classification Search
None
See application file for complete search history.

(56) References Cited

U.S. PATENT DOCUMENTS

| | | |
|---|---|---|
| 3,192,116 A | 6/1965 | Möse et al. |
| 3,320,130 A | 5/1967 | Henry |
| 3,713,836 A | 1/1973 | Carlsson |
| 4,098,728 A | 7/1978 | Rosenblatt |
| 4,332,790 A | 6/1982 | Sozzi et al. |
| 4,335,107 A | 6/1982 | Snoeyenbos et al. |
| 4,452,779 A | 6/1984 | Cockerill |
| 4,536,409 A | 8/1985 | Farrell et al. |
| 4,657,762 A | 4/1987 | Mikkola et al. |
| 4,710,379 A | 12/1987 | Kawai et al. |
| 4,892,731 A | 1/1990 | Arai et al. |
| 4,975,286 A | 12/1990 | Hechter |
| 5,213,807 A | 5/1993 | Chemburkar et al. |
| 5,266,315 A | 11/1993 | Taguchi et al. |
| 5,443,826 A | 8/1995 | Borody |
| 5,599,795 A | 2/1997 | McCann et al. |
| 5,728,380 A | 3/1998 | Allen et al. |
| 5,800,821 A | 9/1998 | Acheson et al. |
| 5,837,238 A | 11/1998 | Casas et al. |
| 5,858,356 A | 1/1999 | Wolf et al. |
| 5,902,578 A | 5/1999 | Halpin-Dohnalek et al. |
| 5,902,743 A | 5/1999 | Luchansky et al. |
| 6,087,386 A | 7/2000 | Chen et al. |
| 6,162,464 A | 12/2000 | Jacob et al. |
| 6,245,740 B1 | 6/2001 | Goldenberg et al. |
| 6,284,274 B1 | 9/2001 | Merrill et al. |
| 6,428,783 B1 | 8/2002 | Khachatrian et al. |
| 6,514,531 B1 | 2/2003 | Alaux et al. |
| 6,645,530 B1 | 11/2003 | Borody |
| 6,649,397 B1 | 11/2003 | Nakamura |
| 6,756,032 B1 | 6/2004 | Tepper et al. |
| 6,926,907 B2 | 8/2005 | Plachetka |
| 6,979,674 B1 | 12/2005 | Goldenberg et al. |

(Continued)

FOREIGN PATENT DOCUMENTS

| | | |
|---|---|---|
| AU | 2001276160 B2 | 6/2007 |
| CA | 1333564 | 12/1994 |

(Continued)

OTHER PUBLICATIONS

Strasser et al., "Influence of lyophilization, fluidized bed drying, addition of protectants, and storage on the viability of lactic acid bacteria", Journal of Applied Microbiology, vol. 107, pp. 167-177 (Year: 2009).*

(Continued)

*Primary Examiner* — Michelle F. Paguio Frising

(74) *Attorney, Agent, or Firm* — Arnold & Porter Kaye Scholer LLP; David Marsh; Scott Douglas

(57) ABSTRACT

This application provides compositions, e.g., formulations, used for gastric, gastrointestinal and/or colonic treatments, and methods for making, storing and using them, including storage, including long term storage, at room temperature. Compositions provided herein are useful for treating various diseases or conditions such as autism spectrum disorder, Crohn's Disease, ulcerative colitis, irritable bowel syndrome, and recurrent or primary *C. difficile* infection.

41 Claims, 8 Drawing Sheets

(56) References Cited

U.S. PATENT DOCUMENTS

| | | |
|---|---|---|
| 6,984,513 B2 | 1/2006 | Brown et al. |
| 7,018,629 B2 | 3/2006 | Jacob et al. |
| 7,374,753 B1 | 5/2008 | Farmer et al. |
| 7,541,091 B2 | 6/2009 | Sisson et al. |
| 7,749,509 B2 | 7/2010 | Cobb et al. |
| 7,763,276 B1 | 7/2010 | Shodai et al. |
| 7,799,341 B2 | 9/2010 | Porzio et al. |
| 7,815,956 B2 | 10/2010 | Lee et al. |
| 7,846,475 B2 | 12/2010 | Shiraishi et al. |
| 7,888,062 B1 | 2/2011 | Garner et al. |
| 7,998,510 B2 | 8/2011 | Caswell |
| 8,168,171 B2 | 5/2012 | Mogna et al. |
| 8,460,648 B2 | 6/2013 | Borody |
| 8,637,297 B2 | 1/2014 | Fernandez et al. |
| 8,658,153 B2 | 2/2014 | Daube et al. |
| 8,771,673 B2 | 7/2014 | Cobb et al. |
| 9,040,036 B2 | 5/2015 | Borody |
| 9,050,538 B2 | 6/2015 | Borody |
| 9,308,226 B2 | 4/2016 | Borody |
| 9,320,763 B2 | 4/2016 | Borody |
| 9,408,872 B2 | 8/2016 | Borody |
| 9,468,658 B2 | 10/2016 | Borody |
| 9,572,841 B2 | 2/2017 | Borody |
| 9,572,842 B2 | 2/2017 | Borody |
| 9,610,308 B2 | 4/2017 | Borody |
| 9,623,056 B2 | 4/2017 | Borody |
| 2001/0014322 A1 | 8/2001 | Chen et al. |
| 2002/0013270 A1 | 1/2002 | Bolte |
| 2002/0022019 A1 | 2/2002 | Laulund |
| 2002/0039599 A1 | 4/2002 | Lin et al. |
| 2003/0092163 A1 | 5/2003 | Collins et al. |
| 2003/0092724 A1 | 5/2003 | Kao et al. |
| 2003/0147858 A1 | 8/2003 | Renaud et al. |
| 2004/0062757 A1 | 4/2004 | Finegold |
| 2004/0167062 A1 | 8/2004 | Bolte |
| 2004/0170617 A1 | 9/2004 | Finegold |
| 2004/0223956 A1 | 11/2004 | Naidu et al. |
| 2006/0076536 A1 | 4/2006 | Barshied |
| 2006/0099197 A1 | 5/2006 | Farmer |
| 2006/0115465 A1 | 6/2006 | Macfarlane et al. |
| 2006/0275223 A1 | 12/2006 | Burr |
| 2007/0059296 A1 | 3/2007 | Chen |
| 2008/0254009 A1 | 10/2008 | Finegold |
| 2008/0299197 A1 | 12/2008 | Toneguzzo et al. |
| 2010/0112003 A1 | 5/2010 | Collins et al. |
| 2010/0178349 A1 | 7/2010 | Kolter et al. |
| 2010/0178413 A1 | 7/2010 | Gorris |
| 2010/0184785 A1 | 7/2010 | Kolter et al. |
| 2010/0222311 A1 | 9/2010 | Thommes et al. |
| 2010/0226866 A1 | 9/2010 | Yamashiro et al. |
| 2010/0233278 A1 | 9/2010 | Ookawa et al. |
| 2010/0239667 A1 | 9/2010 | Hemmingsen et al. |
| 2010/0247489 A1 | 9/2010 | Saur-Brosch et al. |
| 2010/0247665 A1 | 9/2010 | Takahashi |
| 2010/0255231 A1 | 10/2010 | Chau et al. |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0289164 A1 | 11/2010 | Porzio et al. |
| 2010/0297031 A1 | 11/2010 | Ubeda Perez et al. |
| 2011/0008554 A1 | 1/2011 | Chen et al. |
| 2011/0045222 A1 | 2/2011 | Peters |
| 2011/0081320 A1 | 4/2011 | Westall et al. |
| 2011/0200570 A1 | 8/2011 | Mosbaugh et al. |
| 2011/0218216 A1 | 9/2011 | Vivek et al. |
| 2012/0039853 A1 | 2/2012 | Corveleyn et al. |
| 2012/0064133 A1 | 3/2012 | Chauhan et al. |
| 2012/0087895 A1 | 4/2012 | Mazmanian et al. |
| 2012/0183612 A1 | 7/2012 | Brogmann et al. |
| 2012/0252775 A1 | 10/2012 | Finegold |
| 2013/0045274 A1 | 2/2013 | Hlavka |
| 2013/0195804 A1 | 8/2013 | Borody |
| 2013/0259899 A1 | 10/2013 | Allen-Vercoe et al. |
| 2013/0316394 A1 | 11/2013 | Stimpson |
| 2014/0065132 A1 | 3/2014 | Hsiao et al. |
| 2014/0086877 A1 | 3/2014 | Hlavka |
| 2014/0147417 A1 | 5/2014 | Sadowsky et al. |
| 2014/0234260 A1 | 8/2014 | Borody |
| 2014/0255351 A1 | 9/2014 | Berstad et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2014/0363397 A1 | 11/2014 | Allen-Vercoe et al. |
| 2015/0050246 A1 | 2/2015 | Jones et al. |
| 2015/0093360 A1 | 4/2015 | McKenzie et al. |
| 2015/0143557 A1 | 5/2015 | Honda et al. |
| 2015/0152484 A1 | 6/2015 | Krajmalnik-Brown et al. |
| 2015/0190435 A1 | 7/2015 | Henn et al. |
| 2015/0224152 A1 | 8/2015 | Littman et al. |
| 2015/0238545 A1 | 8/2015 | Borody |
| 2015/0238546 A1 | 8/2015 | Borody |
| 2015/0297642 A1 | 10/2015 | Borody |
| 2015/0306144 A1 | 10/2015 | Borody |
| 2015/0306155 A1 | 10/2015 | Borody |
| 2015/0306156 A1 | 10/2015 | Borody |
| 2015/0374761 A1 | 12/2015 | Sadowsky et al. |
| 2016/0089363 A1 | 3/2016 | Borody |
| 2016/0151429 A1 | 6/2016 | Borody |
| 2016/0151431 A1 | 6/2016 | Borody |
| 2016/0151432 A1 | 6/2016 | Borody |
| 2016/0151433 A1 | 6/2016 | Borody |
| 2016/0279178 A1 | 9/2016 | Borody |
| 2016/0279179 A1 | 9/2016 | Borody |

FOREIGN PATENT DOCUMENTS

| | | |
|---|---|---|
| CA | 2 391 422 A1 | 1/2004 |
| CN | 1561387 A | 1/2005 |
| CN | 201441672 U | 4/2010 |
| DE | 2 134 179 A1 | 1/1973 |
| EP | 0 303 426 A2 | 2/1989 |
| EP | 0 456 418 A2 | 11/1991 |
| EP | 0 433 299 B1 | 5/1998 |
| EP | 1 514 572 A2 | 3/2005 |
| EP | 1 800 688 A1 | 6/2007 |
| EP | 1 514 572 B1 | 12/2008 |
| FR | 1275 M | 5/1962 |
| FR | 2427 M | 3/1964 |
| FR | 2828 M | 10/1964 |
| FR | 5528 M | 11/1967 |
| FR | 2 244 464 A1 | 4/1975 |
| GB | 1 271 674 A | 4/1972 |
| JP | 64-67192 | 3/1989 |
| JP | H05-306221 A | 11/1993 |
| JP | H07-242539 A | 9/1995 |
| JP | H07-242557 A | 9/1995 |
| JP | 3 144 556 B2 | 3/2001 |
| JP | 2004-501095 | 1/2004 |
| JP | 2005-118544 A | 5/2005 |
| JP | 2008-106066 | 5/2008 |
| JP | 2010-513359 | 4/2010 |
| JP | 2010-520234 A | 6/2010 |
| JP | 2014/507481 | 3/2014 |
| WO | WO 90/01335 A1 | 2/1990 |
| WO | WO 95/33046 A1 | 12/1995 |
| WO | WO 96/11014 A1 | 4/1996 |
| WO | WO 98/13068 A1 | 4/1998 |
| WO | WO 00/07571 A2 | 2/2000 |
| WO | WO 00/015760 | 3/2000 |
| WO | WO 00/42168 A2 | 7/2000 |
| WO | WO 02/07741 A1 | 1/2002 |
| WO | WO 03/033681 A2 | 4/2003 |
| WO | WO 2005/017095 A2 | 2/2005 |
| WO | WO 2006/127355 A2 | 11/2006 |
| WO | WO 2008/077614 A2 | 7/2008 |
| WO | WO 2008/105715 A2 | 9/2008 |
| WO | WO 2008/117266 A2 | 10/2008 |
| WO | WO 2008/117267 A2 | 10/2008 |
| WO | WO 2008/077614 A3 | 1/2009 |
| WO | WO 2009/026306 A2 | 2/2009 |
| WO | WO 2009/055362 A1 | 4/2009 |
| WO | WO 2010/040020 A1 | 4/2010 |
| WO | WO 2011/033310 A1 | 3/2011 |
| WO | WO 2011/094027 A1 | 8/2011 |

(56) References Cited

FOREIGN PATENT DOCUMENTS

| | | | |
|---|---|---|---|
| WO | WO 2011/110347 A2 | 9/2011 | |
| WO | WO 2011/151941 A1 | 12/2011 | |
| WO | WO 2011/152566 A2 | 12/2011 | |
| WO | WO 2012/016287 A2 | 2/2012 | |
| WO | WO 2012/045150 A1 | 4/2012 | |
| WO | WO 2012/122478 A1 | 9/2012 | |
| WO | WO 2012/016287 A3 | 11/2012 | |
| WO | WO 2013/037067 A1 | 3/2013 | |
| WO | WO 2013/090825 A1 | 6/2013 | |
| WO | WO 2014/121302 | 2/2014 | |
| WO | WO 2014/078911 A1 | 5/2014 | |
| WO | WO-2014121298 A2 * | 8/2014 | ............... A61K 9/48 |
| WO | WO 2014/152338 A1 | 9/2014 | |
| WO | WO 2014/152484 A1 | 9/2014 | |
| WO | WO 2015/006355 A2 | 1/2015 | |
| WO | WO 2015/051323 A1 | 4/2015 | |
| WO | WO 2015/077794 A1 | 5/2015 | |
| WO | WO 2015/095241 A2 | 6/2015 | |

OTHER PUBLICATIONS

Celik et al., "Factors influencing the stability of freeze-dried stress-resilient and stress-sensitive strains of bifidobacteria", Journal of Dairy Science, vol. 96, pp. 3506-3516 (Year: 2013).*
"ARGF—'Autologous Rehabilitation of Gastrointestinal Flora,'" Medipex Report for Medilink NW, pp. 1-42, n.d., Web, Feb. 10, 2012 <http://www.bacteriotherapy.org/docs/medipex-report.pdf>
"Frequently Asked Questions about Clostridium difficile for Healthcare Providers," Healthcare-associated Infections (HAIs), Centers for Disease Control and Prevention, pp. 1-6, Nov. 25, 2010, updated Mar. 6, 2012, Web, May 19, 2014 <http://www.cdc.gov/HAI/organisms/cdiff/Cdiff_faqs_HCP.html>.
"Monilia," Def 1, *Stedman's Medical Dictionary*, n.d., Web, Nov. 22, 2005.
"Probiotic," Def 1, *MSN Encarta—Dictionary*, Encarta, n.d., Web, Dec. 1, 2005.
Aas et al., "Recurrent Clostridium difficile Colitis: Case Series Involving 18 Patients Treated with Donor Stool Administered via a Nasogastric Tube," *Clinical Infectious in Diseases*, 36(5):580-585 (2003).
Acha et al.," Changes of viability and composition of the *Escherichia coli* flora in faecal samples during long time storage," *Journal of Microbiological Methods*, Elsevier, 63(3):229-238 (2005).
Agrawal et al., "'Global warming' to *Mycobacterium avium* subspecies paratuberculosis," *Future Microbiol*, 9(7):829-832 (2014).
Agrawal et al., "A Long-Term Follow-Up Study of the Efficacy and Safety of Fecal Microbiota Transplant (FMT) for Recurrent/Severe/Complicated *C. difficile* Infection (CDI) in the Elderly," *Gastroenterol*, 146(5)(Suppl 1):S42-43 (2014).
Aitken et al., "Demonstration of Intracellular *Mycobacterium* Species in Crohn's Disease Using Novel Technologies," Poster Presentation—2015 ACG Annual Scientific Meeting, Honolulu, Hawaii, USA (2015).
Akao et al., "A Purgative Action of Barbaloin Is Induced by *Eubacterium* sp. Strain BAR, a Human Intestinal Anaerobe, Capable of Transforming Barbaloin to Aloe-Emodin Anthrone," *Biol. Pharm.*, 19(1):136-138 (1996).
Al-Eidan et al., "Clostridium difficile-associated diarrhoea in hospitalised patients," *J. Clin. Pharm. Ther.*, 25(2):101-109 (2000).
Al-Nassir et al., "Comparison of Clinical and Microbiological Response to Treatment of Clostridium difficile-Associated Disease with Metronidazole and Vancomycin," *Clin Infect Dis.*, 47(1):56-62 (2008).
Anand et al., "Epidemiology, clinical manifestations, and outcome of Clostridium difficile-associated diarrhea," *Am J Gastroenterol.*, 89(4):519-23 (1994).
Ananthakrishnan et al., "Excess hospitalisation burden associated with Clostridium difficile in patients with inflammatory bowel disease," *Gut*, 57(2):205-210 (2007).

Andrews et al., "'Putting back the bugs': Bacterial Treatment Relieves Chronic Constipation and Symptoms of Irritable Bowel Syndrome," *Med. J. Aust.*, 159(9):633-634 (1993).
Andrews et al., "Bacteriotherapy for Chronic Constipation—A Long Term Follow-Up," *Gastroenterol*, 108:A563 Abstract (1995).
Andrews et al., "Chronic Constipation (CC) may be reversed by Bacteriotherapy," *Gastroenterol*, 106:A459 (1994).
Andrews et al., "Chronic constipation reversed by restoration of bowel flora. A case and a hypothesis," *European Journal of Gastroenterology & Hepatology*, 4:245-247 (1992).
Anorexia nervosa, Encyclopedia Index A, healthAtoZ, Medical Network, Inc., pp. 1-7, n.d., Web, Nov. 23, 2005 <http://www.healthatoz.com/healthatoz/Atoz/ency/anorexia_nervosa.jsp>.
Arkkila et al., "Fecal Bacteriotherapy for Recurrent *Clostridium difficile* Infection," *Gastroenterology*, 138(5):S1-S5 (2010).
Aroniadis et al., "Long-Term Follow-up Study of Fecal Microbiota Transplantation (FMT) for Severe or Complicated *Clostridium difficile* Infection (CDI)," *Gastroenterol*, 144(Suppl 1):S185 (2013).
Autism, Health Encyclopedia—Diseases and Conditions, The Health Scout Network, pp. 1-5, n.d., Web, Nov. 22, 2005 <www.healthscout.com>.
Autism, Treatment, Prognosis, Healthcommunities.com, Inc., pp. 1-4, n.d., Web. Jan. 28, 2009 <http://www.neurologychannel.com/common/PrintPage.php>.
Autism: Mayo Clinic.com, Mayo Foundation for Medical Education and Research, pp. 1-7, May 31, 2008, Web. Jan. 28, 2009 <http://www.mayoclinic.com/print/autism/DS00348/METHOD=print&DSECTION=all>.
Backhed et al., "Host-bacterial mutualism in the human intestine," *Science*, 307(5717):1915-1920 (2005).
Backhed et al., "Mechanisms underlying the resistance to diet-induced obesity in germ-free mice," *PNAS USA*, 104(3):979-984 (2007).
Backhed et al., "The gut microbiota as an environmental factor that regulates fat storage," *PNAS USA*, 101(44):15718-15723 (2004).
Bakken et al., "Fecal bacteriotherapy for recurrent Clostridium difficile infection," *Anaerobe*, 15(6):285-289 (2009).
Bakken et al., "Treating Clostridium difficile Infection with Fecal Microbiota Transplantation," *Clinical Gastroenterology and Hepatology*, 9(12):1044-1049 (2011).
Bartlett et al., "Clinical recognition and diagnosis of Clostridium difficile infection," *Clin Infect Dis.*, 46(Suppl 1):S12-S18 (2008).
Bartlett, "Clostridium difficile-associated Enteric Disease," *Curr Infect Dis Rep.*, 4(6):477-483 (2002).
Bengmark et al., "Bioecological control of inflammatory bowel disease," *Clinical Nutrition*, 26(2):169-181 (2007).
Bennet et al., "Treatment of ulcerative colitis by implantation of normal colonic flora," *Lancet*, 333(8630):164 (1989).
Benson et al., "Changing epidemiology of Clostridium difficile-associated disease in children," *Infect Control Hosp Epidemiol.*, 28(11):1233-1235 (2007).
Blaser et al., "What are the consequences of the disappearing human microbiota?" *Nat. Rev. Microbiol.*, 7(12):887-894 (2009).
Blaser, "Who are we? Indigenous microbes and the ecology of human diseases," *EMBO Rep*, 7(10):956-960 (2006).
Bolte, "Autism and *Clostridium tetani*," *Medical Hypotheses*, 51(2):133-144 (1998).
Borody et al., "The GI Microbiome and its Role in Chronic Fatigue Syndrome: a Summary of Bacteriotherapy," *ACNEM Journal*, 31(3):3-8 (2012).
Borody et al., "Anti-MAP Rescues Anti-TNF Failures for Over 4 Years," *Gastroenterol*, 136(5)Suppl 1:A-681 (2009).
Borody et al., "Anti-MAP Therapy for Pediatric Crohn's Disease," *Am J Gastroenterol*, 108(Suppl 1):S516 (2013).
Borody et al., "Anti-MAP Therapy in the Treatment of Active Crohn's Disease," *J Gastroenterol & Hepatol*, 20(Suppl):A2 (2005).
Borody et al., "Anti-mycobacterial therapy in Crohn's disease heals mucosa with longitudinal scars," *Digestive & Liver Disease*, 39(5):438-444 (2007).
Borody et al., "Anti-*Mycobacterium avium* SS *Paratuberculosis* (MAP) Therapy and Fistula Closure in Patients with Severe Crohn's Disease," *Am J Gast*, A101:S440 (2006).

(56) References Cited

OTHER PUBLICATIONS

Borody et al., "Bacteriothempy in Chronic Fatigue Syndrome (CFS): A retrospective review," *Am J Gastro*, 107(S1):A1481 (2012).
Borody et al., "Bacteriothempy Using Fecal Flora: toying with human motions" *J. Clin. Gastroenterol.*, 38(6):475-483 (2004).
Borody et al., "Bowel-flora alteration: a potential cure for inflammatory bowel in disease and irritable bowel syndrome?" *Med. J. Aust.*, 150:604 (1989).
Borody et al., "Changes in Crohn's Disease Activity Index and C-Reactive Protein Levels During Anti-MAP Therapy," *AM J Gastro*, 104(S3):A1293 (2009).
Borody et al., "Clostridium difficile Complicating Inflammatory Bowel Disease: Pre- and Post-Treatment Findings," *Gastroenterol*, 134(4)Suppl 1:A-361 (2008).
Borody et al., "Could fecal microbiota transplantation cure all Clostridium difficile infections?," *Future Microbiol*, 9:1-3 (2014).
Borody et al., "Entamoeba histolytica: another cause of Crohn's Disease," *AM J Gastro*, 104(S3):A990 (2009).
Borody et al., "Faecal bacteriotherapy (FB) for chronic *C. difficile* (Cd) syndromes," *J Gastroenterol Hepatol*, 18(Suppl):B8 (Abstract) (2003).
Borody et al., "Fecal bacteriotherapy in the treatment of recurrent C. difficile infection," *UpToDate*, pp. 1-6 (2006).
Borody et al., "Fecal Microbiota Transplantation (FMT) in Multiple Sclerosis (MS)," *AM J Gastro*, 106(S2):A942 (2011).
Borody et al., "Fecal mierobiota transplantation and emerging applications," *Nat. Rev. Gastroenterol. Hepatol.*, 9(2):88-96 (2011).
Borody et al., "Fecal microbiota transplantation for *Clostridium difficile* infection: A surgeon's perspective" *Seminars in Colon and Rectal Surgery*, 25 :163-166 (2014).
Borody et al., "Fecal microbiota transplantation in gastrointestinal diseases—What practicing physicians should know," *Polish Archives of Internal Medicine*, 125(11):852-858 (2015).
Borody et al., "Fecal microbiota transplantation in the treatment of recurrent Clostridium difficile infection," *UpToDate*, pp. 1-4, (2015).
Borody et al., "Fecal Microbiota Transplantation in Ulcerative Colitis: Review of 24 Years Expeiience," *Am J Gastro*, 107(Supp 1):A1644 (2012).
Borody et al., "Fecal mierobiota transplantation: a new standard treatment option for *Clostridium difficile* infection," *Expert Rev Anti Infect Ther.*, 11(5):447-449 (2013).
Borody et al., "Fecal microbiota transplantation: current status and future directions," *Expert Review of Gastroenterology & Hepatology*, 5(6):653-655 (2011).
Borody et al., "Fecal Microbiota Transplantation: Expanding Horizons for *Clostridium difficile* Infections and Beyond," *Antibiotics*, 4:254-266 (2015).
Borody et al., "Fecal Microbiota Transplantation: Indications, Methods, Evidence, and Future Directions," *Curr Gastroenterol Rep*, 15:337-344 (2013).
Borody et al., "Fecal Microbiota Transplantation: Techniques, Applications, and Issues," *Gastroenterol Clin North Am*, 41:781-803 (2012).
Borody et al., "Irritable Bowel Syndrome and *Dientamoeba fragilis*," *ASM Sydney National Conference*, pp. 4-5 (2002).
Borody et al., "Is Crohn's Disease Ready for Fecal Microbiota Transplantation?," *J Clin Gastroenterol*, 48(7):582-583 (2014).
Borody et al., "Myoclonus-dystonia affected by GI Microbiota?," *AM J Gastro*, 106(S2):A940 (2011).
Borody et al., "Novel appearance of healing mucosa following anti-*Mycobacterium avium paratuberculosis* therapy for Crohn's disease," *J Gastroenterol Hepatol*, 19(Suppl):A210 (2004).
Borody et al., Reversal of Idiopathic Thrombocytopenic Purpura [ITP] with Fecal Microbiota Transplantation [FMT], *AM J Gastro*, 106(S2):A941 (2011).
Borody et al., "Reversal of Inflammatory Bowel Disease (IBD) with Recurrent Faecal Microbiota Transplants (FMT)," *AM J Gastro*, 106(S2):A979 (2011).
Borody et al., "Severe recurrent Crohn's Disease of ileocolonic anastomosis and antimicrobial (anti-mycobacterial therapy)," *Gut*, 55:1211 (2006).
Borody et al., "Therapeutic faecal microbiota transplantation: current status and future developments," *Curr Opin Gastroenterol*, 30:97-105 (2014).
Borody et al., "Treatment of chronic constipation and colitis using human probiotic infusions," *Proceedings of Prebiotics and Probiotics and the New Foods Conference*, 2-4:228 Abstract (2001).
Borody et al., "Treatment of First-time Clostridium difficile Infection with Fecal Microbiota Transplantation," Poster Presentation, *2015 ACG Annual Scientific Meeting*, Honolulu, Hawaii, USA (2015).
Borody et al., "Treatment of Severe Constipation Improves Parkinson's Disease (PD) Symptoms," AM J Gastro, 104(S3):A999 (2009).
Borody et al., "Treatment of Severe Crohn's Disease (CD)-Using Rifabutin-Macrolide-Clofazimine Combination: Results at 30-37 Months," *Gastroenterology*, 118(4):A1334 Abstract (2000).
Borody et al., Treatment of Severe Crohn's Disease Using Rifabutin-Macrolide-Clofazimine Combination—Results at 38-43 Months, *J Gastroenterol & Hepatol*, 15 (Suppl.):J102 (2000).
Borody et al., "Treatment of severe Crohn's disease using antimycobacterial triple therapy—approaching a cure?," *Digest Liver Dis*, 34(1):29-38 (2002).
Borody et al., "Treatment of ulcerative colitis using fecal bacteriotherapy," *J. Clin. Gastroenterol.*, 37(1):42-47 (2003).
Borody, "Bacteriotherapy for Chronic Fatigue Syndrome—A Long Term Follow-Up Study," *Proceedings of ACMA Complementary Medicine Sydney*, p. 1 (1995).
Borody, "Flora Power—Fecal Bacteria Cure Chronic C. difficile Diarrhoea," *Am J Gastroenterol*, 95(11):3028-3029 (2000).
Borody, "Is the Infected Patient too 'Difficile' to Treat?," *The Australian Society for Microbiology* 2009 Perth, SY03 & SY03.1, p. 27 & 56, (2009).
Borody, "Letter to the Editor—Response to Drs. Famularo et al.," *AJG*, 96(7):2262-2264 (2001).
Borriello, "Clostridial Disease of the Gut," *Clinical Infectious Diseases*, The University of Chicago, 20(Suppl 2):S242-S250 (1995).
Bowden et al., "Pseudomembraneous enterocolitis: mechanism of restoring floral homeostasis," *Am Surg.*, 47(4):178-183 (1981).
Brandt et al., "Endoscopic Fecal Microbiota Transplantation. "First-Line" Treatment for Severe Clostridium difficile Infection?" *J. Clin. Gastroenterol.*, 45(8):655-657 (2011).
Brandt et al., "Fecal microbiota transplantation for recurrent *Clostridium difficile* infection," *J Clin Gastroenterol.*, 45(Suppl):S159-S167 (2011).
Brandt et al., Safety of Fecal Microbiota Transplantation (FMT) in Immunocompromised (Ic) Patients with Inflammatory Bowel Disease (IBD), *Am J Gastroenterol*, 108(Suppl 1):S556 (2013).
Campbell et al., "The many faces of Crohn's Disease: Latest concepts in etiology," *OJIM*, 2(2):107-115 (2012).
Cano et al., "Revival and identification of bacterial spores in 25-40 million year old Dominican Amber Science," *Science*, 268(5213):1060-1064 (1995).
Center for Disease Control, "Severe Clostridium difficile-associated disease in populations previously at low risk—four states, 2005." *Morbidity and Mortality Weekly Report*, 54(47):1201-1205 (2005).
Chamberlain et al., "MAP-associated Crohn's Disease, MAP, Koch's postulates, causality and Crohn's Disease," *Digestive and Liver Disease*, 39:790-794 (2007).
Chamberlin et al., "Primary treatment of Crohn's disease: combined antibiotics taking center stage," *Expert Rev. Clin. Immunol.*, 7(6):751-760 (2011).
Chang et al., "Decreased diversity of the fecal Microbiome in recurrent Clostridium difficile-associated diarrhea," *J. Infect. Dis.*, 197(3):435-438 (2008).
Chen et al., "A mouse model of Clostridium difficile-associated disease," *Gastroenterology*, 135(6):1984-1992 (2008).
Chopra et al., "Recent epidemiology of Clostridium difficile infection during hematopoietic stem cell transplantation," *Clin Transplant.*, 25(1):E82-E87 (2011).
Citron et al., "In Vitro Activities of CB-183,315, Vancomycin, and Metronidazole against 556 Strains of *Clostridium difficile*, 445

(56) References Cited

OTHER PUBLICATIONS

Other Intestinal Anaerobes, and 56 *Enterobacteriaceae* Species," *Antimicrob Agents Chemother.*, 56(3):1613-1615 (2012).

Claesson et al., "Comparison of two next-generation sequencing technologies for resolving highly complex microbiota composition using tandem variable 16S rRNA gene regions," *Nucleic Acids Research*, 38(22):1-13 (2010).

Clancy et al., "Anti-MAP Therapy Induces and Maintains Remission in Severe Crohn's Disease," *Ann NY Acad Sci*, p. 1 (2005).

Claus et al., "Colonization-induced host-gut microbial metabolic interaction," *MBio*, 2(2):e00271-00210 (2011).

Claus et al., "Systemic multicompartmental effects of the gut microbiome on mouse metabolic phenotypes," *Mol. Syst. Biol.*, 4(1):219 (2008).

Cohen et al., "Clinical practice guidelines for Clostridium difficile infection in adults: 2010 update by the society for healthcare epidemiology of America (SHEA) and the infectious diseases society of America (IDSA)," *Infect Control Hosp Epidemiol.*, 31(5):431-55 (2010).

Crohn's Disease, Prevention, Health Guide A-Z, WebMDHealth, pp. 1-2, n.d., Web, Oct. 23, 2005 <http://mywebmd.com/hw/inflammatory.sub.--bowel/uf6012.asp>.

Crowther, "Transport and Storage of Faeces for Bacteriological Examination," *Journal of Applied Bacteriology*, 34(2):477-483 (1971).

Cutolo et al., "Fecal feedings as a therapy in *Staphylococcus enterocolitis*," *NY State J Med*, 59:3831-3833 (1959).

Dale et al., "Molecular interactions between bacterial symbionts and their hosts," *Cell*, 126(3):453-465 (2006).

Dan et al., "Comparison of preservation media and freezing conditions for storage of specimens of faeces," *J. Med Microbiology*, 28:151-154 (1989).

Defang et al., "In vitro and in vivo evaluation of two extended release preparations of combination metformin and glipizide," *Drug Develop. & Indust. Pharm.*, 31:677-685 (2005).

Dendukuri et al., "Probiotic therapy for the prevention and treatment of Clostridium difficile-associated diarrhea: a systematic review," *CMAJ*, 173(2):167-170 (2005).

Derwent Abstract Accession No. 98-230427/20, WO 98/13068 A, (Kuperman VB) Apr. 2, 1998.

Dethlefsen et al., "An ecological and evolutionary perspective on human-microbe mutualism and disease," *Nature*; 449(7164):811-818 (2007).

DuPont, "The search for effective treatment of Clostridium difficile infection," *N Engl J Med.*, 364(5):473-475 (2011).

Eckburg et al., "Diversity of the human intestinal microbial flora," *Science*, 308(5728):1635-1638 (2005).

Eiseman et al., "Fecal enema as an adjunct in the treatment of pseudomembranous enterocolitis," *Surgery*, 44(5):854-859 (1958).

Extended European Search Report dated Apr. 3, 2014, in European Patent Application No. 11813951.8.

Faust et al., "Treatment of recurrent pseudomembranous colitis (RPMC) with stool transplantation (ST): Report of six (6) cases," *Can J Gastroenterol.*, 16:A43 (2002).

Fenton et al., "Pseudomembranous colitis associated with antibiotic therapy—an emerging entity," *Can Med Assoc J.*, 111(10):1110-1111 (1974).

Floch et al., "Probiotics and Dietary Fiber, The Clinical Coming of Age of Intestinal Microecology," *J. Clin. Gastroenterology*, 27(2):99-100 (1998).

Floch, "Fecal Bacteriotherapy, Fecal Transplant, and the Microbiome," *J. Clin. Gastroenterol.*, 44(8):529-530 (2010).

Flotterod et al., "Refractory Clostridium difficile infection. Untraditional treatment of antibiotic-induced colitis," *Tidsskr Nor Laegeforen*, 111:1364-1365 (1991).

Frantzen et al., "Empirical evaluation of preservation methods for faecal DNA," *Molecular Ecology*, 7(10):1423-1428 (1998).

Freeman et al., "The changing epidemiology of Clostridium difficile infections," *Clin Microbiol. Rev.*, 23(3):529-549 (2010).

Frese et al., "The evolution of host specialization in the vertebrate gut symbiont Lactobacillus reuteri," *PloS Genet.*, 7(2):e1001314 (2011).

Garborg et al., "Results of faecal donor instillation therapy for recurrent Clostridium difficile-associated diarrhoea," *Scand J Infect Dis.*,42(11-12):857-61 (2010).

Garey et al., "Meta-analysis to assess risk factors for recurrent Clostridium difficile infection," *J. Hosp. Infect.*, 70(4):298-304 (2008).

Gerding, "Management of Clostridium difficile infection: thinking inside and outside the box," *Clin Infect Dis.*, 51(11):1306-13 (2010).

Gitlin et al., "*Mycobacterium avium ss paratuberculosis*-associated Diseases: Piecing the Crohn's Puzzle Together," *J Clin Gastroenterol*, 46(8):649-655 (2012).

Gough et al., "Systematic review of intestinal microbiota transplantation (fecal bacteriotherapy) for recurrent Clostridium difficile infection," *Clin. Infect. Dis.*, 53(10):994-1002 (2011).

Grehan et al., "Durable alteration of the colonic microbiota by the administration of donor fecal flora," *Journal of Clinical Gastroenterology*, 44(8):551-561 (2010).

Guarner et al., "Gut flora in health and disease," *Lancet*, 361(9356):512-519 (2003).

Gustafsson et al., "Faecal Short-Chain Fatty Acids in Patients with Antibiotic-Associated Diarrhoea, before and after Faecal Enema Treatment," *Scand J Gastroenterol*, 33:721-727 (1998).

Hamilton et al., "Change in microbial community composition of in patients with recalcitrant Clostridium difficile colitis treated with fecal bacteriotherapy," International Human Microbiome Congress, Poster and Presentation, Vancouver, ON, Canada, Mar. 9-11, 2011.

Hamilton et al., "High-throughput DNA sequence analysis reveals stable engraftment of gut microbiota following transplantation of gut microbiota following transplantation of previously frozen fecal bacteria," *Gut Microbes*, 4(2):1-11 (2013).

Hamilton et al., "Standardized Frozen Preparation for Transplantation of Fecal Microbiota for Recurrent Clostridium difficile Infection," Article and Supplementary Material, *Am. J. Gastroenterol.*, 107(5):761-767 (2012).

Hellemans et al., "Fecal transplantation for recurrent Clostridium difficile colitis, an underused treatment modality," *Acta Gastroenterol Belg.*, 72(2):269-70 (2009).

Henriksson et al., "Probiotics under the regulatory microscope," *Expert Opin. Drug Saf.*, 4(6):1-9 (2005).

Hensel et al., "Vagal Ascent and Distribution of 125 I-Tetanus Toxin after Injection into the Anterior Wall of the Stomach," *Naunyn-Schmiedeberg's Arch. Pharmacol*, 276:395-402 (1973).

Hooper et al., "How host-microbial interactions shape the nutrient environment of the mammalian intestine," *Annu. Rev. Nutr.*, 22:283-307 (2002).

Hope et al., "Sporadic colorectal cancer-role of the commensal microbiota," *FEMS Microbiol. Lett.*, 244:1-7 (2005).

Hota et al., "Determining Mortality Rates Attributable to Clostridium difficile Infection," *Emerg. Infect. Dis.*, 18(2):305-307 (2012).

Hota et al., "Oral Vancomycin Followed by Fecal Transplant Versus Tapering Oral Vancomycin," U.S. National Institutes of Health, Clinical Study No. NCT01226992, Oct. 20, 2010, last updated Jan. 14, 2013, Web, May 20, 2014, pp. 1-4 <http://clinicaltrials.gov/ct2/show/NCT01226992>.

Hu et al., "Prospective derivation and validation of a clinical prediction rule for recurrent Clostridium difficile infection," *Gastroenterology*, 136:1206-1214 (2009).

Huang et al., "Once-daily propranolol extended-release tablet dosage form: formulation design and in vitro/in vivo investigation," *European J. of Pharm. & Biopharm.*, 58:607-614 (2004).

Huttenhower et al., "Structure, function and diversity of the healthy human microbiome," The Human Microbiome Project Consortium, *Nature*, 486:207-214 (2012).

Inflammatory Bowel Disease Facts, Disease Prevention and Treatment Strategies, Crohn's Disease and Inflammatory Bowel Disease (IBD), HealingWithNutrition.com, pp. 1-4, n.d., Web, Oct. 23, 2005 <http://www.HealingWithNutrition.com/disease/inflambowels/chrohns.html>.

(56) References Cited

OTHER PUBLICATIONS

International Preliminary Examination Report completed Nov. 19, 2002, in International Application No. PCT/AU2001/000907, 19 pgs.
International Preliminary Report on Patentability completed Dec. 12, 2012, in International No. PCT/AU2011/000987, 35 pgs.
International Preliminary Report on Patentability completed Mar. 12, 2015, in International Application No. PCT/AU2013/001362, 29 pgs.
International Preliminary Report on Patentability dated Sep. 10, 2013, in International Application No. PCT/US2012/028484, 10 pgs.
International Search Report and Written Opinion dated Feb. 5, 2014, in International Application No. PCT/AU2013/001362, 17 pgs.
International Search Report and Written Opinion dated Jul. 31, 2014, in International Application No. PCT/US2014/027391, 16 pgs.
International Search Report and Written Opinion dated Oct. 28, 2011, in International No. PCT/AU2011/000987, 18 pgs.
International Search Report dated Aug. 10, 2012, in International Application No. PCT/US2012/028484, 7 pgs.
International Search Report dated Jul. 29, 2014, in International Application No. PCT/AU2014/000478, 7 pgs.
Irrgang et al., "The historical Development of Mutaflor therapy," Ardeypharm GmbH, pp. 1-38 (1988) <http://www.ardeypharm.de/pdfs/en/mutaflor_historical_e.pdf?>.
Irritable Bowel Syndrome (IBS), Health A to Z, InteliHealth, pp. 1-4, n.d., Web, Oct. 23, 2005 <http://www.intelihealth.com>.
Issa et al., "Clostridium difficile and Inflammatory Bowel Disease," *Inflamm Bowel Dis.*, 14(10):1432-1442 (2008).
Issa et al., "Impact of Clostridium difficile on inflammatory bowel disease," *Clin. Gastroenterol. Hepatol.*, 5(3):345-351 (2007).
Jarvis et al., "National point prevalence of Clostridium difficile in US health care facility inpatients, 2008," *Am. J. Infect. Control*, 37:263-270 (2009).
Johnson et al., "Interruption of Recurrent Clostridium difficile-Associated Diarrhea Episodes by Serial Therapy with Vancomycin and Rifaximin," *Clin. Infect. Dis.*, 44(6):846-848 (2007).
Johnson et al., "Rifaximin Redux: Treatment of recurrent Clostridium difficile infections with Rifaximin immediately post-vancomycin treatment," *Anaerobe*, 15(6):290-291 (2009).
Kageyama et al., "Emendation of genus *Collinsella* and proposal of *Collinsella stercoris* sp. nov. and *Collinsella intestinalis* sp. nov.," *International Journal of Systematic and Evolutionary Microbiology*, 50:1767-1774 (2000).
Kamboj et al., "Relapse versus reinfection: surveillance of Clostridium difficile infection," *Clin Infect Dis.*, 53(10):1003-1006 (2011).
Karas et al., "A review of mortality due to Clostridium difficile infection," *J Infect.*, 61(1):1-8 (2010).
Kassam et al., "Fecal transplant via retention enema for refractory or recurrent Clostridium difficile infection," *Arch Intern Med.*, 172(2):191-193 (2012).
Kelly et al., "Clostridium difficile—more difficult than ever," *N. Engl. J. Med.*, 359(18):1932-1940 (2008).
Kelly et al., "Clostridium difficile colitis," *N. Engl. J. Med.*, 330(4):257-62 (1994).
Kelly et al., "Fecal Microbiota Transplant for Treatment of *Clostridium difficile* Infection in Immunocompromised Patients," *Am J Gastroenterol*, 109:1065-1071 (2014).
Kelly et al., "Fecal microbiota transplantation for relapsing Clostridium difficile infection in 26 patients: methodology and results," *J. Clin. Gastroenterol.*, 46(2):145-149 (2012).
Khanna et al., "The epidemiology of community-acquired Clostridium difficile infection: a population-based study," *Am J Gastroenterol.*, 107(1):89-95 (2012).
Khanna et al., "The growing incidence and severity of Clostridium difficile infection in inpatient and outpatient settings," *Expert Rev Gastroenterol Hepatol.*, 4(4):409-16 (2010).
Kharidia et al., "The Activity of a Small Lytic Peptide FTP-7 on *Staphylococcus aureus* Biofilms," *J. Microbiol.*, 49(4):663-668 (2011).

Khoruts et al., "Changes in the composition of the human fecal microbiome after bacteriotherapy for recurrent Clostridium difficile-associated diarrhea," *J. Clin. Gastroenterol.*, 44(5):354-360 (2010).
Khoruts et al., "Therapeutic transplantation of the distal gut microbiota," *Mucosal Immunol.*, 4(1):4-7 (2011).
Kim et al., "Effect of Rifampin on the Plasma Concentration and the Clinical Effect of Haloperidol Concomitantly Administered to Schizophrenic Patients," *Journal of Clinical Psychopharmacology*, 16(3):247-252 (1996).
Kim et al., "In Vitro Culture Conditions for Maintaining a Complex Population of Human Gastrointestinal Tract Microbiota," *Journal of Biomedicine and Biotechnology*, 2011(Article ID 838040):1-10 (2011) <http://www.hindawi.com/journals/bmri/2011/838040/>.
Kleiman et al., "Comparison of two coprologieal methods for the veterinary diagnosis of fasciolosis," *Arquivo Brasileiro de Medicina Veterinária e Zootécnica*, 55(2):181-185 (2005).
Kobashi et al., "Metabolism of Sennosides by Human Intestinal Bacteria," *Journal of Medicinal Plant Research*, 40(3):225-236 (1980).
Kuijper et al. "Update of Clostridium difficile Infection due to PCR Ribotype 027 in Europe, 2008," *Euro. Surveill.*, 13(31):Article 5 (2008).
Kuksal et al., "Formulation and In Vitro, In Vivo Evaluation of Extended-release Matrix Tablet of Zidovudine: Influence of Combination of Hydrophilic and Hydrophobic Matrix Formers," *AAPS Pharm*, 7(1):E1-E9 (2006).
Kyne et al., "Association between antibody response to toxin A and protection against recurrent Clostridium difficile diarrhea," *Lancet*, 357(9251):189-93 (2001).
Kyne et al., "Asymptomatic carriage of Clostridium difficile and serum levels of IgG antibody against toxin A," *N Engl J Med.*, 342(6):390-397 (2000).
Kyne et al., "Factors associated with prolonged symptoms and severe disease due to Clostridium difficile," *Age and Ageing*, 28(2):107-13 (1999).
Kysela et al., "Serial analysis of V6 ribosomal sequence tags (SARST-V6): a method for efficient, high-throughput analysis of microbial community composition," *Environmental Microbiology*, 7(3):356-364 (2005).
Labbé et al., "Clostridium difficile infections in a Canadian tertiary care hospital before and during a regional epidemic associated with the BI/NAP1/027 strain," *Antimicrob Agents Chemother.*, 52(9):3180-7 (2008).
Lamontagne et al., "Impact of emergency colectomy on survival of patients with fulminant Clostridium difficile colitis during an epidemic caused by a hypervirulent strain," *Ann. Surg.*, 245(2):267-272 (2007).
Lee, "A Prospective Randomized Multi-Centre Trial of Fresh vs. Frozen-and-Thawed Human Biotherapy (Fecal Transplant) for Recurrent Clostridium difficile Infection," U.S. National Institutes of Health, Clinical Study No. NCT01398969, pp. 1-4, last updated Feb. 27, 2014, Web, May 20, 2014 <http://clinicaltrials.gov/ct2/show/NCT01398969>.
Leis et al., "Fecal microbiota transplantation: A 'How-To' guide for nurses," *Collegian*, 22:445-451 (2015).
Lewis et al., "Stool form scale as a useful guide to intestinal transit time," *Scand. J. Gastroenterol.*, 32(9):920-924 (1997).
Ley et al., "Ecological and evolutionary forces shaping microbial diversity in the human intestine," *Cell*, 124:837-848 (2006).
Ley et al., "Evolution of mammals and their gut microbes," *Science*, 320(5883):1647-1651 (2008).
Ley et al., "Microbial ecology. human gut microbes associated with obesity," *Nature*, 444(7122):1022-3 (2006).
Ley et al., "Worlds within worlds: evolution of the vertebrate gut microbiota," *Nat. Rev. Microbiol.*, 6(10):776-788 (2008).
Lin et al., "Twelve Week Storage Trial of Microbial Viability in Lyophilized and Frozen Fecal Microbiota Preparations," Poster Presentation—Digestive Disease Week 2015, Washington, D.C. USA.
Longstreth, "Irritable bowel syndrome: A multibillion-dollar problem," *Gastroenterology*, 109(6):2029-2031 (1995).

(56) References Cited

OTHER PUBLICATIONS

Loo et al., "A predominantly clonal multiinstitutional outbreak of Clostridium difficile-associated diarrhea with high morbidity and mortality," *N Engl J Med*, 353(23):2442-9 (2005).
Loo et al., "Host and pathogen factors for Clostridium difficile infection and colonization," *N Engl J Med*, 365(18):1693-703 (2011).
Louie et al., "Fidaxomicin versus vancomycin for Clostridium difficile infection," *N. Engl. J. Med.*, 364(5):422-431 (2011).
Louie et al., "Home-based fecal flora infusion to arrest multiply-recurrent C. difficile infection," ICAAC/IDSA Conference, Abstract #K-4201 (2008).
Lu, "Taboo transplant: How new poo defeats superbugs," *Science News*, 1:90-91 (2011).
Lund-Tonnesen et al., "Clostridium difficile-associated diarrhea treated with homologous faeces," *Tidsskr Nor Lageforen*, 118:1027-1030 (1998).
MacConnachie et al., "Faecal transplant for recurrent Clostridium difficile-associated diarrhoea: a UK case series," *QJM*, 102(11):781-784 (2009).
MacDonald et al., "Formation of Ursodeoxycholic Acid from Chenodeoxycholic Acid by a 7β-Hydroxysteriod Dehydrogenase-Elaborating *Eubacterium aerofaciens* Strain Cocultured with 7α-Hydroxysteriod Dehydrogenase-Elaborating Organisms," *Applied and Environmental Microbiology*, 44(5):1187-1195 (1982).
Macpherson et al., "Induction of Protective IgA by Intestinal Dendritic Cells Carrying Commensal Bacteria," *Science*, 303:1662-1665 (2004).
Madsen, "The use of probiotics in gastrointestinal disease," *Can J Gastroenterol*, 15(12):817-22 (2001).
Marchesi et al., "The normal intestinal microbiota," *Curr. Opin. Infect. Dis.*, 20(5):508-513 (2007).
Martin, "Development and Delivery of a Treatment for Clostridium difficile," Bacteriotherapy, pp. 1-2, n.d., Web, Feb. 10, 2012 <www.bacteriotherapy.org>.
Maslowski et al., "Diet, gut microbiota and immune responses," *Nat Immunol.*, 12(1):5-9 (2011).
McDonald et al., "An Epidemic, Toxin Gene-Variant Strain of Clostridium difficile," *N Engl J Med.*, 353(23):2433-41 (2005).
McDonald et al., "Clostridium difficile Infection in Patients Discharged from US Short-stay Hsopitals, 1996-2003" *Emerg. Infect. Dis*, 12(3):409-415 (2006).
McFarland et al., "Breaking the Cycle: Treatment Strategies for 163 Cases of Recurrent Clostridium difficile Disease," *Am. J. Gastroenterol.*, 97(7):1769-1775 (2002).
McFarland et al., "Implications of the changing face of Clostridium difficile disease for health care practitioners," *Am J Infect Control.*, 35(4):237-253 (2007).
McFarland et al., "Meta-Analysis of Probiotics for the Prevention of Antibiotic Associated Diarrhea and the Treatment of Clostridium difficile Disease," *Am J Gastroenterol.*, 101(4):812-22 (2006).
McFarland et al., "Nosocomial Acquisition of Clostridium Difficile Infection," *N Engl J Med.*, 320(4):204-210 (1989).
McFarland et al., "Recurrent Clostridium Difficile Disease: Epidemiology and Clinical Characteristics," *Infect Control Hosp Epidemiol.*, 20(1):43-50 (1999).
McFarland et al., "Renewed interest in a difficult disease: Clostridium difficile infections—epidemiology and current treatment strategies," *Curr Opin Gastroenterol.*, 25(1):24-35 (2008).
Miller et al., "Health care-associated Clostridium difficile infection in Canada: patient age and infecting strain type are highly predictive of severe outcome and mortality," *Clin Infect Dis.*, 50(2):194-201 (2010).
Miller et al., "Long-term follow-up of patients with fulminant Clostridium difficile colitis," *J. Gastrointest. Surg.*, 13(5):956-959 (2009).
Miller et al., "Morbidity, mortality, and healthcare burden of nosocomial Clostridium difficile-associated diarrhea in Canadian hospitals," *Infect Control Hosp Epidemiol.*, 23(3):137-40 (2002).
Miller, "The fascination with probiotics for Clostridium difficile infection: lack of evidence for prophylactic or therapeutic efficacy," *Anaerobe*, 15(6):281-284 (2009).
Molecular Studies in Autism, 2004 Funding Cycle, Cure Autism Now, Cure Autism Now Foundation, pp. 1-7 (2005) <www.cureautismnow.org>.
Morris et al., "Clostridium difficile Colitis: An Increasingly Aggressive Iatrogenic Disease?" *Arch Surg.*, 137(10):1096-1100 (2002).
Mullard, "Microbiology: The Inside Story," *Nature*, 453:578-580 (2008).
Mutaflor, "Brief Summary of Therapeutic Principles," Ardeypharm GmbH 0796 D-58313 Herdecke Germany, 6 pgs (2006).
Mutaflor, "For Functional and Inflammatory Bowel Diseases for Extraintestinal Manifestations for Activtion of the Body's In-Built Defences," Ardeypharam GmbH 0796, D-58313 Herdecke Germany, 8 pgs (2006).
Mutaflor, "Safety of Therapy," Ardeypharm GmbH 0796, D-58313 Herdecke Germany, 4 pgs (1988).
Muto et al., "A Large Outbreak of Clostridium difficile-Associated Disease with an Unexpected Proportion of Deaths and Colectomies at a Teaching Hospital Following Increased Fluoroquinolone Use," *Infect Control Hosp Epidemiol.*, 26(3):273-80 (2005).
Nieuwdorp et al., ["Treatment of recurrent Clostridium difficile-associated diarrhoea with a suspension of donor faeces"], *Ned Tijdschr Geneeskd*, 152(35):1927-32 (2008).
O'Hara et al., "The gut flora as a forgotten organ," *EMBO Rep.*, 7(7):688-693 (2006).
O'Brien et al., "The emerging infectious challenge of clostridium difficile-associated disease in Massachusetts hospitals: clinical and economic consequences," *Infect Control Hosp Epidemiol.*, 28(11):1219-27 (2007).
O'Connor et al., "Clostridium difficile Infection Caused by the Epidemic BI/NAP1/027 Strain," *Gastroenterology*, 136(6):1913-1924 (2009).
Paramsothy et al., "Gastroenterologist perceptions of faecal microbiota transplantation," *World J Gastroenterol*, 21(38): 10907-10914 (2015).
Patterson et al., "Special organism isolation: attempting to bridge the gap," *Infect Control Hosp Epidemiol.*, 15(5):335-338 (1994).
Pearce et al., "Modification of the colonic microflora using probiotics: The way forward?," *Gut*, 41(Suppl 3):A63 (1997).
Pearce et al., "The use of probiotic therapy as a novel approach to the management of irritable bowel syndrome: a preliminary study," *J Gastroenterol & Hepatol*, 12(Suppl):A129 (1997).
Pépin et al. "Emergence of Fluoroquinolones as the Predominant Risk Factor for Clostridium difficile-Associated Diarrhea: A Cohort Study During an Epidemic in Quebec," *Clin Infect Dis.*, 41(9):1254-1260 (2005).
Pépin et al., "Clostridium difficile-associated diarrhea in a region of Quebec from 1991 to 2003: a changing pattern of disease severity," *CMAJ*, 171(5):466-472 (2004).
Pépin et al., "Management and Outcomes of a First Recurrence of Clostridium difficile—Associated Disease in Quebec, Canada," *Clin. Infect. Dis.*, 42:758-764 (2006).
Persky et al., "Treatment of recurrent Clostridium difficile-associated diarrhea by administration of donated stool directly through a colonoscope," *Am J Gastroenterol.*, 95(11):3283-3285 (2000).
Petrof et al., "Stool substitute transplant therapy for the eradication of Clostridium difficile infection: 'RePOOPulating' the gut," *Microbiome*, 1:3 (2013).
Petrof, "Harnessing the healthy gut microbiota to cure patients with recurrent C. difficile infection," U.S. National Institutes of Health, Clinical Study No. NCT01372943, pp. 1-2, last updated Nov. 6, 2013, Web, May 22, 2014 <http://clinicaltrials.gov/ct2/show/NCT01372943>.
Pillai et al., "Probiotics for treatment of Clostridium difficile-associated colitis in adults (Review)," *Cochrane Database Syst Rev.*, (1):CD004611 (2008).
Porter, "Coating of pharmaceutical dosage forms," In D.B. Troy (Ed.), *Remington: The Science and Practice of Pharmacy*, Chapter 46, pp. 929-938 (2005).

(56) References Cited

OTHER PUBLICATIONS

Prakash et al., "Colon-targeted delivery of live bacterial cell biotherapeutics including microencapsulated live bacterial cells," *Biologics: Targets & Therapy*, 2(3):355-378 (2008).
Prevention of Sudden Infant Death Syndrome, Healthtouch.com, Thomson Micromedex, pp. 1-4, n.d., Web, Nov. 23, 2005.
Rabeneck et al., "Bleeding and perforation after outpatient colonoscopy and their risk factors in usual clinical practice," *Gastroenterology*, 135(6):1899-1906 (2008).
Rager et al., "Evaluation of rumen transfaunation after surgical correction of left-sided displacement of the abomasum in cows," *J. Am. Vet. Med. Assoc.*, 225(6):915-920 (2004).
Rao et al., "Evaluation of gastrointestinal transit in clinical practice: position paper of the American and European Neurogastroenterology and Motility Societies," *Neurogastroenterol. Motil.*, 23(1):8-23 (2011).
Rea et al., "Gut solutions to a gut problem: bacteriocins, probiotics and bacteriophage for control of *Clostridium difficile* infection," *Journal of Medical Microbiology*, 62:1369-1378 (2013).
Redelings et al., "Increase in Clostridium difficile-related mortality rates, United States, 1999-2004," *Emerg Infect Dis.*, 13(9):1417-1419 (2007).
Rex et al., "American College of Gastroenterology guidelines for colorectal cancer screening 2008," *Am. J. Gastroenterol.*, 104(3):739-750 (2009).
Ricciardi et al., "Increasing prevalence and severity of Clostridium difficile colitis in hospitalized patients in the United States," *Arch Surg.*, 142(7):624-631 (2007).
Rodemann et al., "Incidence of Clostridium difficile infection in inflammatory bowel disease," *Clin Gastroenterol Hepatol.*, 5(3):339-344 (2007).
Rohlke et al., "Fecal flora reconstitution for recurrent Clostridium difficile infection: results and methodology," *J Clin Gastroenterol.*, 44(8):567-570 (2010).
Rolfe et al "Bacterial interference between Clostridium difficile and normal fecal flora," *J Infect Dis.*, 143(3):470-475 (1981).
Round et al., "The gut microbiota shapes intestinal immune responses during health and disease," *Nat. Rev. Immunol.*, 9(5):313-323 (2009).
Rupnik et al., "Clostridium difficile infection: new developments in epidemiology and pathogenesis," *Nat. Rev. Microbiol.*, 7(7):526-536 (2009).
Russell et al., "Fecal bacteriotherapy for relapsing Clostridium difficile infection in a child: a proposed treatment protocol," *Pediatrics*, 126(1):e239-42 (2010).
Sambol et al., "Colonization for the prevention of *Clostridium difficile* disease in hamsters," *J. Infect. Dis.*, 186(12):1781-1789 (2002).
Sandler et al., "Possible Gut-Brain Interaction Contributing to Delayed Onset Autism Symptomatology," *Fourth Int. Symp. Brain-Gut Interactions*, Blackwell Science Ltd., 10(4):33 (1998).
Sandler et al., "Short-Term Benefit From Oral Vancomycin Treatment of Regressive-Onset Autism," *Journal of Child Neurology*, 15(7):429-435 (2000).
Schiller, "Review article, the therapy of constipation," *Ailment Pharmacol. Ther.*, 15:749-763 (2001).
Scholss, "Introducing mothur: Open-Source, Platform-Independent, Community-Supported Software for Describing and Comparing Microbial Communities," *Appl. Environ. Microbiol.*, 75(23):7537-7541 (2009).
Schwan et al., "Relapsing *Clostridium difficile* Enterocolitis Cured by Rectal Infusion of Homologous Faeces," *The Lancet*, 322(8354):845 (1983).
Schwan et al., "Relapsing *Clostridium difficile* Enterocolitis Cured by Rectal Infusion of Normal Faeces," *Scand. J. Infect. Dis.*, 16(2):211-215 (1984).
Seeff et al., "How many endoscopies are performed for colorectal cancer screening? Results from CDC's survey of endoscopic capacity," *Gastroenterology*, 127:1670-1677 (2004).
Sekirov et al., "Gut microbiota in health and disease," *Physiol. Rev.*, 90(3):859-904 (2010).

Setlow, "I Will Survive: Protecting and Repairing Spore DNA," *Journal of Bacteriology*, 174(9):2737-2741 (1992).
Setlow, "The bacterial spore: nature's survival package," *Culture*, 26(2):1-4 (2005).
Shim et al., "Primary symptomless colonisation by *Clostridium difficile* and decreased risk of subsequent diarrhea," *The Lancet*, 351(9103):633-666 (1998).
Silverman et al., "Success of self-administered home fecal transplantation for chronic Clostridium difficile infection," *Clin. Gastroenterol. Hepatol.*, 8(5):471-473 (2010).
Simor et al., "Clostridium difficile in long-term-care facilities for the elderly," *Infect Control Hosp Epidemiol.*, 23(11):696-703 (2002).
Singh et al., "Do NSAIDs, antibiotics, infections, or stress trigger flares in IBD?" *Am J Gastroenterol.*, 104(5):1298-1313 (2009).
Sleator, "The human superorganism—of microbes and men," *Med. Hypotheses*, 74(2):214-215 (2010).
Smits et al., "Therapeutic potential of fecal microbiota transplantation," *Gastroenterology*, 145:946-953 (2013).
Surawicz et al., "Treatment of refractory and recurrent Clostridium difficile infection," *Nat. Rev. Gastroenterol. Hepatol.*, 8(6):330-339 (2011).
Surawicz, "Reining in Recurrent Clostridium difficile Infection—Who's at Risk?," *Gastroenterology*, 136:1152-1154 (2009).
Sutherland et al., "Lyophilized Clostridium perfringens 3 alpha- and Clostridium bifermentans 7 alpha-hydroxysteroid dehydrogenases: two new stable enzyme preparations for routine bile acid analysis," *Biochim Biophys Acta*, 962(1):116-121 (1988).
Takeda et al., "Serum Haloperidol Levels of Schizophrenics Receiving Treatment for Tuberculosis," *Clinical Neuropharmacology*, 9(4):386-397 (1986).
Tannock et al., "A new macrocyclic antibiotic, fidaxomicin (OPT-80), causes less alteration to the bowel microbiota of Clostridium difficile-infected patients than does vancomycin," *Microbiology*, 156(11):3354-3359 (2010).
Taras et al., "Reclassification of Eubacterium formicigenerans Holdeman and Moore 1974 as *Dorea formicigenerans* gen. nov., comb. nov., and description of *Dorea longicatena* sp. nov., isolated from human faeces," *International Journal of Systematic and Evolutionary Microbiology*, 52:423-428 (2002).
Teasley et al., "Prospective randomised trial of metronidazole versus vancomycin for Clostridium-difficile-associated diarrhoea and colitis," *The Lancet*, 2(8358):1043-1046 (1983).
Tilg et al., "Gut microbiome, obesity, and metabolic dysfunction," *J. Clin. Invest.*, 121(6):2126-2132 (2011).
Tvede et al., "Bacteriotherapy for chronic relapsing Clostridium difficile diarrhea in six patients," *The Lancet*, 1:1156-1160 (1989).
Van der Waaij et al., "Direct Flow Cytometry of Anaerobic Bacteria in Human Feces," *Cytometry*, 16:270-279 (1994).
Van Nood et al., "Struggling with Recurrent Clostridium difficile Infections: Is Donor Faeces the Solution?," *Euro Surveill.*, 14(34):1-6 (2009).
Van Nood, "Duodenal infusion of donor feces for recurrent Clostridium difficile," *New England Journal of Medicine*, 368(5):407-415 (2013).
Veldhuyzen van Zanten et al., "Drug Treatment of Functional Dyspepsia: A Systematic Analysis of Trial Methodology with Recommendations for Design of Future Trials," *Am. J. Gastroenterol.*, 91(4):660-673 (1996).
Veldhuyzen van Zanten et al., "Validation of a 7-point Global Overall Symptom scale to measure the severity of dyspepsia symptoms in clinical trials," *Ailment Pharmacol. Ther.*, 23(4):521-529 (2006).
Venugopal et al., "Fidaxomicin: A Novel Macrocyclic Antibiotic Approved for Treatment of Clostridium difficile Infection," *Clin Infect Dis*, 54(4):568-74 (2012).
Vrieze et al., "The environment within: how gut microbiota may influence metabolism and body composition," *Diabetologia*, 53(4):606-613 (2010).
Walter et al., "Host-microbial symbiosis in the vertebrate gastrointestinal tract and the Lactobacillus reuteri paradigm," *PNAS USA*, 108(Suppl 1):4645-4652 (2011).
Warny et al., "Toxin production by an emerging strain of Clostridium difficile associated with outbreaks of severe disease in North America and Europe," *Lancet*, 366(9491):1079-84 (2005).

(56) References Cited

OTHER PUBLICATIONS

Wasfy et al., "Comparison of Preservation Media for Storage of Stool Samples," *Journal of Clinical Microbiology*, 33(8):2176-2178 (1995).
Weissman et al., "Stool Transplants: Ready for Prime Time?," *Current Gastroenterology Reports*, 14:313-316 (2012).
Wenisch et al., "Comparison of Vancomycin, Teicoplanin, Metronidazole, and Fusidic Acid for the Treatment of Clostridium difficile-Associated Diarrhea," *Clin Infect Dis.*, 22(5):813-818 (1996).
Wettstein et al., "Fecal Bacteriotherapy—An effective Treatment for Relapsing Symptomatic Clostridium difficile Infection," Abstract, 15th United European Gastroenterology Week (UEGW) Poster presentations, United European Gastroenterology Federation, France, A303 (2007).
Wettstein et al., "Skewered diverticulum: another cause of abdominal pain," *Internal Med J*, 31(8):495-496 (2001).
Wikoff et al., "Metabolomics analysis reveals large effects of gut microflora on mammalian blood metabolites," *PNAS*, 106(10):3698-3703 (2009).
Wilson et al., "Human Colonic Biota Studied by Ribosomal DNA Sequence Analysis," *Appl. Environ. Microbiol.*, 62(7):2273-2278 (1996).
Yoon et al., "Treatment of Refractory/Recurrent C. difficile-associated Disease by Donated Stool Transplanted Via Colonoscopy: A Case Series of 12 patients," *J Clin Gastroenterol.*, 44(8):562-566 (2010).
You et al., "Successful treatment of fulminant Clostridium difficile infection with fecal bacteriotherapy," *Ann. Intern. Med.*, 148(8):632-633 (2008).
Yue et al., "Similarity Measure Based on Species Proportions," *Commun. Stat. Theor. Methods*, 34(11):2123-2131 (2005).
Zar et al., "A Comparison of Vancomycin and Metronidazole for the Treatment of Clostridium difficile-Associated Diarrhea, Stratified by Disease Severity," *Clin Infect Dis.*, 45(3):302-307 (2007).
Zilberberg et al., "Clostridium difficile Infections among Hospitalized Children, United States, 1997-2006," *Emerg. Infect. Dis*, 16(4):604-609 (2010).
Zilberberg et al., "Clostridium difficile-related Hospitalizations among US Adults, 2006," *Emerg. Infect. Dis*, 15(1):122-124 (2009).
Zilberberg et al., "Increase in Adult Clostridium difficile-related Hospitalizations and Case-Fatality Rate, United States, 2000-2005," *Emerg. Infect. Dis*, 14(6):929-931 (2008).
Zilberberg et al., "Increase in Clostridium difficile-related Hospitalizations Among Infants in the United States, 2000-2005," *Pediatr Infect Dis J.*, 27(12):1111-1113 (2008).
Zoppi et al., "Oral Bacteriotherapy in Clinical Practice," *Eur. J. Pediatr*, 139(1):18-21 (1982).
Zoppi et al., "Oral Bacteriotherapy in Clinical Practice," *Eur. J. Pediatr*, 139(1):22-24 (1982).
Zoppi et al., "The Intestinal Ecosystem in Chronic Functional Constipation," ACTA Paediatr, Scandinavian University Press, p. 836-841 (1998).
Borody et al., "Treatment of Ulcerative Colitis Using Fecal Bacteriotherapy," *J. Clin. Gastroenterol.*, 37:42-47 (2003).
Crowther, "Transport and Storage of Faeces for Bacteriological Examination," *J. Appl. Bact.*, 34:477-483 (1971).
"Autoimmune Disease List," American Autoimmune Related Diseases Association, pp. 1-4 (2017) <https://www.aarda.org/diseaselist/>.
"Certain infectious and parasitic diseases (A00-B99)," International Statistical Classification of Diseases and Related Health Problems, 10th Revision (ICD-10)-WHO Version, Chapter 1, pp. 1 (2016) <www.apps.who.int/classifications/icd10/browse/2016/en#/I>.
"Spore-Forming Gram-Positive Bacilli: Bacillus and *Clostridium* Species," Jawetz, Melnick, & Adelberg's Medical Microbiology, 26th Edition, Chapter 11, pp. 1-15 (2012).
"Functional Anatomy of Prokaryotic and Eukaryotic Cells," printed Mar. 16, 2017 <http://classes.midlandstech.edu/carterp/courses/bio225/chap04/lecture2.htm>.

Abrams, "Open-Label, Uncontrolled Trial of Bowel Sterilization and Repopulation with Normal Bowel Flora for Treatment of Inflammatory Bowel Disease," Current Therapeutic Research, 58(12):1001-1012 (1997).
Anderson et al., "Systematic review: faecal microbiota transplantation in the management of inflammatory bowel disease," Aliment. Pharmacol. Ther., 36:503-16 (2012).
Andoh et al., "Terminal restriction fragment polymorphisum analyses of fecal microbiota in five siblings including two with ulcerative colitis," Journal of Clinical Gastroenterology, 2:343-345 (2009).
Aroniadis et al., "Intestinal Microbiota and the Efficacy of Fecal Microbiota Transplantation in Gastrointestinal Disease," Gastroenterology and Hepatology, 10(4): 230-7 (2014).
Atarashi et al., "Induction of Colonic Regulatory T Cells by Indigenous *Clostridium* Species," Science, 331(6015):337-341, published online Dec. 23, 2010.
Atarashi et al., "Treg induction by a rationally selected mixture of Clostridia strains from the human microbiota," Nature, 500(7461):232-236 (2013).
Atarashi et al., "WS/PP-064-03 Regulation of colonic regulatory T cells by *Clostridium* species," International Immunology, 22(Suppl 1, Part 3), pp. 1-3 (2010).
Atarashi et al., WS-064 Mucosal immunity: homeostasis, 14th ICIC Abstract book, 14th International Congress of Immunology, pp. iii131-iii133 (2010).
Belkaid et al., "Natural regulatory T cells in infectious disease," Nature Immunology, 6(4):353-360 (2005).
Bolte, "Therapies for Gastrointestinal and Neurological Disorders," U.S. Appl. No. 60/214,813, filed Jun. 28, 2000.
Brandt et al., "Long-Term Follow-Up Study of Fecal Microbiota Transplantation (FMT) for Ulcerative Colitis (UC)," Am. J. Gastroenterol., 107(Suppl 1):S657 (2012).
Browne et al., "Culturing of 'uncultumble' human microbiota reveals novel taxa and extensive sporulation," Nature, 533(7604):543-546 (2016).
Bueche et al., "Quantification of Endospore-Forming Firmicutes by Quantitative PCR with the Functional Gene spo0A," Applied and Environmental Microbiology, 79(17):5302-5312 (2013).
Cammorata et al., "Review article: biofile formation by Helicobacter pylori as a target for eradication of resistant infection," Aliment Pharmacol Ther, 36:222-30 (2012).
Cato et al., "*Clostridium oroticum* comb. nov. amended description," International Journal of Systematic Bacteriology, 17(1):9-13 (1968).
Cherif et al., "Thuricin 7: a novel bacteriocin produced by Bacillus thuringiensis BMG1.7, a new strain isolated from soil," Letters in Applied Microbiology, 32:243-7 (2001).
Choi et al., "Fecal Microbiota Transplantation: Current Applications, Effectiveness, and Future Perspectives," Clin. Endosc., 49:257-265 (2016).
Chu et al., "Profiling Living Bacteria Informs Preparation of Fecal Microbiota Transplantations," PLoS One, 1-16 (2017).
Collins et al., "The Phylogeny of the Genus *Clostridium*: Proposal of Five New Genera and Eleven New Species Combinations," International Journal of Systematic Bacteriology, pp. 812-826 (1994).
Dewhirst et al., "Phylogeny of the Defind Murine Microbiota: Altered Schaedler Flora," Applied and Environmental Microbiology, 65(8):3287-3292 (1999).
Extended European Search Report dated Nov. 30, 2016, in European Patent Application No. 16193790.9.
Frank et al., "Molecular-phylogenetic characterization of microbial community imbalances in human inflammatory bowel diseases," PNAS, 104(34):13780-13785 (2007).
Gaboriau-Routhiau et al., "The Key Role of Segmented Filamentous Bacteria in the Coordinated Maturation of Gut Helper T Cell Responses," Immunity, 31(4):677-689 (2009).
Geuking et al., "Intestinal Bacterial Colonization Induces Mutualistic Regulatory T Cell Respones," Immunity, 34:794-806 (2011).
Gustafsson et al., "The Effect of Faecal Enema on Five Microflora-Associated Characteristics in Patients with Antibiotic-Associated Diarrhoea," Scandinavian Journal of Gastroenterology, 34:580-586 (1999).

(56) References Cited

OTHER PUBLICATIONS

Hayashi et al., "Phylogenetic Analysis of the Human Gut Microbiota Using 16S in rDNA Clone Libraries and Strictly Anaerobic Culture-Based Methods," Microbiol. Immunol., 46(8):535-548 (2002).
Hecker et al., "Fecal Microbiota Transplantation by Freeze-Dried Oral Capsules for Recurrent Clostridium difficile Infection," Open Forum Infect Dis, 3(2): 1-2 (2016).
Honda et al., "Regulation of T Cell Responses by Intestinal Commensal Bacteria," Journal of Intestinal Microbiology, vol. 25, 2nd Edition:104 (2011).
Immunology in the 21st Century: Defeating Infection, Autoimmunity, Allergy, and Cancer, ICI 2010 Wrap-up Report, 14th International Congress of Immunology, pp. 1 (2010).
International Search Report and Written Opinion dated Aug. 8, 2016, in International Application No. PCT/US2016/032695, 10 pgs.
Itoh et al., "Characterization of clostridia isolated from faeces of limited flora mice and their effect on caecal size when associated with germ-free mice," Laboratory Animals, 19:111-118 (1985).
Itoh et al., "Intestinal bacteria antagonistic to Clostridium difficile in mice," Laboratory Animals, 21:20-25 (1987).
Ivanov et al., "Specific Microbiota Direct the Differentiation of IL-17-Producing T-Helper Cells in the Mucosa of the Small Intestine," Cell Host & Microbe, 4:337-349 (2008).
Jacob et al., "Single Delivery of High-Diversity Fecal Microbiota Preparation by Colonoscopy Is Safe and Effective in Increasing Microbial Diversity in Active Ulcerative Colitis," Inflamm Bowel Dis., 0(0):1-9 (2017).
Janeway et al., "Adaptive Immunity to Infection," Immunobiology, 6th Edition, Chapter 10, pp. 414 (2005).
Janeway, Jr. et al., "Autoimmune responses are directed against self antigens," Immunobiology: The Immune System in Health and Disease, 5th Edition, pp. 1-4 (2001).
Kageyama et al., "Phylogenetic and phenotypic evidence for the transfer of Eubacterium aerofaciens to the genus Collinsella as Collinsella aerofaciens gen. nov., comb. nov.," International Journal of Systematic Bacteriology, 49:557-565 (1999).
Kakihana et al., "Fecal microbiota transplantation for patients with steriod-resistant acute graft-versus-host disease of the gut," Blood, 128(16):2083-2088 (2016).
Kang et al., "Microbiota Transfer Therapy alters gut ecosystem and improves gastrointestinal and autism symptoms: an open-label study," Microbiome, 5:10, 16 pages (2017).
Kelly et al., "Commensal gut bacteria: mechanisms of immune modulation," Trends in Immunology, 26(6):326-333 (2005).
Keynan et al., "The Role of Regulatory T Cells in Chronic and Acute Viral Infections," Clinical Infectious Diseases, 46:1046-1052 (2008).
Khanna et al., "A Novel Microbiome Therapeutic Increases Gut Microbial Diversity and Prevents Recurrent Clostridium difficile Infection," The Journal of Infectious Diseases, 214:173-81 (2016).
Klaenhammer, "Bacteriocins of lactic acid bacteria," Biochimie, 70:337-49 (1988).
Koch, "What size should a bacterium be? A question of scale," Annu. Rev. Microbiol., 50:317-48 (1996).
Krogius-Kurikka et al., "Sequence analysis of percent G+C fraction libraries of human faecal bacterial DNA reveals a high number of Antinobacteria," BMC Microbiology, 9(68):1-13 (2009).
Kunde et al., "Safety, Tolerability, and Clinical Response After Fecal Transplantation in Children and Young Adults With Ulcerative Colitis," JPNG, 56(6):597-601 (2013).
Larsen et al., "Gut Microbiota in Human Adults with Type 2 Diabetes Differs from Non-Diabetic Adults," PLoS One, 5(2): e9085-e9095 (2010).
Lau et al., "Bacteraemia caused by Anaerotruncus colihominisand emended description of the species," J Clin Pathol, 59:748-752 (2006).
Lawson et al., "Anaerotruncus colihominis gen. nov., sp. nov., from human faeces," International Journal of Systematic and Evolutionary Microbiology, 54:413-417 (2004).

Lawson et al., "Anaerotruncus," Bergey's Manual of Systematics of Archae and Bacteria, pp. 1-4 (2009).
Louis et al., "Diversity, metabolism and microbial ecology of butyrate-producing bacteria from the human large intestine," FEMS Microbiology Letters, 294:1-8 (2009).
Ludwig et al., "Taxonomic outline of the phylum Firmicutes," Bergey's Manual of Systematic Bacteriology, 3:15-17 (2009).
Maizels et al., "Regulatory T cells in Infection," Advances in Immunology, Chapter 3, 112:73-136 (2011).
Moayyedi et al., "Fecal Microbiota Transplantation Induces Remission in Patients With Active Ulcerative Colitis in a Randomized Controlled Trial," Gastroenterology, 149(1):102-9 (2015).
Momose et al., "16S rRNA gene sequence-based analysis of clostridia related to conversion of germfree mice to the normal state," Journal of Applied Microbiology, 107:2088-2097 (2009).
Niu et al., "Prevalence and Impact of Bacteriophages on the Presence of Escherichia coli O157:H7 in Feedlot Cattle and Their Environment," Applied and Environmental Microbiology, 75(5): 1271-8 (2009).
Office Action dated Sep. 18, 2015, in European Patent Application No. 11 728 077.6.
O'Garra et al., "IL-10—producing and naturally occuring CD4+ Tregs: limiting collateral damage," The Journal of Clinical Investigation, 114:1372-1378 (2004).
Okada et al., "Effects of Fecal Microorganisms and Their Chloroform-Resistant Variants Derived from Mice, Rats, and Humans on Immunological and Physiological Characteristics of the Intestines of Ex-germfree Mice," Infection and Immunity, 62(12):5442-5446 (1994).
Ott et al., "Efficacy of Sterile Fecal Filtrate Transfer for Treating Patients With Clostridium difficile Infection," Gastroenterology, 152(4):799-811 (2017).
Paramsothy et al., "Multidonor intensive faecal microbiota transplantation for active ulcerative colitis: a randomised placebo-controlled trial," The Lancet, published online, 11 pages (2017).
Qiu et al., "Faecalibacterium prausnitzii upregulates regulatory T cells and anti-inflammatory cytokines in treating TNBS-induced colitis," Journal of Crohn's and Colitis, 7:e558-e568 (2013).
Ramesh et al., "Prevention of Clostridium difficile-induced ileocecitis with Bacteriophage," Anaerobe, 5:69-78 (1999).
Response to Office Action filed Feb. 25, 2014, in European Patent Application No. 11 728 077.6.
Response to Office Action filed Jan. 28, 2015, in European Patent Application No. 11 728 077.6.
Response to Office Action filed Nov. 18, 2015, in European Patent Application No. 11 728 077.6.
Roberts, Generation and Development Microbial Drug Products, CSO Vedanta Biosciences, 1st Microbiome Drug Development Summit, pp. 1-17 (2016).
Rossen et al., "Findings From a Randomized Controlled Trial of Fecal Transplantation for Patients with Ulcerative Colitis," Gastroenterology, 149(1):110-8 (2015).
Wells et al., "Clostridia: Sporeforming Anaerobic Bacilli," Medical Microbiology—NCBI Bookshelf, 4th Edition, Chapter 18, pp. 1-20 (1996) <https://www.ncbi.nlm.nih.gov/books/NBK8219/?report=printable>.
Zhou et al., "Total fecal microbiota transplantation alleviates high-fat diet-induced steatohepatitis in mice via beneficial regulation of gut microbiota," Scientific Reports (Nature), 7(1529):1-11 (2017).
Sanchez et al., "The Role of Natural Regulatory T cells in Infection," Immunol Res., 49(0):124-134 (2011).
Sartor, "Therapeutic correction of bacterial dysbiosis discovered by molecular techniques," PNAS, 105(43):16413-16414 (2008).
Sghir et al., "Quantification of Bacterial Groups within Human Fecal Flora by Oligonucleotide Prode Hybridization," Applied and Environmental Microbiology, 66(5):2263-2266 (2000).
Sokol et al., Faecalibacterium prausnitzii is an anti-inflammatory commensal bacterium identified by gut microbiota analysis of Crohn disease patients, Proceedings of the National Academy of Sciences, 105(43):16731-16736 (2008).
Sokol et al., "Low Counts of Faecalibacterium prausnitzii in Colitis Microbiota," Inflamm Bowel Dis., pp. 1-7 (2009).

(56) References Cited

OTHER PUBLICATIONS

Sunil et al., "Design and evaluation of lornoxicam bilayered tablets for biphasic release," Brazilian Journal of Pharmaceutical Sciences, 48(4):609-19 (2012).
Takaishi et al., "Imbalance in intestinal microflora constitution could be involved in the pathogenesis of inflammatory bowel disease," J. Med. Microbiol., 298:463-472 (2008).
Van Andel et al., "Interleukin-12 Has a Role in Mediating Resistance of Murine Strains to Tyzzer's Disease," Infect. Immun 66(10):4942-4946 (1998).
Van Immerseel et al., "Butyric acid-producing anaerobic bacteria as a novel probiotic treatment approach for inflammatory bowel disease," Journal of Medical Microbiology, 59:141-143 (2010).
Vulevic et al., "Modulation of the fecal microflora profile and immune function by a novel trans-galactooligosaccharide mixture (B-GOS) in healthy elderly volunteers," Am J Clin Nutr, 88:1438-46 (2008).
Wachsmann et al., "Characterization of an Orotic Acid Fermenting Bacterium, *Zymobacterium oroticum*, nov. gen., nov. spec.," Journal of Bacteriology, 68(4):400-404 (1954).
Warren et al., "*Clostridium aldenense* sp. nov. and *Clostridium citroniae* sp. nov. Isolated from Human Clinical Infections," Journal of Clinical Microbiology, 44(7):2416-2422 (2006).
Weingarden et al., "Dynamic changes in short- and long-term bacterial composition following fecal microbiota transplantation for recurrent Clostridium difficile infection," Microbiome, 3(10), 8 pages (2015).

\* cited by examiner

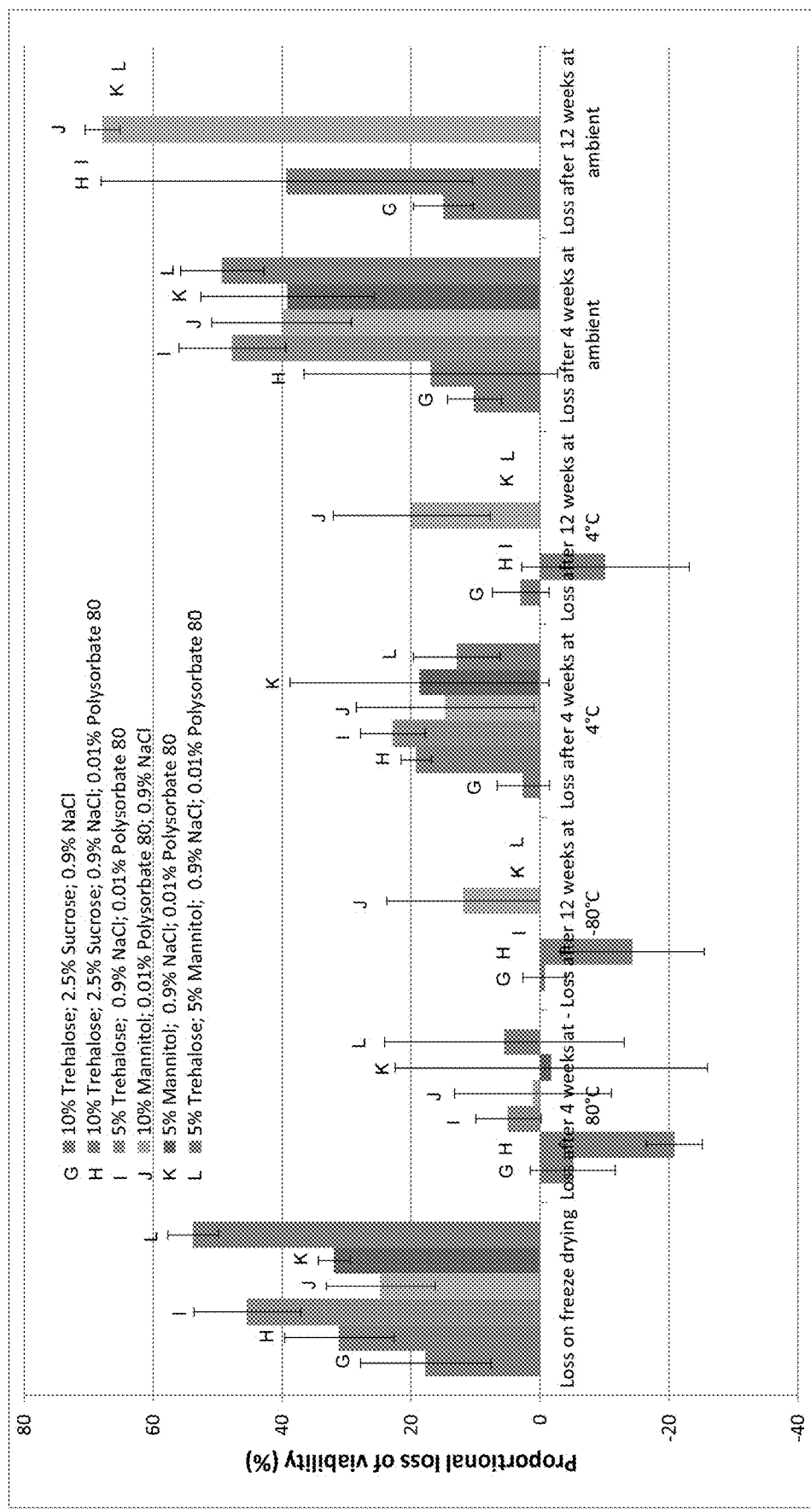

Fig. 3

*Table 1 Viability and counts of FMT samples prior to and after freeze-drying*

| Replicate (Batch #) | % Live Prior to freeze drying | % Live after freeze drying | Absolute % loss on freeze drying | Proportional % loss on freeze drying | Cells/g | Live cells/g |
|---|---|---|---|---|---|---|
| *10% Trehalose; 2.5% Sucrose; 0.9% NaCl* | | | | | | |
| a (DH220714) (R4) | 51.5 | 34.6 | 17.0 | 32.8 | 5.63E+11 | 1.94E+11 |
| b (DH230714) (R4) | 35.4 | 27.7 | 7.7 | 21.8 | 5.29E+11 | 1.47E+11 |
| c (DH14814) (R5) | 50.0 | 50.7 | -0.7 | -1.4 | 3.17E+11 | 1.61E+11 |
| Average (SEM) | 45.6 (5.1) | 37.7 (6.8) | 8.0 (5.1) | 17.7 (10.1) | 4.70E+11 | 1.67E+11 |
| *10% Trehalose; 2.5% Sucrose; 0.9% NaCl; 0.01% Polysorbate 80* | | | | | | |
| a (DH2914) (R6) | 43.8 | 24.8 | 19.0 | 43.4 | 3.96E+11 | 9.82E+10 |
| b (DH3914) (R6) | 49.8 | 42.4 | 7.3 | 14.9 | 3.41E+11 | 1.45E+11 |
| c (DH4914) (R7) | 58.4 | 37.5 | 20.8 | 35.8 | 3.01E+11 | 1.13E+11 |
| Average (SEM) | 50.7 (4.2) | 34.9 (5.2) | 15.7 (4.2) | 31.1 (8.5) | 3.46E+11 | 1.19E+11 |
| *5% Trehalose; 0.9% NaCl; 0.01% Polysorbate 80* | | | | | | |
| a (DH18914) (R7) | 57.3 | 34.0 | 23.4 | 40.7 | 3.37E+11 | 1.14E+11 |
| b (DH131114) (R8) | 45.3 | 36.5 | 8.8 | 19.4 | 6.39E+11 | 2.33E+11 |
| c (DH191114) (R8) | 59.5 | 35.0 | 24.4 | 41.0 | 4.26E+11 | 1.49E+11 |
| d (DH201114) (R9) | 53.7 | 22.0 | 31.7 | 59.0 | 4.13E+11 | 9.08E+10 |
| e (DH211114) (R9) | 53.8 | 17.9 | 36.0 | 66.9 | 3.39E+11 | 6.05E+10 |
| Average (SEM) | 53.9 (2.4) | 29.1 (3.8) | 24.9 (4.6) | 45.4 (8.3) | 4.31E+11 | 1.29E+11 |
| *10% Mannitol; 0.01% Polysorbate 80; 0.9% NaCl* | | | | | | |
| a (DH220714) (R4) | 40.7 | 39.7 | 1.0 | 2.5 | 6.77E+11 | 3.17E+11 |
| b (DH230714) (R4) | 38.0 | 37.0 | 1.0 | 2.6 | 4.62E+11 | 1.71E+11 |
| c (DH14814) (R5) | 36.7 | 26.1 | 10.6 | 28.9 | 1.82E+11 | 1.34E+11 |
| d (DH2914) (R6) | 53.7 | 25.7 | 28.0 | 52.1 | 2.64E+11 | 6.80E+10 |
| e (DH3914) (R6) | 34.2 | 19.6 | 14.5 | 42.7 | 2.46E+11 | 4.83E+10 |
| f (DH4914) (R7) | 38.6 | 31.2 | 7.4 | 19.2 | 2.56E+11 | 7.99E+10 |
| Average (SEM) | 40.3 (2.8) | 29.9 (3.1) | 10.4 (4.1) | 24.7 (8.4) | 3.48E+11 | 1.36E+11 |
| *5% Mannitol; 0.01% Polysorbate 80; 0.9% NaCl* | | | | | | |
| a (DH18914) (R7) | 33.4 | 24.4 | 9.0 | 26.9 | 1.39E+11 | 3.37E+10 |
| b (DH131114) (R8) | 55.7 | 36.3 | 19.5 | 35.0 | 4.81E+11 | 1.74E+11 |
| c (DH191114) (R8) | 62.9 | 41.6 | 21.3 | 33.9 | 4.62E+11 | 1.92E+11 |
| Average (SEM) | 50.7 (8.9) | 34.1 (5.1) | 16.6 (3.8) | 31.9 (2.5) | 3.61E+11 | 1.33E+11 |
| *5% Trehalose; 5% Mannitol; 0.01% Polysorbate 80; 0.9% NaCl* | | | | | | |
| a (DH201114) (R9) | 51.5 | 25.8 | 25.7 | 49.9 | 3.04E+11 | 7.85E+10 |
| b (DH211114) (R9) | 49.2 | 20.8 | 28.4 | 57.7 | 2.47E+11 | 5.14E+10 |
| Average (SEM) | 50.4 (1.2) | 23.3 (2.5) | 27.1 (1.4) | 53.8 (3.9) | 2.76E+11 | 6.50E+10 |

Fig. 4

*Table 2 Water activity of freeze-dried FMT samples*

| Replicate (Batch #) | Water activity |
|---|---|
| 10% Trehalose; 2.5% Sucrose; 0.9% NaCl | |
| a (DH220714) (R4) | 0.143 |
| b (DH230714) (R4) | 0.162 |
| c (DH14814) (R5) | 0.153 |
| Average | 0.153 |
| 10% Trehalose; 2.5% Sucrose; 0.9% NaCl; 0.01% Polysorbate 80 | |
| a (DH2914) (R6) | 0.093 |
| b (DH3914) (R6) | 0.071 |
| c (DH4914) (R7) | 0.105 |
| Average | 0.090 |
| 5% Trehalose; 0.9% NaCl; 0.01% Polysorbate 80 | |
| a (DH18914) (R7) | 0.228 |
| b (DH131114) (R8) | 0.217 |
| c (DH191114) (R8) | 0.267 |
| d (DH201114) (R9) | 0.259 |
| e (DH211114) (R9) | 0.335 |
| Average | 0.261 |
| 10% Mannitol; 0.01% Polysorbate 80; 0.9% NaCl | |
| a (DH220714) (R4) | 0.214 |
| b (DH230714) (R4) | 0.157 |
| c (DH14814) (R5) | 0.248 |
| d (DH2914) (R6) | 0.045 |
| e (DH3914) (R6) | 0.167 |
| f (DH4914) (R7) | 0.101 |
| Average | 0.155 |
| 5% Mannitol; 0.01% Polysorbate 80; 0.9% NaCl | |
| a (DH18914) (R7) | 0.179 |
| b (DH131114) (R8) | 0.269 |
| c (DH191114) (R8) | 0.454 |
| Average | 0.301 |
| 5% Trehalose; 5% Mannitol; 0.01% Polysorbate 80; 0.9% NaCl | |
| a (DH201114) (R9) | 0.235 |
| b (DH211114) (R9) | 0.250 |
| Average | 0.243 |

Fig. 5

*Table 3 Viability of freeze-dried samples after 4 weeks of storage*

| Replicate (Batch #) | Storage temperature | % Live | Absolute % loss of viability | Proportional % loss of viability |
|---|---|---|---|---|
| *10% Trehalose; 2.5% Sucrose; 0.9% NaCl* | | | | |
| a (DH220714) (R4) (Initial 34.6% viable) | Ambient | 33.3 | 1.3 | 3.8 |
| | 4°C | 36.2 | -1.6 | -4.6 |
| | -80°C | 38.3 | -3.7 | -10.7 |
| b (DH230714) (R4) (Initial 27.7% viable) | Ambient | 25.3 | 2.4 | 8.7 |
| | 4°C | 26.9 | 0.8 | 2.9 |
| | -80°C | 31.2 | -3.5 | -12.6 |
| c (DH14814) (R5) (Initial 50.7% viable) | Ambient | 41.6 | 9.1 | 18.0 |
| | 4°C | 45.9 | 4.8 | 9.5 |
| | -80°C | 46.6 | 4.1 | 8.1 |
| Average (SEM) | Ambient | 33.4 (4.7) | 4.3 (2.4) | 10.2 (4.2) |
| | 4°C | 36.3 (5.5) | 1.3 (1.9) | 2.6 (4.1) |
| | -80°C | 38.7 (4.5) | -1.0 (2.6) | -5.1 (6.6) |
| *10% Trehalose; 2.5% Sucrose; 0.9% NaCl; 0.01% Polysorbate 80* | | | | |
| a (DH2914) (R6) (Initial 24.8% viable) | Ambient | 20.1 | 4.7 | 18.8 |
| | 4°C | 29.7 | -4.9 | -19.9 |
| | -80°C | 30.7 | -6.0 | -24.0 |
| b (DH3914) (R6) (Initial 42.4% viable) | Ambient | 35.9 | 12.9 | 50.2 |
| | 4°C | 42.3 | -3.8 | -14.9 |
| | -80°C | 42.1 | -3.2 | -12.3 |
| c (DH4914) (R7) (Initial 37.5% viable) | Ambient | 44.3 | -6.8 | -18.0 |
| | 4°C | 46.1 | -8.6 | -22.9 |
| | -80°C | 47.3 | -9.8 | -26.1 |
| Average (SEM) | Ambient | 33.4 (7.1) | 3.6 (5.7) | 17.0 (19.7) |
| | 4°C | 39.4 (5.0) | -5.8 (1.5) | 19.2 (2.3) |
| | -80°C | 40.0 (4.9) | -6.3 (1.9) | -20.8 (4.3) |
| *5% Trehalose; 0.9% NaCl; 0.01% Polysorbate 80* | | | | |
| a (DH18914) (R7) (Initial 34.0% viable) | Ambient | 31.3 | 12.3 | 36.2 |
| | 4°C | 43.6 | 9.3 | 27.4 |
| | -80°C | 42.8 | 5.2 | 15.4 |
| b (DH131114) (R8) (Initial 36.5% viable) | Ambient | 10.1 | 26.4 | 72.3 |
| | 4°C | 18.8 | 17.7 | 48.6 |
| | -80°C | 22.5 | 14.0 | 38.3 |
| c (DH191114) (R8) (Initial 35.0% viable) | Ambient | 14.1 | 20.9 | 59.8 |
| | 4°C | 19.7 | 15.3 | 43.7 |
| | -80°C | 25.2 | 9.8 | 28.0 |
| d (DH201114) (R9) (Initial 22.0 % viable) | Ambient | 11.3 | 10.7 | 48.7 |
| | 4°C | 21.0 | 1.0 | 4.4 |
| | -80°C | 25.6 | -3.6 | -16.4 |
| e (DH211114) (R9) (Initial 17.9 % viable) | Ambient | 14.2 | 3.8 | 21.3 |
| | 4°C | 21.0 | -1.8 | -10.0 |
| | -80°C | 24.9 | -7.3 | -40.8 |
| Average | Ambient | 16.2 (5.0) | 14.8 (3.2) | 47.7 (8.2) |
| | 4°C | 24.8 (6.3) | 8.3 (1.9) | 22.8 (5.0) |
| | -80°C | 28.2 (4.9) | 3.6 (2.0) | 4.9 (5.1) |

Fig. 6

*Table 3 Viability of freeze-dried samples after 4 weeks of storage (continued)*

| Replicate (Batch #) | Storage temperature | % Live | Absolute % loss of viability | Proportional % loss of viability |
|---|---|---|---|---|
| 10% Mannitol; 0.01% Polysorbate 80; 0.9% NaCl | | | | |
| a (DH220714) (R4) (Initial 39.7% viable) | Ambient | 21.1 | 18.6 | 46.9 |
| | 4°C | 31.2 | 8.5 | 21.4 |
| | -80°C | 39.3 | 0.4 | 1.0 |
| b (DH230714) (R4) (Initial 37.0% viable) | Ambient | 18.3 | 18.7 | 50.5 |
| | 4°C | 20.3 | 16.7 | 45.1 |
| | -80°C | 38.3 | -1.3 | -3.5 |
| c (DH14814) (R5) (Initial 26.1% viable) | Ambient | 8.9 | 17.2 | 65.6 |
| | 4°C | 12.1 | 14.0 | 53.7 |
| | -80°C | 11.9 | 14.2 | 54.4 |
| d (DH2914) (R6) (Initial 25.7% viable) | Ambient | 12.8 | 6.5 | 15.3 |
| | 4°C | 29.6 | 0.2 | 0.4 |
| | -80°C | 38.9 | 0.3 | 0.7 |
| e (DH3914) (R6) (Initial 19.6% viable) | Ambient | 7.3 | 12.3 | 62.7 |
| | 4°C | 18.3 | 1.4 | 6.9 |
| | -80°C | 21.4 | -1.8 | -9.0 |
| f (DH4914) (R7) (Initial 31.2% viable) | Ambient | 12.7 | -0.1 | -0.4 |
| | 4°C | 18.0 | -12.4 | -39.6 |
| | -80°C | 20.8 | -11.6 | -37.2 |
| Average (SEM) | Ambient | 13.5 (2.2) | 12.2 (3.1) | 40.1 (10.9) |
| | 4°C | 21.6 (3.0) | 4.7 (4.4) | 14.7 (13.8) |
| | -80°C | 28.4 (4.9) | 0.0 (3.4) | 1.1 (12.2) |
| 5% Mannitol; 0.9% NaCl; 0.01% Polysorbate 80 | | | | |
| a (DH18914) (R7) (Initial 24.4% viable) | Ambient | 17.2 | 7.2 | 29.7 |
| | 4°C | 18.4 | 6.0 | 24.6 |
| | -80°C | 27.8 | -3.4 | -14.1 |
| b (DH131114) (R8) (Initial 36.3% viable) | Ambient | 28.3 | 8.0 | 22.0 |
| | 4°C | 43.0 | -6.7 | -18.6 |
| | -80°C | 49.4 | -13.1 | -36.1 |
| c (DH191114) (R8) (Initial 41.6% viable) | Ambient | 14.3 | 27.3 | 65.7 |
| | 4°C | 20.7 | 20.9 | 50.1 |
| | -80°C | 22.9 | 18.7 | 45.0 |
| Average | Ambient | 19.9 (4.3) | 14.2 (6.6) | 39.1 (13.5) |
| | 4°C | 27.4 (7.8) | 6.7 (8.0) | 18.7 (20.1) |
| | -80°C | 33.4 (8.1) | 0.7 (9.4) | -1.7 (24.2) |
| 5% Trehalose; 5% Mannitol; 0.9% NaCl; 0.01% Polysorbate 80 | | | | |
| a (DH201114) (R9) (Initial 25.8 % viable) | Ambient | 11.4 | 14.4 | 55.7 |
| | 4°C | 20.7 | 5.1 | 19.6 |
| | -80°C | 19.6 | 6.2 | 24.0 |
| b (DH211114) (R9) (Initial 20.8 % viable) | Ambient | 11.9 | 8.9 | 42.9 |
| | 4°C | 19.5 | 1.3 | 6.2 |
| | -80°C | 23.5 | -2.7 | -13.1 |
| Average | Ambient | 11.7 (0.3) | 11.7 (2.8) | 49.3 (6.4) |
| | 4°C | 20.1 (0.6) | 3.2 (1.9) | 12.9 (6.7) |
| | -80°C | 21.6 (2.0) | 1.8 (4.5) | 5.5 (18.6) |

Fig. 7

*Table 4 Viability of freeze-dried samples after 12 weeks of storage*

| Replicate (Batch #) | Storage temperature | % Live | Absolute % loss of viability | Proportional % loss of viability |
|---|---|---|---|---|
| 10% Trehalose; 2.5% Sucrose; 0.9% NaCl | | | | |
| a (DH220714) (R4) (Initial 34.6% viable) | Ambient | 32.5 | 2.1 | 6.1 |
| | 4°C | 36.2 | -1.6 | -4.6 |
| | -80°C | 36.1 | -1.5 | -4.3 |
| b (DH230714) (R4) (Initial 27.7% viable) | Ambient | 21.7 | 6 | 21.7 |
| | 4°C | 24.7 | 3 | 10.8 |
| | -80°C | 28.8 | -1.1 | -4.0 |
| c (DH14814) (R5) (Initial 50.7% viable) | Ambient | 41.9 | 8.8 | 17.3 |
| | 4°C | 49.3 | 1.4 | 2.8 |
| | -80°C | 47.6 | 3.1 | 6.1 |
| Average (SEM) | Ambient | 32.0 (5.8) | 5.6 (1.9) | 15.0 (4.6) |
| | 4°C | 36.7 (7.1) | 0.9 (1.3) | 3.0 (4.4) |
| | -80°C | 37.5 (5.5) | 0.2 (1.5) | -0.7 (3.4) |
| 10% Trehalose; 2.5% Sucrose; 0.9% NaCl; 0.01% Polysorbate 80 | | | | |
| a (DH2914) (R6) (Initial 24.8% viable) | Ambient | 6.2 | 18.6 | 75.0 |
| | 4°C | 22.6 | 2.2 | 9.0 |
| | -80°C | 25.3 | -0.5 | -1.9 |
| b (DH3914) (R6) (Initial 42.4% viable) | Ambient | 13.9 | 15.6 | 60.5 |
| | 4°C | 40.6 | -1.1 | -4.3 |
| | -80°C | 41.0 | -1.1 | -4.4 |
| c (DH4914) (R7) (Initial 37.5% viable) | Ambient | 44.1 | -6.6 | -17.7 |
| | 4°C | 50.6 | -13.1 | -34.9 |
| | -80°C | 51.2 | -13.7 | -36.5 |
| Average (SEM) | Ambient | 21.4 (11.6) | 9.2 (7.9) | 39.3 (28.8) |
| | 4°C | 37.9 (8.2) | -4.0 (4.6) | -10.1 (13.0) |
| | -80°C | 39.2 (7.5) | -5.1 (4.3) | -14.3 (11.1) |
| 5% Trehalose; 0.9% NaCl; 0.01% Polysorbate 80 | | | | |
| a (DH18914) (R7) (Initial 34.0% viable) | Ambient | 27.9 | 6.1 | 17.8 |
| | 4°C | 39.1 | -5.1 | -15.0 |
| | -80°C | 42.4 | -8.4 | -24.8 |
| b (DH131114) (R8) (Initial 36.5% viable) | Ambient | Pending | Pending | Pending |
| | 4°C | Pending | Pending | Pending |
| | -80°C | Pending | Pending | Pending |
| c (DH191114) (R8) (Initial 35.0% viable) | Ambient | Pending | Pending | Pending |
| | 4°C | Pending | Pending | Pending |
| | -80°C | Pending | Pending | Pending |
| d (DH201114) (R9) (Initial 22.0 % viable) | Ambient | Pending | Pending | Pending |
| | 4°C | Pending | Pending | Pending |
| | -80°C | Pending | Pending | Pending |
| e (DH211114) (R9) (Initial 17.9 % viable) | Ambient | Pending | Pending | Pending |
| | 4°C | Pending | Pending | Pending |
| | -80°C | Pending | Pending | Pending |
| Average | Ambient | Pending | Pending | Pending |
| | 4°C | Pending | Pending | Pending |
| | -80°C | Pending | Pending | Pending |

Fig. 8

*Table 4 Viability of freeze-dried samples after 12 weeks of storage (continued)*

| Replicate (Batch #) | Storage temperature | % Live | Absolute % loss of viability | Proportional % loss of viability |
|---|---|---|---|---|
| 10% Mannitol; 0.01% Polysorbate 80; 0.9% NaCl | | | | |
| a (DH220714) (R4) (Initial 39.7% viable) | Ambient | 14.9 | 24.8 | 62.5 |
| | 4°C | 30.5 | 9.2 | 23.2 |
| | -80°C | 30.9 | 8.8 | 22.2 |
| b (DH230714) (R4) (Initial 37.0% viable) | Ambient | 8.5 | 28.5 | 77.0 |
| | 4°C | 30.4 | 6.6 | 17.8 |
| | -80°C | 37.9 | -0.9 | -2.4 |
| c (DH14814) (R5) (Initial 26.1% viable) | Ambient | 6.4 | 19.7 | 75.5 |
| | 4°C | 14.1 | 12.0 | 46.1 |
| | -80°C | 15.2 | 10.9 | 41.8 |
| d (DH2914) (R6) (Initial 25.7% viable) | Ambient | 10.2 | 28.5 | 67.2 |
| | 4°C | 26.8 | 1.9 | 4.4 |
| | -80°C | 26.9 | 1.4 | 3.4 |
| e (DH3914) (R6) (Initial 19.6% viable) | Ambient | 7.7 | 11.9 | 60.8 |
| | 4°C | 25.0 | -5.3 | -27.0 |
| | -80°C | 18.8 | 0.8 | 4.2 |
| f (DH4914) (R7) (Initial 31.2% viable) | Ambient | 11.4 | 19.8 | 63.5 |
| | 4°C | 14.0 | 17.2 | 55.1 |
| | -80°C | 30.6 | 0.6 | 1.9 |
| Average | Ambient | 9.9 (1.2) | 22.2 (2.6) | 67.8 (2.8) |
| | 4°C | 23.5 (3.1) | 6.9 (3.2) | 19.9 (12.1) |
| | -80°C | 26.7 (3.4) | 3.6 (2.0) | 11.9 (6.9) |
| 5% Mannitol; 0.9% NaCl; 0.01% Polysorbate 80 | | | | |
| a (DH18914) (R7) (Initial 24.4% viable) | Ambient | 13.6 | 10.8 | 44.2 |
| | 4°C | 30.9 | -6.5 | -26.5 |
| | -80°C | 22.8 | 1.6 | 6.7 |
| b (DH131114) (R8) (Initial 36.3% viable) | Ambient | Pending | Pending | Pending |
| | 4°C | Pending | Pending | Pending |
| | -80°C | Pending | Pending | Pending |
| c (DH191114) (R8) (Initial 41.6% viable) | Ambient | Pending | Pending | Pending |
| | 4°C | Pending | Pending | Pending |
| | -80°C | Pending | Pending | Pending |
| Average | Ambient | Pending | Pending | Pending |
| | 4°C | Pending | Pending | Pending |
| | -80°C | Pending | Pending | Pending |
| 5% Trehalose; 5% Mannitol; 0.9% NaCl; 0.01% Polysorbate 80 | | | | |
| a (DH201114) (R9) (Initial 25.8 % viable) | Ambient | Pending | Pending | Pending |
| | 4°C | Pending | Pending | Pending |
| | -80°C | Pending | Pending | Pending |
| b (DH211114) (R9) (Initial 20.8 % viable) | Ambient | Pending | Pending | Pending |
| | 4°C | Pending | Pending | Pending |
| | -80°C | Pending | Pending | Pending |
| Average | Ambient | Pending | Pending | Pending |
| | 4°C | Pending | Pending | Pending |
| | -80°C | Pending | Pending | Pending |

COMPOSITIONS FOR FECAL FLORAL TRANSPLANTATION AND METHODS FOR MAKING AND USING THEM AND DEVICE FOR DELIVERING THEM

CROSS-REFERENCE TO RELATED APPLICATIONS

This application is a continuation of U.S. patent application Ser. No. 15/887,651, filed Feb. 2, 2018, which is a continuation of U.S. patent application Ser. No. 15/155,628, filed May 16, 2016 (now U.S. Pat. No. 9,901,603, issued Feb. 27, 2018), which claims priority to U.S. Provisional Patent Application No. 62/161,826, filed May 14, 2015, all of which are incorporated by reference in their entireties herein.

TECHNICAL FIELD

This invention generally relates to medicine and gastroenterology, pharmacology and microbiology. In alternative embodiments, provided are compositions, e.g., formulations, used for gastric, gastrointestinal and/or colonic treatments or lavage, e.g., orthostatic lavage, e.g., for inducing the purgation (e.g., cleansing) of a gastrointestinal (GI) tract, including a colon; and methods for making, storing and using them, including storage, including long term storage. In alternative embodiments, compositions provided herein are used for the stabilization, amelioration, treatment and/or prevention of constipation, for the treatment of abdominal pain, particularly non-specific abdominal pain, and diarrhea, including diarrhea caused by a drug side effect, a psychological condition, a disease or a condition such as autism, Crohn's Disease, a poison, a toxin or an infection, e.g., a toxin-mediated traveler's diarrhea, or *C. difficile* or the pseudo-membranous colitis associated with this infection. In alternative embodiments, pharmaceuticals and products (articles) of manufacture provided herein are delivered to an individual, e.g., a human or an animal, in need thereof.

BACKGROUND

Implantation or administration of human colonic microbiota into the bowel of a sick patient is called Fecal Microbiota Transplantation (FMT). It is a therapeutic process originally designed to treat *Clostridium difficile* infection (CDI). It entails infusions through a colonoscope, an enema or via a nasojejunal tube of human microbiota either in the form of homogenized stool, extracts of homogenized stool, or cultured stool components such as *Clostridia*, to implant in the colon and so displace or eradicate the pathogenic *Clostridium difficile*; and it has a high success rate. In treating *C. difficile* infection, FMT is a highly efficacious treatment which carries well over a 90% cure rate with a single infusion and higher rate with multiple infusions. Hence, FMT can be life-saving given the current CDI mortality in the US of some 30,000 persons/year. This therapeutic process has also been used in treating other gut infective agents such as *E. coli* and Vancomycin resistant *Enterococci* (VRE).

There is growing demand for FMT primarily for the treatment of CDI. However, use of the therapy is restricted by the logistics of obtaining fresh FMT material from pre-screened donors in a timely fashion. Access to pre-prepared FMT material, stored frozen or lyophilized, would improve access to the therapy.

SUMMARY

In one embodiment, provided herein is a pharmaceutical composition comprising a fecal microbiota preparation in a lyophilized formulation, wherein after at least 12 weeks of storage at ambient temperature or lower the fecal microbiota preparation is capable of maintaining at least 60% cell viability relative to the initial cell viability at the start of the storage.

In one embodiment, provided herein is an oral pharmaceutical composition comprising a non-selective fecal microbiota preparation in a lyophilized formulation, wherein, after at least 12 weeks of storage at ambient temperature or lower, the fecal microbiota preparation is capable of maintaining about 60% to about 80% cell viability relative to the initial cell viability prior to storage, and is effective for treating one or more disorders or conditions selected from the group consisting of recurrent or primary *C. diff* infection, autism spectrum disorder (ASD), ulcerative colitis, Crohn's disease, and irritable bowel syndrome.

In one embodiment, provided herein is a method for storing a pharmaceutical composition, where the method comprising: obtaining a pharmaceutical composition comprising a fecal microbiota preparation in a lyophilized formulation, storing the pharmaceutical composition at ambient temperature or lower, wherein after at least 12 weeks of storage the fecal microbiota preparation is capable of maintaining at least 60% cell viability relative to the initial cell viability immediately prior to storage.

The details of one or more embodiments of the invention are set forth in the accompanying drawings and the description below. Other features, objects, and advantages of the invention will be apparent from the description and drawings, and from the claims.

All publications, patents, patent applications cited herein (including, but not limited to, U.S. Pat. Nos. 6,645,530, 8,460,648, 8,906,668, 9,011,834, WO 2012/016287, WO 2014/078911, WO 2014/176632, WO 2012/122478, WO 2014/152484, WO 2011/094027, WO 2013/053836, WO 2015/006355, WO 2013/080561, WO 2011/046616, WO 2011/152566, U.S. Pat. No. 2014/0363398, US 2014/0363397) are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

FIG. 2 graphically illustrates the overall proportional losses for six exemplary formulations, as discussed in Example 2, below.

FIG. 3 illustrates Table 1, as discussed in Example 2, below.

FIG. 4 illustrates Table 2, as discussed in Example 2, below.

FIG. 5 and FIG. 6 illustrate Table 3, as discussed in Example 2, below.

FIG. 7 and FIG. 8 illustrate Table 4, as discussed in Example 2, below.

Like reference symbols in the various drawings indicate like elements. Reference will now be made in detail to various exemplary embodiments of the invention, examples of which are illustrated in the accompanying drawings. The following detailed description is provided to give the reader a better understanding of certain details of embodiments and embodiments of the invention, and should not be interpreted as a limitation on the scope of the invention.

DETAILED DESCRIPTION

Figure 1:
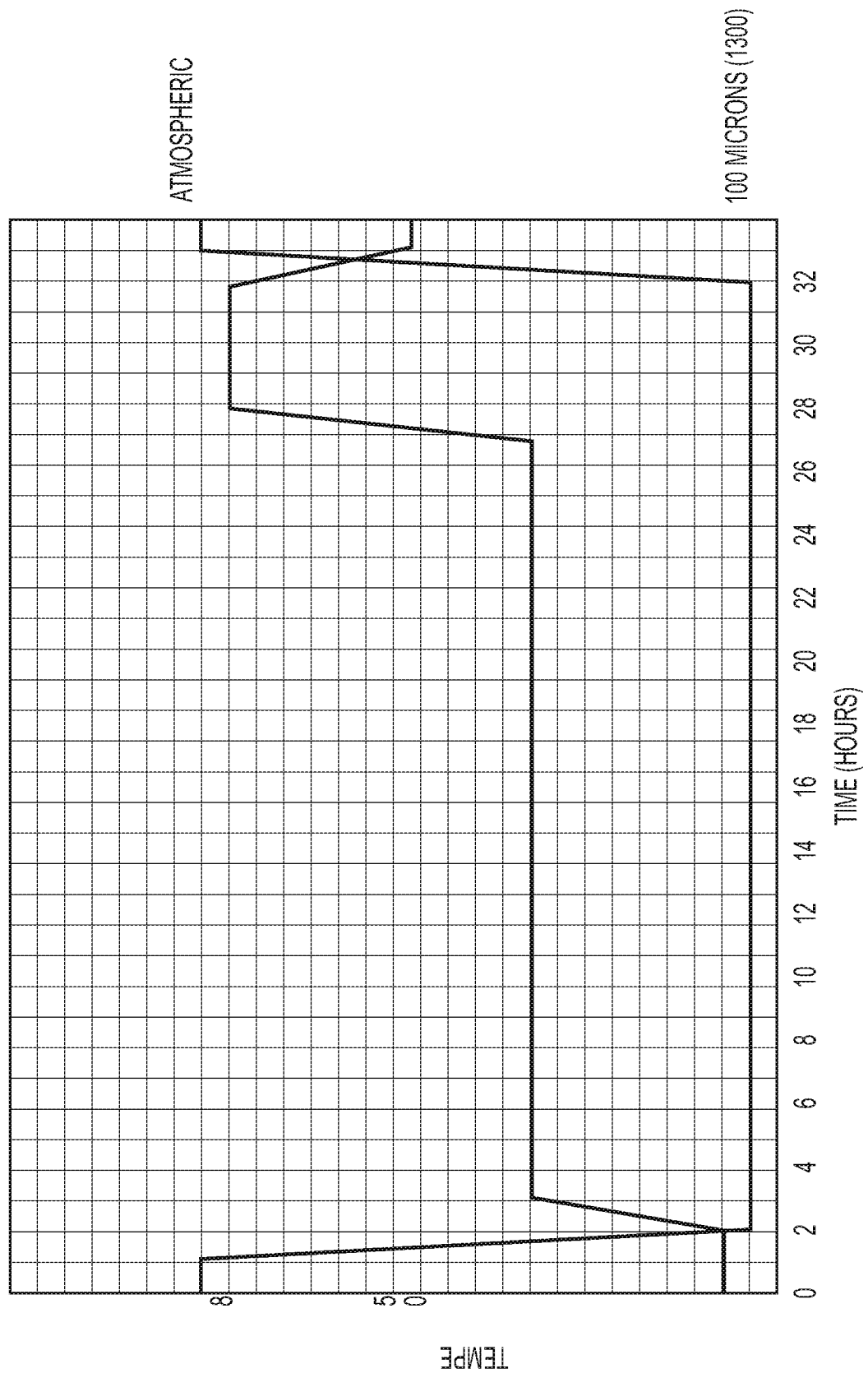
FIG. 1 graphically illustrates changes in shelf temperature Stage 3, Secondary Drying of the exemplary lyophilization of FIG. 1.

As used herein, "lyophilization" or "freeze drying" refers to the process of drying a material by first freezing it and then encouraging the ice within it to sublimate in a vacuum environment.

As used herein, a "cryoprotectant" refers to a substance that is added to a formulation in order to protect an active ingredient during freezing.

As used herein, a "lyoprotectant" refers to a substance that is added to a formulation in order to protect an active ingredient during the drying stage of a Lyophilization (also known as freeze-drying) process.

As used herein, the term "ambient tempeature" refers to the temperature of the surrounding environment, and more specifically, the temperature of the surrounding air. The term "room tempeature" refers to the indoor temperature of a temperature-controlled building, which is approximately between 15° C. (59° F.) and 22° C. (72° F.).

As used herein, a "microbiota" and "flora" refer to a community of microbes that live in or on a subject's body, both sustainably and transiently, including eukaryotes, archaea, bacteria, and viruses (including bacterial viruses (i.e., phage)). A "fecal microbiota" or "fecal microbiota preparation" refers to a community of microbes present in a subject's feces. A non-selective fecal microbiota refers to a community or mixture of fecal microbes derived from a donor's fecal sample without selection and substantially resembling microbial constituents and population structure found in such fecal sample.

As used herein, "colony forming units" (cfu) refers to an estimate of the number of viable microorganism cells in a given sample.

As used herein, "viable" means possessing the ability to multiply. Here, the viability of bacterial populations is monitored as a function of the membrane integrity of the cell. Cells with a compromised membrane are considered to be dead or dying, whereas cells with an intact membrane are considered live.

As used herein, "isolated" or "purified" refers to a bacterium or other entity or substance that has been (1) separated from at least some of the components with which it was associated when initially produced (whether in nature or in an experimental setting), and/or (2) produced, prepared, purified, and/or manufactured by the hand of man. Isolated or purified bacteria can be separated from at least about 10%, about 20%, about 30%, about 40%, about 50%, about 60%, about 70%, about 80%, about 90%, or more of the other components with which they were initially associated.

As used herein, the terms "pathogen" and "pathogenic" in reference to a bacterium or any other organism or entity includes any such organism or entity that is capable of causing or affecting a disease, disorder or condition of a host organism containing the organism or entity.

As used herein, "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Spore-formers" or bacteria "capable of forming spores" are those bacteria containing the genes and other necessary abilities to produce spores under suitable environmental conditions.

As used herein, "subject" refers to any animal subject including humans, laboratory animals (e.g., primates, rats, mice), livestock (e.g., cows, sheep, goats, pigs, turkeys, chickens), and household pets (e.g., dogs, cats, rodents, etc.). The subject or patient may be healthy, or may be suffering from an infection due to a gastrointestinal pathogen or may be at risk of developing or transmitting to others an infection due to a gastrointestinal pathogen.

As used herein, "Shannon Diversity Index" refers to a diversity index that accounts for abundance and evenness of species present in a given community using the formula $$H = -\sum_{i=1}^{R} p_i \ln p_i,$$

where H is Shannon Diversity Index, R is the total number of species in the community, and $p_i$ is the proportion of R made up of the ith species. Higher values indicate diverse and equally distributed communities, and a value of 0 indicates only one species is present in a given community. For further reference, see Shannon and Weaver, (1949) *The mathematical theory of communication*. The University of Illinois Press, Urbana. 117 pp.

As used herein, "antibiotic" refers to a substance that is used to treat and/or prevent bacterial infection by killing bacteria, inhibiting the growth of bacteria, or reducing the viability of bacteria.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures.

As used herein, "therapeutically effective amount" or "pharmaceutically active dose" refers to an amount of a composition which is effective in treating the named disease, disorder or condition.

In one embodiment, provided herein is a pharmaceutical composition comprising a fecal microbiota preparation in a formulation, wherein after at least 12 weeks of storage at ambient temperature or lower, the fecal microbiota preparation is capable of maintaining at least 60% cell viability relative to the initial cell viability at the start of the storage. In another embodiment, a fecal microbiota preparation is in a lyophilized formulation.

In one embodiment, a fecal microbiota preparation is in a lyophilized formulation that, after at least 2, 4, 8, 12, 16, or 20 weeks of storage at ambient temperature or lower, is capable of maintaining at least about 40%, 45%, 50%, 55%, 60%, 65%, 70%, 75%, 80%, 85%, 90%, 95%, 98%, or 99% cell viability relative to the initial cell viability immediately prior to storage.

In one embodiment, after at least 8, 12, 16, 20, 50, 75, 100, 150, or 200 weeks of storage at ambient temperature or lower, a lyophilized fecal microbiota preparation maintains at least 50% cell viability relative to the initial cell viability immediately prior to storage. In one embodiment, after at least 12 weeks of storage at ambient temperature or lower, a lyophilized fecal microbiota preparation maintains between 30% and 90%, between 40% and 90%, between 50% and 90%, between 60% and 90%, between 70% and 90%, between 80% and 90%, between 40% and 80%, between 50% and 70%, between 55% and 65%, between 30% and 40%, between 40% and 50%, between 50% and 60%, between 60% and 70%, or between 70% and 80% cell viability relative to the initial cell viability immediately prior to storage.

In one embodiment, a fecal microbiota preparation comprises a donor's entire or substantially complete microbiota. In one embodiment, a fecal microbiota preparation comprises a non-selective fecal microbiota. In another embodiment, a fecal microbiota preparation comprises an isolated or purified population of live non-pathogenic fecal bacteria. In a further embodiment, a fecal microbiota preparation comprises a non-selective and substantially complete fecal microbiota preparation from a single donor.

In one embodiment, bacterial cell viability is measured by using imaging assays that measure membrane permeability. A combination of membrane permeant and impermeant DNA dyes stains are used (e.g., intact cells stained green and dead cells stained red). In one embodiment, SYTO 9 and propidium idodide are used to stain and differentiate live and dead bacteria. See Stocks, *Cytometry A.* 2004 Oct; 61(2): 189-95. In another embodiment, live cell determination is combined with fluorescent Gram staining. In another embodiment, the number of viable bacterial cells in a sample is assessed by a colorimetric method, e.g., a Dojindo's Microbial Viability Assay Kit-WST.

In one embodiment, bacterial cell viability is assessed by counting the number of colonies on an agar plate is the standard method for determining the number of viable bacterial cells in samples. In another embodiment, cell viability is evaluated via molecular viability analyses, e.g., a PCR-based approach, which can differentiate nucleic acids associated with viable cells from those associated with inactivated cells. See Cangelosi and Mescheke, *Appl Environ Microbiol.* 2014 October; 80(19): 5884-5891.

In one embodiment, a therapeutic composition comprises a cryoprotectant. In another embodiment, a cryoprotectant comprises, consisting essentially or, or consisting of polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

In another embodiment, a therapeutic composition comprises a lyoprotectant. In one embodiment, the same substance or the same substance combination is used as both a cryoprotectant and a lyoprotectant. Exemplary lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In one embodiment, a lyoprotectant is a non-reducing sugar, such as trehalose or sucrose. In one embodiment, a cryoprotectant or a lyoprotectant consisting essentially of, or consisting of, one or more substances mentioned in this paragraph and the paragraph above.

In one aspect, a cryoprotectant or a lyoprotectant comprise an intracellular agent, e.g., DMSO, Glycerol, or PEG, which penetrates inside the cell preventing the formation of ice crystals that could result in membrane rupture. In another aspect, a cryoprotectant or a lyoprotectant comprise an extracellular agent, e.g., sucrose, trehalose, or dextrose, which does not penetrate in cell membrane and act to improve the osmotic imbalance that occurs during freezing.

In one embodiment, a lyophilized formulation comprises trehalose. In one embodiment, a lyophilized formulation comprises 2% to 30%, 3% to 25%, 4% to 20%, 5% to 15%, 6% to 10%, 2% to 30%, 2% to 25%, 2% to 20%, 2% to 15%, or 2% to 10% trehalose. In one embodiment, a lyophilized formulation comprises at least 2%, 3%, 4%, 5%, 6%, 7%, 8%, 9%, 10%, or 15% trehalose. In one embodiment, a lyophilized formulation comprises at most 2%, 3%, 4%, 5%, 6%, 7%, 8%, 9%, 10%, or 15% trehalose. In one embodiment, a lyophilized formulation comprises about 5% trehalose. In one embodiment, a lyophilized formulation comprises trehalose and sucrose. In one embodiment, a lyophilized formulation comprises between about 8% to 12% trehalose with between about 1.5% to 3.5% sucrose and between about 0.5% to 1.5% NaCl.

In one embodiment, the preparation of a fecal microbiota preparation involves a treatment selected from the group consisting of ethanol treatment, detergent treatment, heat treatment, irradiation, and sonication, or a combination thereof. In one embodiment, the preparation of a fecal microbiota preparation involves no treatment selected from the group consisting of ethanol treatment, detergent treatment, heat treatment, irradiation, and sonication. In one embodiment, the preparation of a fecal microbiota preparation involves a separation step selected from the group consisting of filtering, sieving, density gradients, filtration, chromatography, and a combination thereof. In one embodiment, the preparation of a fecal microbiota preparation does not require one or more separation steps selected from the group consisting of filtering, sieving, density gradients, filtration, and chromatography. In one embodiment, a fecal microbiota preparation is substantially free of non-living matter. In one embodiment, a fecal microbiota preparation is substantially free of acellular material selected from the group consisting of residual fiber, DNA, viral coat material, and non-viable material. In one embodiment, a fecal microbiota preparation is substantially free of eukaryotic cells from the fecal microbiota's donor.

In one embodiment, a pharmaceutical composition provided here, after at least 12 weeks of storage at ambient temperature or lower, is effective for treating one or more disorders selected from the group consisting of recurrent or primary *C. diff.* infection, autism spectrum disorder (ASD), ulcerative colitis, Crohn's disease, and irritable bowel syndrome. In another embodiment, a pharmaceutical composition remains effective after at least 4, 8, 10, 16, 20, 24, 30, 40, 50, 60, 70, 80 or 100 weeks of storage at ambient temperature or lower.

In one embodiment, the present disclosure provides a method for treating a disorder (e.g., *C. difficile* infection, autism spectrum disorder (ASD), ulcerative colitis, Crohn's disease, or another indication listed herein) in a subject in need thereof, where the method comprises administering to the subject a pharmaceutically active dose of a therapeutic composition described herein. In one embodiment, the present disclosure provides a method for treating a disorder (e.g., *C. difficile* infection, ASD, ulcerative colitis, or Crohn's disease) in a subject in need thereof, where the method comprises administering daily to the subject a pharmaceutically active dose of a therapeutic composition described herein. In one embodiment, a therapeutic composition is administered to a patient in need thereof at least once daily for at least two consecutive days. In one embodiment, a therapeutic composition is administered at least once daily for at least 3, 4, 5, 6, 7, 8, 9, 10, 11, 12, 13, 14, or 15 consecutive days. In another embodiment, a therapeutic composition is administered at least once daily for at least 1, 2, 3, 4, 5, 6, 7, 8, 9, 10, 11, or 12 consecutive weeks. In one embodiment, a therapeutic composition is administered at least once daily for at most 4, 5, 6, 7, 8, 9, 10, 11, 12, 13, 14, 15, 16, 17, 18, 19, or 20 consecutive days or weeks. In another embodiment, a therapeutic composition is administered at least once daily for at most 1, 2, 3, 4, 5, 6, 7, 8, 9, 10, 11, or 12 consecutive weeks or months. In a further embodiment, a therapeutic composition is administered at least once for at least 1, 2, 3, 4, 5, 6, 7, 8, 9, 10, 11, or 12 consecutive months or years, chronically for a subject's entire life span, or an indefinite period of time.

In one embodiment, a therapeutic composition is administered to a patient in need thereof at least twice daily for at least two consecutive days. In one embodiment, a therapeutic composition is administered at least twice daily for at least 3, 4, 5, 6, 7, 8, 9, 10, 11, 12, 13, 14, or 15 consecutive days. In another embodiment, a therapeutic composition is administered at least twice daily for at least 1, 2, 3, 4, 5, 6, 7, 8, 9, 10, 11, or 12 consecutive weeks. In one embodiment, a therapeutic composition is administered at least twice daily for at most 4, 5, 6, 7, 8, 9, 10, 11, 12, 13, 14, 15, 16, 17, 18, 19, or 20 consecutive days or week. In another embodiment, a therapeutic composition is administered at least twice daily for at most 1, 2, 3, 4, 5, 6, 7, 8, 9, 10, 11, or 12 consecutive weeks or months. In a further embodiment, a therapeutic composition is administered at least twice for at least 1, 2, 3, 4, 5, 6, 7, 8, 9, 10, 11, or 12 consecutive months or years, chronically for a subject's entire life span, or an indefinite period of time.

In one embodiment, a therapeutic composition is administered to a patient in need thereof at least three times daily for at least two consecutive days. In one embodiment, a therapeutic composition is administered at least three times daily for at least 3, 4, 5, 6, 7, 8, 9, 10, 11, 12, 13, 14, or 15 consecutive days. In another embodiment, a therapeutic composition is administered at least three times daily for at least 1, 2, 3, 4, 5, 6, 7, 8, 9, 10, 11, or 12 consecutive weeks. In one embodiment, a therapeutic composition is administered at least three times daily for at most 4, 5, 6, 7, 8, 9, 10, 11, 12, 13, 14, 15, 16, 17, 18, 19, or 20 consecutive days or weeks. In another embodiment, a therapeutic composition is administered at least three times daily for at most 1, 2, 3, 4, 5, 6, 7, 8, 9, 10, 11, or 12 consecutive weeks or months. In a further embodiment, a therapeutic composition is administered at least three times for at least 1, 2, 3, 4, 5, 6, 7, 8, 9, 10, 11, or 12 consecutive months or years, chronically for a subject's entire life span, or an indefinite period of time.

In one embodiment, the present disclosure provides a method for treating a disorder (e.g., *C. difficile* infection, ASD, ulcerative colitis, or Crohn's disease) in a subject in need thereof, where the method comprises administering orally to the subject a pharmaceutically active dose of a therapeutic composition comprising live, non-pathogenic, synthetic bacterial mixture or live, non-pathogenic, purified or extracted, fecal microbiota in a lyophilized formulation described herein, where the dose is administered at a dosing schedule of at least once or twice daily for at least three consecutive days or weeks. In another embodiment, a dose is administered at least once, twice, or three times daily for a period between 1 and 12 weeks, between 2 and 12 weeks, between 3 and 12 weeks, between 4 and 12 weeks, between 5 and 12 weeks, between 6 and 12 weeks, between 7 and 12 weeks, between 8 and 12 weeks, between 9 and 12 weeks, between 10 and 12 weeks, between 1 and 2 weeks, between 2 and 3 weeks, between 3 and 4 weeks, between 4 and 5 weeks, between 5 and 6 weeks, between 6 and 7 weeks, between 7 and 8 weeks, between 8 and 9 weeks, between 9 and 10 weeks, or between 10 and 11 weeks.

In one embodiment, the present disclosure provides a method for treating a disorder (e.g., *C. difficile* infection, ASD, ulcerative colitis, or Crohn's disease) in a subject in need thereof by administering a pharmaceutical composition described herein, where the method comprises a first dosing schedule followed by a second dosing schedule. In one embodiment, a first dosing schedule comprises a treatment or induction dose. In one embodiment, a first dosing schedule comprises a continuous dosing schedule. In another embodiment, a second dosing schedule comprises a maintenance dose lower than or equal to a pharmaceutically active dose of a first dosing schedule. In another embodiment, a second dosing schedule lasts for at least about 2, 4, 6, 8, 10, 12, 18, 24, 36, 48, 72, or 96 months. In one embodiment, a second dosing schedule lasts permanently, for a treated subject's entire life span, or an indefinite period of time. In one embodiment, a second dosing schedule is a continuous dosing schedule. In another embodiment, a second dosing schedule is an intermittent dosing schedule. In a further embodiment, a second dosing schedule is an intermittent dosing schedule comprising a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days. In another embodiment, a second dosing schedule comprises administering a second dose (e.g., a maintenance dose) every other day, every two days, or every 3, 4, 5, 6, 7, 8 days. In another embodiment, a maintenance dose is administered for an extended period of time with or without titration (or otherwise changing the dosage or dosing schedule). In one embodiment, the interval between a first and a second dosing schedule is at least about 1, 2, 3, 4, 5, 6, 7, 8, 9, 10, 11, or 12 weeks. In another embodiment, a second dosing schedule (e.g., a maintenance dose) comprises a dosage about 2, 5, 10, 50, 100, 200, 400, 800, 1000, 5000 or more folds lower than the dosage used in a first dosing schedule (e.g., an initial treatment dose). In another embodiment, a second dosing schedule (e.g., a maintenance dosing schedule) has an equal or lower dosing frequency than a first dosing schedule (e.g., an initial treatment dosing schedule). In another embodiment, a second dosing schedule (e.g., a maintenance dosing schedule) has a higher dosing interval than a first dosing schedule (e.g., an initial treatment dosing schedule).

In one embodiment, a first or second dosing schedule used in a method can be once-a-week, twice-a-week, or thrice-a-week. The term "once-a-week" means that a dose is administered once in a week, preferably on the same day of each week. "Twice-a-week" means that a dose is administered two times in a week, preferably on the same two days of each weekly period. "Thrice-a-week" means that a dose is administered three times in a week, preferably on the same three days of each weekly period.

In one embodiment, a subject being treated is a subject already with a disorder (e.g., ulcerative colitis or Crohn's disease). Administration of a disclosed therapeutic composition to clinically, asymptomatic human subject who is genetically predisposed or prone to a disorder (e.g., ulcerative colitis or Crohn's disease) is also useful in preventing the onset of clinical symptoms. A human subject genetically predisposed or prone to ulcerative colitis can be a human subject having a close family member or relative exhibiting or having suffered a disorder (e.g., ulcerative colitis or Crohn's disease). In another embodiment, a subject being treated is a subject in which ulcerative colitis is to be prevented. In another embodiment, a subject being treated is predisposed or susceptible to a disorder (e.g., ulcerative colitis or Crohn's disease). In another embodiment, a subject being treated is a subject diagnosed as having a disorder (e.g., ulcerative colitis or Crohn's disease). In one embodiment, a subject being treated is a patient in need thereof.

In one embodiment, a subject being treated is a human patient. In one embodiment, a patient is a male patient. In one embodiment, a patient is a female patient. In one embodiment, a patient is a premature newborn. In one embodiment, a patient is a term newborn. In one embodiment, a patient is a neonate. In one embodiment, a patient is an infant. In one embodiment, a patient is a toddler. In one embodiment, a patient is a young child. In one embodiment, a patient is a child. In one embodiment, a patient is an adolescent. In one embodiment, a patient is a pediatric patient. In one embodiment, a patient is a geriatric patient. In one embodiment, a human patient is a child patient below about 18, 15, 12, 10, 8, 6, 4, 3, 2, or 1 year old. In another embodiment, a human patient is an adult patient. In another embodiment, a human patient is an elderly patient. In a further embodiment, a human patient is a patient above about 30, 35, 40, 45, 50, 55, 60, 65, 70, 75, 80, 85, 90, or 95 years old. In another embodiment, a patient is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In one embodiment, a patient is a young old patient (65-74 years). In one embodiment, a patient is a middle old patient (75-84 years). In one embodiment, a patient is an old old patient (>85 years).

In one embodiment, a method comprises administering a therapeutic composition orally, by enema, or via rectal suppository. In one embodiment, a pharmaceutical composition is formulated as a geltab, pill, microcapsule, capsule, or tablet. In one embodiment, a therapeutic composition is formulated as an enteric coated capsule or microcapsule, acid-resistant capsule or microcapsule, or formulated as part of or administered together with a food, a food additive, a dairy-based product, a soy-based product or a derivative thereof, a jelly, or a yogurt. In another embodiment, a therapeutic composition is formulated as an acid-resistant enteric coated capsule. A therapeutic composition can be provided as a powder for sale in combination with a food or drink. A food or drink can be a dairy-based product or a soy-based product. In another embodiment, a food or food supplement contains enteric-coated and/or acid-resistant microcapsules containing a therapeutic composition.

In an embodiment, a therapeutic composition comprises a liquid culture. In another embodiment, a therapeutic composition is lyophilized, pulverized and powdered. It may then be infused, dissolved such as in saline, as an enema. Alternatively the powder may be encapsulated as enteric-coated and/or acid-resistant capsules for oral administration. These capsules may take the form of enteric-coated and/or acid-resistant microcapsules. A powder can preferably be provided in a palatable form for reconstitution for drinking or for reconstitution as a food additive. In a further embodiment, a food is yogurt. In one embodiment, a powder may be reconstituted to be infused via naso-duodenal infusion.

In another embodiment, a therapeutic composition is in a liquid, frozen, freeze-dried, spray-dried, lyophilized, or powder formulation. In a further embodiment, a therapeutic composition is formulated as a delayed or gradual enteric release form. In another embodiment, a therapeutic composition comprises an excipient, a saline, a buffer, a buffering agent, or a fluid-glucose-cellobiose agar (RGCA) media.

In one embodiment, a therapeutic composition further comprises an acid suppressant, an antacid, an H2 antagonist, a proton pump inhibitor or a combination thereof. In one embodiment, a therapeutic composition substantially free of non-living matter. In another embodiment, a therapeutic composition substantially free of acellular material selected from the group consisting of residual fiber, DNA, viral coat material, and non-viable material.

In one embodiment, a therapeutic composition also comprises or is supplemented with a prebiotic nutrient selected from the group consisting of polyols, fructooligosaccharides (FOSs), oligofructoses, inulins, galactooligosaccharides (GOSs), xylooligosaccharides (XOSs), polydextroses, monosaccharides, tagatose, and/or mannooligosaccharides.

In one embodiment, a method further comprises pretreating a subject with an antibiotic composition prior to administering a therapeutic bacterial or microbiota composition. In one embodiment, an antibiotic composition comprises an antibiotic selected from the group consisting of rifabutin, clarithromycin, clofazimine, vancomycin, rifampicin, nitroimidazole, chloramphenicol, and a combination thereof. In another embodiment, an antibiotic composition comprises an antibiotic selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof. In a further embodiment, a method further comprises pretreating a subject with an anti-inflammatory drug prior to administration of a therapeutic bacterial or microbiota composition.

In one aspect, every about 200 mg of a pharmaceutical composition comprises a pharmacologically active dose. In one aspect, every about 75, 100, 125, 150, 175, 200, 250, 300, 350, 400, 450, 500, 750, 1000, 1500, or 2000 mg of a pharmaceutical composition comprises a pharmacologically active dose.

In one embodiment, a pharmaceutically active or therapeutic effective dose comprises at least about $10^5$, $10^6$, $10^7$, $10^8$, $10^9$, $10^{10}$, $10^{11}$, $10^{12}$, or $10^{13}$ cfu. In another embodiment, a pharmaceutically active therapeutic effective dose comprises at most about $10^5$, $10^6$, $10^7$, $10^8$, $10^9$, $10^{10}$, $10^{11}$, $10^{12}$, or $10^{13}$ cfu. In a further embodiment, a pharmacologically active therapeutic effective dose is selected from the group consisting of from $10^8$ cfu to $10^{14}$ cfu, from $10^9$ cfu to $10^{13}$ cfu, from $10^{10}$ cfu to $10^{12}$ cfu, from $10^9$ cfu to $10^{14}$ cfu, from $10^9$ cfu to $10^{12}$ cfu, from $10^9$ cfu to $10^{11}$ cfu, from $10^9$ cfu to $10^{10}$ cfu, from $10^{10}$ cfu to $10^{14}$ cfu, from $10^{10}$ cfu to $10^{13}$ cfu, from $10^{11}$ cfu to $10^{14}$ cfu, from $10^{11}$ cfu to $10^{13}$ cfu, from $10^{12}$ cfu to $10^{14}$ cfu, and from $10^{13}$ cfu to $10^{14}$ cfu.

In one embodiment, a pharmaceutically active or therapeutic effective dose comprises at least about $10^5$, $10^6$, $10^7$, $10^8$, $10^9$, $10^{10}$, $10^{11}$, $10^{12}$, or $10^{13}$ cells or spores. In another embodiment, a pharmaceutically active or therapeutic effective dose comprises at most about $10^5$, $10^6$, $10^7$, $10^8$, $10^9$, $10^{10}$, $10^{11}$, $10^{12}$, or $10^{13}$ total cells or spores. In a further embodiment, a pharmacologically active or therapeutic effective dose is selected from the group consisting of from $10^8$ to $10^{14}$, from $10^9$ to $10^{13}$, from $10^{10}$ to $10^{12}$, from $10^9$ to $10^{14}$, from $10^9$ to $10^{12}$, from $10^9$ to $10^{11}$, from $10^9$ to $10^{10}$ from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, and from $10^{13}$ to $10^{14}$ cells or spores. In an embodiment, the pharmaceutically active or therapeutic effective dose cell count is directed to live cells.

In one embodiment, a therapeutic composition comprises one or more, two or more, three or more, four or more, or five or more isolated, purified, or cultured microorganisms selected from the group consisting of *Clostridium, Bacillus, Collinsella, Bacteroides, Eubacterium, Fusobacterium, Propionibacterium, Lactobacillus, Ruminococcus, Escherichia coli, Gemmiger, Desulfomonas, Peptostreptococcus, Bifidobacterium, Coprococcus, Dorea*, and *Monilia*.

In one embodiment, a fecal microbiota preparation described herein comprises a purified or reconstituted fecal bacterial mixture. In one embodiment, a fecal microbiota preparation comprises one or more, one or more, two or more, three or more, four or more, or five or more live fecal microorganisms are selected from the group consisting of *Acidaminococcus, Akkermansia, Alistipes, Anaerotruncus, Bacteroides, Bifidobacterium, Blautia, Butyrivibrio, Clostridium, Collinsella, Coprococcus, Corynebacterium, Dorea, Enterococcus, Escherichia, Eubacterium, Faecalibacterium, Haemophilus, Holdemania, Lactobacillus, Moraxella, Parabacteroides, Prevotella, Propionibacterium, Raoultella, Roseburia, Ruminococcus, Staphylococcus, Streptococcus, Subdoligranulum*, and *Veillonella*. In one embodiment, a fecal microbiota preparation comprises one or more, one or more, two or more, three or more, four or more, or five or more live fecal microorganisms are selected from the group consisting of *Bacteroides fragilis* ssp. *vulgatus, Collinsella aerofaciens, Bacteroides fragilis* ssp. *thetaiotaomicron, Peptostreptococcus productus* II, *Parabacteroides distasonis, Faecalibacterium prausnitzii, Coprococcus eutactus, Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. A, *Eubacterium biforme, Bifidobacterium infantis, Eubacterium rectale, Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Coprococcus catus, Aerostipes hadrus, Eubacterium cylindroides, Eubacterium ruminantium*. *Staphylococcus epidermidis, Eubacterium limosum, Tissirella praeacuta, Fusobacterium mortiferum* I, *Fusobacterium naviforme, Clostridium innocuum, Clostridium ramosum, Propionibacterium acnes, Ruminococcus flavefaciens, Bacteroides fragilis* ssp. *ovatus, Fusobacterium nucleatum, Fusobacterium mortiferum, Escherichia coli, Gemella morbillorum, Finegoldia magnus, Streptococcus intermedius, Ruminococcus lactaris, Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus*, and *Desuifomonas pigra*.

In one embodiment, a fecal microbiota preparation lacks or is substantially devoid of one or more, one or more, two or more, three or more, four or more, or five or more live fecal microorganisms are selected from the group consisting of *Acidaminococcus, Akkermansia, Alistipes, Anaerotruncus, Bacteroides, Bifidobacterium, Blautia, Butyrivibrio, Clostridium, Collinsella, Coprococcus, Corynebacterium, Dorea, Enterococcus, Escherichia, Eubacterium, Faecalibacterium, Haemophilus, Holdemania, Lactobacillus, Moraxella, Parabacteroides, Prevotella, Propionibacterium, Raoultella, Roseburia, Ruminococcus, Staphylococcus, Streptococcus, Subdoligranulum*, and *Veillonella*. In one embodiment, a fecal microbiota preparation lacks or is substantially devoid of one or more, one or more, two or more, three or more, four or more, or five or live more fecal microorganisms are selected from the group consisting of *Bacteroides fragilis* ssp. *vulgatus, Collinsella aerofaciens, Bacteroides fragilis* ssp. *thetaiotaomicron, Peptostreptococcus productus* II, *Parabacteroides distasonis, Faecalibacterium prausnitzii, Coprococcus eutactus, Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. A, *Eubacterium biforme, Bifidobacterium infantis, Eubacterium rectale, Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Coprococcus catus, Aerostipes hadrus, Eubacterium cylindroides, Eubacterium ruminantium, Staphylococcus epidermidis, Eubacterium limosum, Tissirella praeacuta, Fusobacterium mortiferum* I, *Fusobacterium naviforme, Clostridium innocuum, Clostridium ramosum, Propionibacterium acnes, Ruminococcus flavefaciens, Bacteroides fragilis* ssp. *ovatus, Fusobacterium nucleatum, Fusobacterium mortiferum, Escherichia coli, Gemella morbillorum, Finegoldia magnus, Streptococcus intermedius, Ruminococcus lactaris, Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus*, and *Desuifomonas pigra*.

In another embodiment, a therapeutic composition comprises a fecal microbiota further supplemented, spiked, or enhanced with a fecal microorganism. In one embodiment, a fecal microbiota is supplemented with a non-pathogenic (or with attenuated pathogenicity) bacterium of *Clostridium, Collinsella, Dorea, Ruminococcus, Coprococcus, Prevotella, Veillonella, Bacteroides, Baccillus*, or a combination thereof. In another embodiment, a therapeutic composition comprises a fecal microbiota further supplemented, spiked, or enhanced with a species of *Veillonellaceae, Firmicutes, Gammaproteobacteria, Bacteroidetes*, or a combination thereof. In another embodiment, a therapeutic composition comprises a fecal microbiota further supplemented with fecal bacterial spores. In one embodiment, fecal bacterial spores are *Clostridium* spores, *Bacillus* spores, or both.

In an embodiment, a therapeutic composition comprises a fecal microbiota from a subject selected from the group consisting of a human, a bovine, a dairy calf, a ruminant, an ovine, a caprine, or a cervine. In another embodiment, a therapeutic composition can be administered to a subject selected from the group consisting of a human, a bovine, a dairy calf, a ruminant, an ovine, a caprine, or a cervine. In an embodiment, a therapeutic composition is substantially or nearly odourless.

In an embodiment, a therapeutic composition provided here comprises a fecal microbiota comprising a Shannon Diversity Index of greater than or equal to 0.3, greater than or equal to 0.4, greater than or equal to 0.5, greater than or equal to 0.6, greater than or equal to 0.7, greater than or equal to 0.8, greater than or equal to 0.9, greater than or equal to 1.0, greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, greater than or equal to 1.9, greater than or equal to 2.0, greater than or equal to 2.1, greater than or equal to 2.2, greater than or equal to 2.3, greater than or equal to 2.4, greater than or equal to 2.5, greater than or equal to 3.0, greater than or equal to 3.1, greater than or equal to 3.2, greater than or equal to 3.3, greater than or equal to 3.4, greater than or equal to 3.5, greater than or equal to 3.6, greater than or equal to 3.7, greater than or equal to 3.8, greater than or equal to 3.9, greater than or equal to 4.0, greater than or equal to 4.1, greater than or equal to 4.2, greater than or equal to 4.3, greater than or equal to 4.4, greater than or equal to 4.5, or greater than or equal to 5.0. In another embodiment, a therapeutic composition comprises fecal microbiota comprising a Shannon Diversity Index of between 0.1 and 3.0, between 0.1 and 2.5, between 0.1 and 2.4, between 0.1 and 2.3, between 0.1 and 2.2, between 0.1 and 2.1, between 0.1 and 2.0, between 0.4 and 2.5, between 0.4 and 3.0, between 0.5 and 5.0, between 0.7 and 5.0, between 0.9 and 5.0, between 1.1 and 5.0, between 1.3 and 5.0, between 1.5 and 5.0, between 1.7 and 5.0, between 1.9 and 5.0, between 2.1 and 5.0, between 2.3 and 5.0, between 2.5 and 5.0, between 2.7 and 5.0, between 2.9 and 5.0, between 3.1 and 5.0, between 3.3 and 5.0, between 3.5 and 5.0, between 3.7 and 5.0, between 31.9 and 5.0, or between 4.1 and 5.0. In one embodiment, a Shannon Diversity Index is calculated at the phylum level. In another embodiment, a Shannon Diversity Index is calculated at the family level. In one embodiment, a Shannon Diversity Index is calculated at the genus level. In another embodiment, a Shannon Diversity Index is calculated at the species level. In a further embodiment, a therapeutic composition comprises a preparation of flora in proportional content that resembles a normal healthy human fecal flora.

In a further embodiment, a therapeutic composition comprises fecal bacteria from at least 1, 2, 3, 4, 5, 6, 7, 8, 9, or 10 different families. In an embodiment, a therapeutic composition provided here comprises a fecal microbiota comprising no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material. In another embodiment, a therapeutic composition provided here comprises a fecal microbiota comprising no greater than 20%, 25%, 30%, 35%, 40%, 45%, 50%, 55%, 60%, 65%, 70%, 75%, 80%, 85%, 90%, or 95% weight non-living material/weight biological material. In another embodiment, a therapeutic composition provided here comprises, consists of, or consists essentially of, particles of non-living material and/or particles of biological material of a fecal sample that passes through a sieve, a column, or a similar filtering device having a sieve, exclusion, or particle filter size of 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm. "Non-living material" does not include an excipient, e.g., a pharmaceutically inactive substance, such as a cryoprotectant, added to a processed fecal material. "Biological material" refers to the living material in fecal material, and includes microbes including prokaryotic cells, such as bacteria and archaea (e.g., living prokaryotic cells and spores that can sporulate to become living prokaryotic cells), eukaryotic cells such as protozoa and fungi, and viruses. In one embodiment, "biological material" refers to the living material, e.g., the microbes, eukaryotic cells, and viruses, which are present in the colon of a normal healthy human. In an embodiment, a therapeutic composition provided or comprises an extract of human feces where the composition is substantially odorless. In an embodiment, a therapeutic composition provided or comprises fecal material or a fecal floral preparation in a lyophilized, crude, semi-purified or purified formulation.

In an embodiment, a fecal microbiota in a therapeutic composition comprises highly refined or purified fecal flora, e.g., substantially free of non-floral fecal material. In an embodiment, a fecal microbiota can be further processed, e.g., to undergo microfiltration before, after, or before and after sieving. In another embodiment, a highly purified fecal microbiota product is ultra-filtrated to remove large molecules but retain the therapeutic microflora, e.g., bacteria.

In another embodiment, a fecal microbiota in a therapeutic composition used herein comprises or consists essentially of a substantially isolated or a purified fecal flora or entire (or substantially entire) microbiota that is (or comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or, a substantially isolated, purified, or substantially entire microbiota as described in Sadowsky et al., WO 2012/122478 A1, or as described in Borody et al., WO 2012/016287 A2. In one aspect, a fecal microbiota preparation comprises a weight ratio between fecal-derived non-living material and fecal-derived biological material of no greater than about 0.1%, 0.2%, 0.3%, 0.4%, 0.5%, 0.6%, 0.7%, 0.8%, 0.9%, 1%, 2%, 5%, 8%, 10%, 15%, 20%, 30%, 40$, or 50%.

In an embodiment, a fecal microbiota in a therapeutic composition comprises a donor's substantially entire or non-selective fecal microbiota, reconstituted fecal material, or synthetic fecal material. In another embodiment, the fecal microbiota in a therapeutic composition comprises no antibiotic resistant population. In another embodiment, a therapeutic composition comprises a fecal microbiota and is largely free of extraneous matter (e.g., non-living matter including acellular matter such as residual fiber, DNA, RNA, viral coat material, non-viable material; and living matter such as eukaryotic cells from the fecal matter's donor).

In an embodiment, a fecal microbiota in a therapeutic composition used herein is derived from disease-screened fresh homologous feces or equivalent freeze-dried and reconstituted feces. In an embodiment, a fresh homologous feces does not include an antibiotic resistant population. In another embodiment, a fecal microbiota in a therapeutic composition is derived from a synthetic fecal composition. In an embodiment, a synthetic fecal composition comprises a preparation of viable flora which preferably in proportional content, resembles normal healthy human fecal flora which does not include antibiotic resistant populations. Suitable microorganisms may be selected from the following: *Bacteroides, Eubacterium, Fusobacterium, Propionibacterium, Lactobacillus, Ruminococcus, Escherichia coli, Gemmiger, Clostridium, Desulfomonas, Peptostreptococcus, Bifidobacterium, Collinsella, Coprococcus, Dorea*, and *Ruminococcus*.

In an embodiment, a therapeutic composition is combined with other adjuvants such as antacids to dampen bacterial inactivation in the stomach. (e.g., Mylanta, Mucaine, Gastrogel). In another embodiment, acid secretion in the stomach could also be pharmacologically suppressed using H2-antagonists or proton pump inhibitors. An example H2-antagonist is ranitidine. An example proton pump inhibitor is omeprazole. In one embodiment, an acid suppressant is administered prior to administering, or in co-administration with, a therapeutic composition.

In an embodiment, a therapeutic composition is administered in the form of: an enema composition which can be reconstituted with an appropriate diluent; enteric-coated capsules; enteric-coated microcapsules; acid-resistant tablet; acid-resistant capsules; acid-resistant microcapsules; powder for reconstitution with an appropriate diluent for nasoenteric infusion or colonoscopic infusion; powder for reconstitution with appropriate diluent, flavoring and gastric acid suppression agent for oral ingestion; powder for reconstitution with food or drink; or food or food supplement comprising enteric-coated and/or acid-resistant microcapsules of the composition, powder, jelly, or liquid.

In an embodiment, a treatment method effects a cure, reduction of the symptoms, or a percentage reduction of symptoms of a disorder (e.g., IBD such as ulcerative colitis or Crohn's disease). The change of flora is preferably as "near-complete" as possible and the flora is replaced by viable organisms which will crowd out any remaining, original flora. Typically the change in enteric flora comprises introduction of an array of predetermined flora into the gastro-intestinal system, and thus in a preferred form the method of treatment comprises substantially or completely displacing pathogenic enteric flora in patients requiring such treatment.

In another embodiment, a therapeutic composition can be provided together with a pharmaceutically acceptable carrier. As used herein, a "pharmaceutically acceptable carrier" refers to a non-toxic solvent, dispersant, excipient, adjuvant, or other material which is mixed with a live bacterium in order to permit the formation of a pharmaceutical composition, e.g., a dosage form capable of administration to the patient. A pharmaceutically acceptable carrier can be liquid (e.g., saline), gel or solid form of diluents, adjuvant, excipients or an acid resistant encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In another embodiment, a therapeutic composition may contain auxiliary substances such as wetting or emulsifying agents, stabilizing or pH buffering agents. In an embodiment, a therapeutic composition contains about 1%-5%, 5%-10%, 10%-15%, 15-20%, 20%-25%, 25-30%, 30-35%, 40-45%, 50%-55%, 1%-95%, 2%-95%, 5%-95%, 10%-95%, 15%-95%, 20%-95%, 25%-95%, 30%-95%, 35%-95%, 40%-95%, 45%-95%, 50%-95%, 55%-95%, 60%-95%, 65%-95%, 70%-95%, 45%-95%, 80%-95%, or 85%-95% of active ingredient. In an embodiment, a therapeutic composition contains about 2%-70%, 5%-60%, 10%-50%, 15%-40%, 20%-30%, 25%-60%, 30%-60%, or 35%-60% of active ingredient.

In an embodiment, a therapeutic composition can be incorporated into tablets, drenches, boluses, capsules or premixes. Formulation of these active ingredients into such dosage forms can be accomplished by means of methods well known in the pharmaceutical formulation arts. See, e.g., U.S. Pat. No. 4,394,377. Filling gelatin capsules with any desired form of the active ingredients readily produces capsules. If desired, these materials can be diluted with an inert powdered diluent, such as sugar, starch, powdered milk, purified crystalline cellulose, or the like to increase the volume for convenience of filling capsules.

In an embodiment, conventional formulation processes can be used to prepare tablets containing a therapeutic composition. In addition to the active ingredients, tablets may contain a base, a disintegrator, an absorbent, a binder, and a lubricant. Typical bases include lactose, sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents include starch and lactose. Magnesium carbonate is also useful for oily substances. As a binder there can be used, for example, gelatin, gums, starch, dextrin, polyvinyl pyrrolidone and various cellulose derivatives. Among the commonly used lubricants are magnesium stearate, talc, paraffin wax, various metallic soaps, and polyethylene glycol.

In an embodiment, for preparing solid compositions such as tablets, an active ingredient is mixed with a pharmaceutical carrier, e.g., conventional tableting ingredients such as corn starch, lactose, sucrose, sorbitol, talc, stearic acid, magnesium stearate, dicalcium phosphate or gums, or other pharmaceutical diluents, e.g. water, to form a solid preformulation composition containing a homogeneous mixture of a composition of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing a desired amount of an active ingredient (e.g., at least about $10^5$, $10^6$, $10^7$, $10^8$, $10^9$, $10^{10}$, $10^{11}$, $10^{12}$, or $10^{13}$ cfu). A therapeutic composition used herein can be flavored.

In an embodiment, a therapeutic composition can be a tablet or a pill. In one embodiment, a tablet or a pill can be coated or otherwise compounded to provide a dosage form affording the advantage of prolonged action. For example, a tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

In an embodiment, a therapeutic composition is formulated as a delayed or gradual enteric release form. In an embodiment, a delayed or gradual enteric release formulation comprises the use of cellulose acetate, polyethylene glycerol, or both. In an embodiment, a delayed or gradual enteric release formulation comprises the use of a hydroxypropylmethylcellulose (HPMC), a microcrystalline cellulose (MCC), magnesium stearate, or a combination thereof. In an embodiment, a delayed or gradual enteric release formulation comprises the use of a poly(meth)acrylate, a methacrylic acid copolymer B, a methyl methacrylate, a methacrylic acid ester, a polyvinylpyrrolidone (PVP), a PVP-K90, or a combination thereof. In an embodiment, a delayed or gradual enteric release formulation comprises the use of a solid inner layer sandwiched between two outer layers; wherein the solid inner layer comprises the pharmaceutical composition and another component selected from the group consisting of a disintegrant, an exploding agent, an effervescent or any combination thereof; wherein the outer layer comprises a substantially water soluble, a crystalline polymer, or both. In an embodiment, a delayed or gradual enteric release formulation comprises the use of a non-swellable diffusion matrix.

In another embodiment, a delayed or gradual enteric release formulation comprises the use of a bilayer tablet or capsule which comprises a first layer comprising a polyalkylene oxide, a polyvinylpyrrolidone, a lubricant, or a mixture thereof, and a second osmotic push layer comprising polyethylene oxide, carboxy-methylcellulose, or both. In an embodiment, a delayed or gradual enteric release formulation comprises the use of a release-retarding matrix material selected from the group consisting of an acrylic polymer, a cellulose, a wax, a fatty acid, shellac, zein, hydrogenated vegetable oil, hydrogenated castor oil, polyvinylpyrrolidine, a vinyl acetate copolymer, a vinyl alcohol copolymer, polyethylene oxide, an acrylic acid and methacrylic acid copolymer, a methyl methacrylate copolymer, an ethoxyethyl methacrylate polymer, a cyanoethyl methacrylate polymer, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate polymer, a polymethacrylate, a poly(methyl methacrylate) copolymer, a polyacrylamide, an aminoalkyl methacrylate copolymer, a glycidyl methacrylate copolymer, a methyl cellulose, an ethylcellulose, a carboxymethylcellulose, a hydroxypropylmethylcellulose, a hydroxymethyl cellulose, a hydroxyethyl cellulose, a hydroxypropyl cellulose, a crosslinked sodium carboxymethylcellulose, a crosslinked hydroxypropylcellulose, a natural wax, a synthetic wax, a fatty alcohol, a fatty acid, a fatty acid ester, a fatty acid glyceride, a hydrogenated fat, a hydrocarbon wax, stearic acid, stearyl alcohol, beeswax, glycowax, castor wax, carnauba wax, a polylactic acid, polyglycolic acid, a co-polymer of lactic and glycolic acid, carboxymethyl starch, potassium methacrylate/divinylbenzene copolymer, crosslinked polyvinylpyrrolidone, poly inylalcohols, polyvinylalcohol copolymers, polyethylene glycols, non-crosslinked polyvinylpyrrolidone, polyvinylacetates, polyvinylacetate copolymers, or any combination thereof. In an embodiment, a delayed or gradual enteric release formulation comprises the use of a microenvironment pH modifier.

In an embodiment, a therapeutic composition can be a drench. In one embodiment, a drench is prepared by choosing a saline-suspended form of a therapeutic composition. A water-soluble form of one ingredient can be used in conjunction with a water-insoluble form of the other by preparing a suspension of one with an aqueous solution of the other. Water-insoluble forms of either active ingredient may be prepared as a suspension or in some physiologically acceptable solvent such as polyethylene glycol. Suspensions of water-insoluble forms of either active ingredient can be prepared in oils such as peanut, corn, sesame oil or the like; in a glycol such as propylene glycol or a polyethylene glycol; or in water depending on the solubility of a particular active ingredient. Suitable physiologically acceptable adjuvants may be necessary in order to keep the active ingredients suspended. Adjuvants can include and be chosen from among the thickeners, such as carboxymethylcellulose, polyvinyl pyrrolidone, gelatin and the alginates. Surfactants generally will serve to suspend the active ingredients, particularly the fat-soluble propionate-enhancing compounds. Most useful for making suspensions in liquid nonsolvents are alkylphenol polyethylene oxide adducts, naphthalene-sulfonates, alkylbenzene-sulfonates, and the polyoxyethylene sorbitan esters. In addition many substances, which affect the hydrophilicity, density and surface tension of the liquid, can assist in making suspensions in individual cases. For example, silicone anti-foams, glycols, sorbitol, and sugars can be useful suspending agents.

In an embodiment, a therapeutic composition comprises non-pathogenic spores of one or more, two or more, three or more, or four or more *Clostridium* species selected from the group consisting of *Clostridium absonum*, *Clostridium argentinense*, *Clostridium baratii*, *Clostridium botulinum*, *Clostridium cadaveris*, *Clostridium carnis*, *Clostridium celatum*, *Clostridium chauvoei*, *Clostridium clostridioforme*, *Clostridium cochlearium*, *Clostridium fallax*, *Clostridium felsineum*, *Clostridium ghonii*, *Clostridium glycolicum*, *Clostridium haemolyticum*, *Clostridium hastiforme*, *Clostridium histolyticum*, *Clostridium indolis*, *Clostridium irregulare*, *Clostridium limosurn*, *Clostridium malenominatum*, *Clostridium novyi*, *Clostridium oroticum*, *Clostridium paraputrificum*, *Clostridium perfringens*, *Clostridium piliforme*, *Clostridium putrefaciens*, *Clostridium putrificum*, *Clostridium sardiniense*, *Clostridium sartagoforme*, *Clostridium scindens*, *Clostridium septicum*, *Clostridium sordellii*, *Clostridium sphenoides*, *Clostridium spiroforme*, *Clostridium sporogenes*, *Clostridium subterminale*, *Clostridium symbiosum*, *Clostridium tertiurn*, *Clostridium tetani*, *Clostridium welchii*, and *Clostridium villosum*.

In an embodiment, a therapeutic composition comprises purified, isolated, or cultured viable non-pathogenic *Clostridium* and a plurality of purified, isolated, or cultured viable non-pathogenic microorganisms from one or more genera selected from the group consisting of *Collinsella*, *Coprococcus*, *Dorea*, *Eubacterium*, and *Ruminococcus*. In another embodiment, a therapeutic composition comprises a plurality of purified, isolated, or cultured viable non-pathogenic microorganisms from one or more genera selected from the group consisting of *Clostridium*, *Collinsella*, *Coprococcus*, *Dorea*, *Eubacterium*, and *Ruminococcus*.

In an embodiment, a therapeutic composition comprises two or more genera selected from the group consisting of *Collinsella*, *Coprococcus*, *Dorea*, *Eubacterium*, and *Ruminococcus*. In another embodiment, a therapeutic composition comprises two or more genera selected from the group consisting of *Coprococcus*, *Dorea*, *Eubacterium*, and *Ruminococcus*. In a further embodiment, a therapeutic composition comprises one or more, two or more, three or more, four or more, or five or more species selected from the group consisting of *Coprococcus catus*, *Coprococcus comes*, *Dorea longicatena*, *Eubacterium eligens*, *Eubacterium hadrum*, *Eubacterium hallii*, *Eubacterium rectale*, and *Ruminococcus torques*.

In one embodiment, a pharmaceutical composition is in an anaerobic package or container. In another embodiment, a pharmaceutical composition further comprises an oxygen scavenger. In one embodiment, a container can be made oxygen free by e.g., incorporating into the container a built in or clipped-on oxygen-scavenging mechanism, e.g., oxygen scavenging pellets as described e.g., in U.S. Pat. No. 7,541,091. In another embodiment, the container itself is made of an oxygen scavenging material, e.g., oxygen scavenging iron, e.g., as described by O2BLOCK™, or equivalents, which uses a purified and modified layered clay as a performance-enhancing carrier of oxygen-scavenging iron; the active iron is dispersed directly in the polymer. In one embodiment, oxygen-scavenging polymers are used to make the container itself or to coat the container, or as pellets to be added; e.g., as described in U.S. Pat. App. Pub. 20110045222, describing polymer blends having one or more unsaturated olefinic homopolymers or copolymers; one or more polyamide homopolymers or copolymers; one or more polyethylene terephthalate homopolymers or copolymers; that exhibit oxygen-scavenging activity. In one embodiment, oxygen-scavenging polymers are used to make the container itself or to coat the container, or as pellets to be added; e.g., as described in U.S. Pat. App. Pub. 20110008554, describing compositions comprising a polyester, a copolyester ether and an oxidation catalyst, wherein the copolyester ether comprises a polyether segment comprising poly(tetramethylene-co-alkylene ether). In one embodiment, oxygen-scavenging polymers are used to make the container itself or to coat the container, or as pellets to be added; e.g., as described in U.S. Pat. App. Pub. 201000255231, describing a dispersed iron/salt particle in a polymer matrix, and an oxygen scavenging film with oxygen scavenging particulates.

In alternative embodiments, provided herein are pharmaceutical compositions comprising lyophilized, cryo-desiccated, freeze-dried or dehydrated bacterial flora, made by a process comprising:

(a) providing a composition, isolate or preparation comprising, or consisting essentially of, or consisting of:

an entire (or substantially entire) fecal microbiota, optionally isolated and/or stored in a partially, substantially or completely anaerobic environment, a treated or untreated fecal flora sample, a complete or partial fecal flora sample, optionally isolated and/or stored in a partially, substantially or completely anaerobic environment, a fecal flora substantially or completely purified of non-fecal floral fecal material, wherein optionally the fecal flora is separated from a rough particulate matter in a fecal sample by: homogenizing, centrifuging and/or filtering a rough particulate matter or a non-floral matter of the fecal material, or by plasmapheresis, centrifugation, celltrifuge, column chromatography or by immunoprecipitation, and optionally the substantially or completely purified fecal flora has no greater than about 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material, a partially, substantially or completely isolated or purified fecal flora or fecal flora filtrate, wherein optionally the purification process comprises filtering a fecal sample with a filter medium, wherein optionally the filter medium includes at least one sieve size of no greater than about 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, or 0.01 mm, or a sieve size of 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm, to result in or to generate a filtrate, a disease screened fresh homologous feces, optionally substantially or completely purified of non-fecal floral fecal material, or optionally isolated and/or stored in a partially, substantially or completely anaerobic environment, and optionally the fecal flora is initially derived from an individual screened or tested for a disease or an infection, and/or the fecal flora is initially derived from an individual screened to have a normal, healthy or wild type population of fecal flora, a reconstituted feces, optionally reconstituted using cultured viable non-pathogenic or attenuated microorganisms, a synthetic fecal composition of predetermined flora, a synthetic or reconstituted fecal composition comprising a preparation of viable flora in proportional content that resembles a normal healthy human fecal flora, which does not include antibiotic resistant populations, a composition comprising viable, non-pathogenic colonic bacterial cells selected from the group consisting of a *Clostridia*, a *Collinsella*, a *Bacteroides*, a *Fusobacteria*, a *Propionibacteria*, a *Lactobacilli*, an anaerobic cocci, a *Ruminococcus*, an *E. coli*, a *Gemmiger*, a *Desulfomonas*, a *Peptostreptococcus*, a *Bifidobacteria* and any combination thereof.

a composition comprising viable, non-pathogenic colonic bacterial components of fecal flora, wherein the bacterial components comprise *Clostridium bifermentans*, *Clostridium innocuum*, *Clostridium butyricum*, *Escherichia coli*, *Bacteroides* and *Peptostreptococcus productus*, a composition comprising viable, non-pathogenic colonic bacterial components of fecal flora, wherein the bacterial components comprise a *Bacteroides*, an *Escherichia coli*, and a non-pathogenic *Clostridia*, wherein optionally the non-pathogenic *Clostridia* comprise a *Clostridium innocuum*, a *Clostridium bifermentans* and a *Clostridium ramosum*, a composition comprising a plurality of viable non-pathogenic *Clostridia* and a plurality of viable non-pathogenic *Collinsella*, and optionally with no viable *Lactobacilli*, *Bifidobacteria* or *Eubacteria*, and optionally with no viable *Bacteroides*, *Fusobacteria*, *Propionibacteria*, *Lactobacilli*, anaerobic cocci, *Ruminococcus*, *E. coli*, *Gemmiger*, *Desulfomonas*, *Peptostreptococcus* or *Bifidobacteria*, a composition comprising a plurality of viable non-pathogenic *Clostridia*, wherein optionally the plurality of viable non-pathogenic *Clostridia* comprise non-pathogenic *Clostridia* spores, a composition comprising a plurality of viable non-pathogenic *Clostridia* and a plurality of viable non-pathogenic *Collinsella*, wherein optionally the plurality of viable non-pathogenic *Clostridia* comprise non-pathogenic *Clostridia* spores and/or the plurality of viable non-pathogenic *Clostridia* comprise non-pathogenic *Collinsella* spores, wherein optionally the plurality of viable non-pathogenic *Clostridia* and are from a first pure culture and the plurality of viable non-pathogenic *Collinsella* cells from a second pure culture, and/or a composition comprising viable non-pathogenic *Clostridia* spores, a viable non-pathogenic *Bacteroides*, and a viable non-pathogenic *Escherichia coli*, wherein optionally the composition, isolate or preparation has at least about $10^9$ viable cells cells/g, $10^{10}$ viable cells cells/g, $10^{12}$ viable cells cells/g, $10^{13}$ viable cells cells/g, or $10^{14}$ viable cells cells/g, or between about $10^8$ and $10^{14}$ viable cells cells/g, or between about $10^{10}$ and $10^{12}$ viable cells cells/g;

(b) providing a cryoprotectant and optionally a surfactant or an emulsifier, wherein optionally the cryoprotectant comprises: a dimethyl sulfoxide (DMSO) or equivalent; a glycerol, a polyethylene glycol (PEG) or equivalent; a polysaccharide; a sugar, or an amino acid,
wherein optionally the amino acid comprises an alanine, a glycine, a proline, or the sugar comprises a mannitol, a sucrose, a glucose, a lactose, a ribose or trehalose, or the polysaccharide comprises a hydroxypropyl-β-cyclodextrin (HPβCD), or the cryoprotectant comprises any combination of different cryoprotectant compounds,
wherein optionally the surfactant or emulsifier comprises a polysorbate (polyoxyethylene sorbitan monolaurate) or a PEG-ylated sorbitan, optionally a Polysorbate 80 (polyoxyethylene (80) sorbitan monolaurate);
(c) homogenizing the composition, isolate or preparation of (a) with a mixture of saline and cryoprotectant, or with a mixture of saline, cryoprotectant and a surfactant or an emulsifier,
wherein optionally the homogenization is about 1:2, 1:3, 1:4 or 1:5 (w/w) with a solution comprising saline, and optionally the cryoprotectant is present at a concentration of at least 1%, 2%, 3%, 4%, 5%, 6%, 7%, 8%, 9%, or 10% (vol/vol);
(d) lyophilizing, cryodesiccating, freeze-drying or dehydrating the homogenized composition, isolate or preparation mixture of (c),
wherein optionally after the lyophilizing, cryodesiccating, freeze-drying or dehydrating the final water activity (aw) is less than about 0.1, 0.2, 0.3 or 0.4; and
(e) storing, keeping and/or maintaining the lyophilized, cryodesiccated, freeze-dried or dehydrated composition, isolate or preparation at ambient temperature, room temperature, approximately room temperature, or at between about 15° C. to 26° C., or at about 20° C., 21° C., 22° C., 23° C., 24° C., 25° C., 26° C., 27° C. or 28° C.,
wherein optionally the stored pharmaceutical composition has at least about $10^8$ viable cells cells/g, $10^9$ viable cells cells/g, $10^{10}$ viable cells cells/g, $10^{12}$ viable cells cells/g, $10^{13}$ viable cells cells/g, or $10^{14}$ viable cells cells/g, or between about $10^7$ and $10^{12}$ viable cells cells/g, or between about $10^9$ and $10^{11}$ viable cells cells/g.

In alternative embodiments, pharmaceutical compositions provided herein comprise lyophilized, cryodesiccated, freeze-dried or dehydrated bacterial flora formulated with a composition or mixture comprising:

(a) between about 8% to 12% trehalose, or between about 9% to 11% trehalose; with between about 2.0% to 3.0% sucrose, or between about 1.5% to 3.5% sucrose; with between about 0.5% to 1.5% NaCl, or between about 0.7% to 1.2% NaCl; or, a mixture of about 10% trehalose with about 2.5% sucrose and about 0.9% NaCl;

(b) between about 8% to 12% trehalose, or between about 9% to 11% trehalose; with between about 2.0% to 3.0% sucrose, or between about 1.5% to 3.5% sucrose; with between about 0.5% to 1.5% NaCl, or between about 0.7% to 1.2% NaCl; and with between about 0.005% and 1% polysorbate, or between about 0.01% and 0.5% polysorbate; or, a mixture of about 10% trehalose with about 2.5% sucrose, about 0.9% NaCl and about 0.01% polysorbate 80;

(c) between about 1% to 10% trehalose, or between about 3% to 7% trehalose; with between about 0.5% to 1.5% NaCl, or between about 0.7% to 1.2% NaCl; and with between about 0.005% and 1% polysorbate, or between about 0.01% and 0.5% polysorbate; or, a mixture of about 5% trehalose with about 0.9% NaCl and about 0.01% polysorbate 80;

(d) between about 0.5% to 15% mannitol, or between about 8% to 12% mannitol, or between about 9% to 11% mannitol; with between about 0.5% to 1.5% NaCl, or between about 0.7% to 1.2% NaCl; and with between about 0.005% and 1% polysorbate, or between about 0.01% and 0.5% polysorbate; or, a mixture of about 10% mannitol with about 0.9% NaCl and about 0.01% polysorbate 80;

(e) between about 0.5% to 15% mannitol, or between about 1% to 10% mannitol, or between about 3% to 7% mannitol; with between about 0.5% to 1.5% NaCl, or between about 0.7% to 1.2% NaCl; and with between about 0.005% and 1% polysorbate, or between about 0.01% and 0.5% polysorbate; or, a mixture of about 5% mannitol with about 0.9% NaCl and about 0.01% polysorbate 80;

(f) between about 1% to 10% trehalose, or between about 3% to 7% trehalose; with between about 0.5% to 1.5% NaCl, or between about 0.7% to 1.2% NaCl; and with between about 0.005% and 1% polysorbate, or between about 0.01% and 0.5% polysorbate; or, a mixture of about 5% trehalose with about 0.9% NaCl and about 0.01% polysorbate 80; or (g) between about 1% to 10% trehalose, or between about 3% to 7% trehalose; with between about 1% to 10% mannitol, or between about 3% to 7% mannitol; with between about 0.5% to 1.5% NaCl, or between about 0.7% to 1.2% NaCl; and with between about 0.005% and 1% polysorbate, or between about 0.01% and 0.5% polysorbate; or, a mixture of about 5% trehalose and about 5% mannitol with about 0.9% NaCl and about 0.01% polysorbate 80.

In alternative embodiments of the pharmaceutical compositions provided herein, the lyophilized, cryodesiccated, freeze-dried or dehydrated bacterial flora is formulated with a composition or mixture comprising:

(a) 10% trehalose with 2.5% sucrose, 0.9% NaCl;
(b) 10% trehalose with 2.5% sucrose, 0.9% NaCl and 0.01% polysorbate 80;
(c) <10% trehalose with 2.5% sucrose and 0.9% NaCl;
(d) <5% mannitol with 0.9% NaCl and 0.01% polysorbate 80;
(e) approximately 10% mannitol with 0.9% NaCl and 0.01% polysorbate 80;
(f) <5% trehalose with 0.9% NaCl and 0.01% polysorbate 80;
(g) approximately 5% trehalose and 5% mannitol with 0.9% NaCl and 0.01% polysorbate 80;
(h) 10% trehalose with 2.5% sucrose, 0.9% NaCl and 0.01% polysorbate 80;
(i) <10% trehalose with 2.5% sucrose and 0.9% NaCl;
(j) approximately 10% mannitol with 0.9% NaCl and 0.01% polysorbate 80;
(k) <5% trehalose and 5% mannitol with 0.9% NaCl and 0.01% polysorbate 80;
(i) <5% trehalose with 0.9% NaCl and 0.01% polysorbate 80; or
(j) <5% mannitol with 0.9% NaCl and 0.01% polysorbate 80.

In alternative embodiments of the pharmaceutical compositions provided herein, the pharmaceutical compositions are manufactured, labelled or formulated for human or animal use, and optionally the animal use is for a veterinary use.

In alternative embodiments, the pharmaceutical compositions provided herein are further processed or manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation.

In alternative embodiments, provided herein are delivery vehicles, products of manufacture, containers or devices comprising a pharmaceutical composition as provided herein, optionally formulated for or calibrated for repeat or multiple implantations, administration, delivery or infusions.

In alternative embodiments, provided herein are delivery vehicles, products of manufacture, containers or devices, further comprising one or more of: an additive, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent, coloring agent, at least one vitamin, mineral and/or dietary supplement, or a prebiotic nutrient.

In alternative embodiments, provided herein are methods for making a pharmaceutical composition comprising a lyophilized, cryodesiccated, freeze-dried or dehydrated bacterial flora, comprising:

(a) providing a composition, isolate or preparation comprising, or consisting essentially of, or consisting of:

an entire (or substantially entire) fecal microbiota, optionally isolated and/or stored in a partially, substantially or completely anaerobic environment, a treated or untreated fecal flora sample, a complete or partial fecal flora sample, optionally isolated and/or stored in a partially, substantially or completely anaerobic environment, a fecal flora substantially or completely purified of non-fecal floral fecal material, wherein optionally the fecal flora is separated from a rough particulate matter in a fecal sample by: homogenizing, centrifuging and/or filtering a rough particulate matter or a non-floral matter of the fecal material, or by plasmapheresis, centrifugation, celltrifuge, column chromatography or by immunoprecipitation, and optionally the substantially or completely purified fecal flora has no greater than about 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material, a partially, substantially or completely isolated or purified fecal flora or fecal flora filtrate, wherein optionally the purification process comprises filtering a fecal sample with a filter medium, wherein optionally the filter medium includes at least one sieve size of no greater than about 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, or 0.01 mm, or a sieve size of 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm, to result in or to generate a filtrate, a disease screened fresh homologous feces, optionally substantially or completely purified of non-fecal floral fecal material, or optionally isolated and/or stored in a partially, substantially or completely anaerobic environment, and optionally the fecal flora is initially derived from an individual screened or tested for a disease or an infection, and/or the fecal flora is initially derived from an individual screened to have a normal, healthy or wild type population of fecal flora, a reconstituted feces, optionally reconstituted using cultured viable non-pathogenic or attenuated microorganisms, a synthetic fecal composition of predetermined flora, a synthetic or reconstituted fecal composition comprising a preparation of viable flora in proportional content that resembles a normal healthy human fecal flora, which does not include antibiotic resistant populations, a composition comprising viable, non-pathogenic colonic bacterial cells selected from the group consisting of a *Clostridia*, a *Collinsella*, a *Bacteroides*, a *Fusobacteria*, a *Propionibacteria*, a *Lactobacilli*, an anaerobic cocci, a *Ruminococcus*, an *E. coli*, a *Gemmiger*, a *Desulfomonas*, a *Peptostreptococcus*, a *Bifidobacteria* and any combination thereof;

a composition comprising viable, non-pathogenic colonic bacterial components of fecal flora, wherein the bacterial components comprise *Clostridium bifermentans, Clostridium innocuum, Clostridium butyricum, Escherichia coli, Bacteroides* and *Peptostreptococcus productus,* a composition comprising viable, non-pathogenic colonic bacterial components of fecal flora, wherein the bacterial components comprise a *Bacteroides*, an *Escherichia coli*, and a non-pathogenic *Clostridia*, wherein optionally the non-pathogenic *Clostridia* comprise a *Clostridium innocuum*, a *Clostridium bifermentans* and a *Clostridium ramosum,* a composition comprising a plurality of viable non-pathogenic *Clostridia* and a plurality of viable non-pathogenic *Collinsella*, and optionally with no viable *Lactobacilli, Bifidobacteria* or *Eubacteria*, and optionally with no viable *Bacteroides, Fusobacteria, Propionibacteria, Lactobacilli,* anaerobic cocci, *Ruminococcus, E. coli, Gemmiger, Desulfomonas, Peptostreptococcus* or *Bifidobacteria,* a composition comprising a plurality of viable non-pathogenic *Clostridia*, wherein optionally the plurality of viable non-pathogenic *Clostridia* comprise non-pathogenic *Clostridia* spores, a composition comprising a plurality of viable non-pathogenic *Clostridia* and a plurality of viable non-pathogenic *Collinsella*, wherein optionally the plurality of viable non-pathogenic *Clostridia* comprise non-pathogenic *Clostridia* spores and/or the plurality of viable non-pathogenic *Clostridia* comprise non-pathogenic *Collinsella* spores, wherein optionally the plurality of viable non-pathogenic *Clostridia* and are from a first pure culture and the plurality of viable non-pathogenic *Collinsella* cells from a second pure culture, and/or a composition comprising viable non-pathogenic *Clostridia* spores, a viable non-pathogenic *Bacteroides*, and a viable non-pathogenic *Escherichia coli,* wherein optionally the composition, isolate or preparation has at least about $10^9$ viable cells cells/g, $10^{10}$ viable cells cells/g, $10^{12}$ viable cells cells/g, $10^{13}$ viable cells cells/g, or $10"$ viable cells cells/g, or between about $10^8$ and $10^{14}$ viable cells cells/g, or between about $10^{10}$ and $10^{12}$ viable cells cells/g;

(b) providing a cryoprotectant and optionally a surfactant or an emulsifier, wherein optionally the cryoprotectant comprises: a dimethyl sulfoxide (DMSO) or equivalent; a glycerol, a polyethylene glycol (PEG) or equivalent; a polysaccharide; a sugar, or an amino acid, wherein optionally the amino acid comprises an alanine, a glycine, a proline, or the sugar comprises a mannitol, a sucrose, a glucose, a lactose, a ribose or trehalose, or the polysaccharide comprises a hydroxypropyl-β-cyclodextrin (HPβCD), or the cryoprotectant comprises any combination of different cryoprotectant compounds, wherein optionally the surfactant or emulsifier comprises a polysorbate (polyoxyethylene sorbitan monolaurate) or a PEG-ylated sorbitan, optionally a Polysorbate 80 (polyoxyethylene (80) sorbitan monolaurate);

(c) homogenizing the composition, isolate or preparation of (a) with a mixture of saline and cryoprotectant, or with a mixture of saline, cryoprotectant and a surfactant or an emulsifier, wherein optionally the homogenization is about 1:2, 1:3, 1:4 or 1:5 (w/w) with a solution comprising saline, and optionally the cryoprotectant is present at a concentration of at least 1%, 2%, 3%, 4%, 5%, 6%, 7%, 8%, 9%, or 10% (vol/vol);

(d) lyophilizing, cryodesiccating, freeze-drying or dehydrating the homogenized composition, isolate or preparation mixture of (c), wherein optionally after the lyophilizing, cryo-desiccating, freeze-drying or dehydrating the final water activity (aw) is less than about 0.1, 0.2, 0.3 or 0.4; and (e) storing, keeping and/or maintaining the lyophilized, cryo-desiccated, freeze-dried or dehydrated composition, isolate or preparation at ambient temperature, room temperature, approximately room temperature, or at between about 15° C. to 26° C., or at about 20° C., 21° C., 22° C., 23° C., 24° C., 25° C., 26° C., 27° C. or 28° C., wherein optionally the stored pharmaceutical composition has at least about $10^8$ viable cells cells/g, $10^9$ viable cells cells/g, $10^{10}$ viable cells cells/g, $10^{12}$ viable cells cells/g, $10^{13}$ viable cells cells/g, or $10^{14}$ viable cells cells/g, or between about $10^7$ and $10^{12}$ viable cells cells/g, or between about $10^9$ and $10^{11}$ viable cells cells/g.

In alternative embodiments of the methods, the lyophilized, cryodesiccated, freeze-dried or dehydrated bacterial flora are formulated with a composition or mixture comprising:

(a) between about 8% to 12% trehalose, or between about 9% to 11% trehalose; with between about 2.0% to 3.0% sucrose, or between about 1.5% to 3.5% sucrose; with between about 0.5% to 1.5% NaCl, or between about 0.7% to 1.2% NaCl; or, a mixture of about 10% trehalose with about 2.5% sucrose and about 0.9% NaCl;

(b) between about 8% to 12% trehalose, or between about 9% to 11% trehalose; with between about 2.0% to 3.0% sucrose, or between about 1.5% to 3.5% sucrose; with between about 0.5% to 1.5% NaCl, or between about 0.7% to 1.2% NaCl; and with between about 0.005% and 1% polysorbate, or between about 0.01% and 0.5% polysorbate; or, a mixture of about 10% trehalose with about 2.5% sucrose, about 0.9% NaCl and about 0.01% polysorbate 80;

(c) between about 1% to 10% trehalose, or between about 3% to 7% trehalose; with between about 0.5% to 1.5% NaCl, or between about 0.7% to 1.2% NaCl; and with between about 0.005% and 1% polysorbate, or between about 0.01% and 0.5% polysorbate; or, a mixture of about 5% trehalose with about 0.9% NaCl and about 0.01% polysorbate 80;

(d) between about 8% to 12% mannitol, or between about 9% to 11% mannitol; with between about 0.5% to 1.5% NaCl, or between about 0.7% to 1.2% NaCl; and with between about 0.005% and 1% polysorbate, or between about 0.01% and 0.5% polysorbate; or, a mixture of about 10% mannitol with about 0.9% NaCl and about 0.01% polysorbate 80;

(e) between about 1% to 10% mannitol, or between about 3% to 7% mannitol; with between about 0.5% to 1.5% NaCl, or between about 0.7% to 1.2% NaCl; and with between about 0.005% and 1% polysorbate, or between about 0.01% and 0.5% polysorbate; or, a mixture of about 5% mannitol with about 0.9% NaCl and about 0.01% polysorbate 80; or (f) between about 1% to 10% trehalose, or between about 3% to 7% trehalose; with between about 0.5% to 1.5% NaCl, or between about 0.7% to 1.2% NaCl; and with between about 0.005% and 1% polysorbate, or between about 0.01% and 0.5% polysorbate; or, a mixture of about 5% trehalose with about 0.9% NaCl and about 0.01% polysorbate 80; or (g) between about 1% to 10% trehalose, or between about 3% to 7% trehalose; with between about 1% to 10% mannitol, or between about 3% to 7% mannitol; with between about 0.5% to 1.5% NaCl, or between about 0.7% to 1.2% NaCl; and with between about 0.005% and 1% polysorbate, or between about 0.01% and 0.5% polysorbate; or, a mixture of about 5% trehalose and about 5% mannitol with about 0.9% NaCl and about 0.01% polysorbate 80.

In alternative embodiments of the methods provided herein, the lyophilized, cryodesiccated, freeze-dried or dehydrated bacterial flora is formulated with a composition or mixture comprising:

(a) 10% trehalose with 2.5% sucrose, 0.9% NaCl;

(b) 10% trehalose with 2.5% sucrose, 0.9% NaCl and 0.01% polysorbate 80;

(c) <10% trehalose with 2.5% sucrose and 0.9% NaCl;

(d) <5% mannitol with 0.9% NaCl and 0.01% polysorbate 80;

(e) approximately 10% mannitol with 0.9% NaCl and 0.01% polysorbate 80;

(0 <5% trehalose with 0.9% NaCl and 0.01% polysorbate 80;

(g) approximately 5% trehalose and 5% mannitol with 0.9% NaCl and 0.01% polysorbate 80;

(h) 10% trehalose with 2.5% sucrose, 0.9% NaCl and 0.01% polysorbate 80;

(i) <10% trehalose with 2.5% sucrose and 0.9% NaCl;

(j) approximately 10% mannitol with 0.9% NaCl and 0.01% polysorbate 80;

(k) <5% trehalose and 5% mannitol with 0.9% NaCl and 0.01% polysorbate 80;

(i) <5% trehalose with 0.9% NaCl and 0.01% polysorbate 80; or (j) <5% mannitol with 0.9% NaCl and 0.01% polysorbate 80.

In alternative embodiments of the methods provided herein, the pharmaceutical composition is manufactured, labelled or formulated for human or animal use, and optionally the animal use is for a veterinary use.

In alternative embodiments of the methods provided herein, the pharmaceutical composition is further processed or manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation.

In alternative embodiments of the methods provided herein, the pharmaceutical composition is formulated for or calibrated for repeat or multiple implantations, administration, delivery or infusions.

In alternative embodiments of the methods provided herein the pharmaceutical composition further comprises one or more of: an additive, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent, coloring agent, at least one vitamin, mineral and/or dietary supplement, or a prebiotic nutrient.

In alternative embodiments provided are methods for delivering or administering a Fecal Microbiota Transplantation (FMT), or a lyophilized, cryo-desiccated, freeze-dried or dehydrated bacterial flora, to an individual in need thereof, comprising administering a pharmaceutical composition as provided herein, or a pharmaceutical composition made by a method as provided herein, wherein the storing, keeping and/or maintaining the lyophilized, cryo-desiccated, freeze-dried or dehydrated composition, isolate or preparation at ambient temperature, room temperature, approximately room temperature, or at between about 15° C. to 26° C., or at about 20° C., 21° C., 22° C., 23° C., 24° C., 25° C., 26° C., 27° C. or 28° C., wherein optionally the stored pharmaceutical composition has at least about $10^8$ viable cells cells/g, $10^9$ viable cells cells/g, $10^{10}$ viable cells cells/g, $10^{12}$ viable cells cells/g, $10^{13}$ viable cells cells/g, or $10^{14}$ viable cells cells/g, or between about $10^7$ and $10^{12}$ viable cells cells/g, or between about $10^9$ and $10^{11}$ viable cells cells/g.

In alternative embodiments provided are pharmaceutical compositions comprising lyophilized, cryodesiccated, freeze-dried or dehydrated microflora material from a formulation selected from the group consisting of:

(a) between about 8% to 12% trehalose, or between about 9% to 11% trehalose; with between about 2.0% to 3.0% sucrose, or between about 1.5% to 3.5% sucrose; with between about 0.5% to 1.5% NaCl, or between about 0.7% to 1.2% NaCl; or, a mixture of 10% trehalose with 2.5% sucrose and 0.9% NaCl;

(b) between about 8% to 12% trehalose, or between about 9% to 11% trehalose; with between about 2.0% to 3.0% sucrose, or between about 1.5% to 3.5% sucrose; with between about 0.5% to 1.5% NaCl, or between about 0.7% to 1.2% NaCl; and with between about 0.005% and 1% polysorbate, or between about 0.01% and 0.5% polysorbate; or, a mixture of 10% trehalose with 2.5% sucrose, 0.9% NaCl and 0.01% polysorbate 80;

(c) between about 1% to 10% trehalose, or between about 3% to 7% trehalose; with between about 0.5% to 1.5% NaCl, or between about 0.7% to 1.2% NaCl; and with between about 0.005% and 1% polysorbate, or between about 0.01% and 0.5% polysorbate; or, a mixture of 5% trehalose with 0.9% NaCl and 0.01% polysorbate 80;

(d) between about 8% to 12% mannitol, or between about 9% to 11% mannitol; with between about 0.5% to 1.5% NaCl, or between about 0.7% to 1.2% NaCl; and with between about 0.005% and 1% polysorbate, or between about 0.01% and 0.5% polysorbate; or, a mixture of 10% mannitol with 0.9% NaCl and 0.01% polysorbate 80;

(e) between about 1% to 10% mannitol, or between about 3% to 7% mannitol; with between about 0.5% to 1.5% NaCl, or between about 0.7% to 1.2% NaCl; and between about 0.005% and 1% polysorbate, or between about 0.01% and 0.5% polysorbate; or, a mixture of 5% mannitol with 0.9% NaCl and 0.01% polysorbate 80; or (f) between about 1% to 10% trehalose, or between about 3% to 7% trehalose; with between about 0.5% to 1.5% NaCl, or between about 0.7% to 1.2% NaCl; and with between about 0.005% and 1% polysorbate, or between about 0.01% and 0.5% polysorbate; or, a mixture of about 5% trehalose with 0.9% NaCl and 0.01% polysorbate 80; or (g) between about 1% to 10% trehalose, or between about 3% to 7% trehalose; with between about 1% to 10% mannitol, or between about 3% to 7% mannitol; with between about 0.5% to 1.5% NaCl, or between about 0.7% to 1.2% NaCl; and with between about 0.005% and 1% polysorbate, or between about 0.01% and 0.5% polysorbate; or, a mixture of 5% trehalose and 5% mannitol with 0.9% NaCl and 0.01% polysorbate 80; or, a) <10% trehalose with 2.5% sucrose and 0.9% NaCl;
b) 10% mannitol with 0.9% NaCl and 0.01% polysorbate 80;
c) 5% mannitol with 0.9% NaCl and 0.01% polysorbate 80;
d) <5% mannitol with 0.9% NaCl and 0.01% polysorbate 80;
e) approximately 10% mannitol with 0.9% NaCl and 0.01% polysorbate 80;
f) 5% trehalose with 0.9% NaCl and 0.01% polysorbate 80;
g) <5% trehalose with 0.9% NaCl and 0.01% polysorbate 80;
h) 5% trehalose and 5% mannitol with 0.9% NaCl and 0.01% polysorbate 80
i) approximately 5% trehalose and 5% mannitol with 0.9% NaCl and 0.01% polysorbate 80;
j) 10% trehalose with 2.5% sucrose, 0.9% NaCl and 0.01% polysorbate 80;
k) <10% trehalose with 2.5% sucrose and 0.9% NaCl;
l) approximately 10% mannitol with 0.9% NaCl and 0.01% polysorbate 80;
m) <5% trehalose and 5% mannitol with 0.9% NaCl and 0.01% polysorbate 80;
n) <5% trehalose with 0.9% NaCl and 0.01% polysorbate 80; and
o) <5% mannitol with 0.9% NaCl and 0.01% polysorbate 80;

the microflora material comprising, or consisting essentially of, or consisting of a) an entire (or substantially entire) fecal microbiota, optionally isolated and/or stored in a partially, substantially or completely anaerobic environment,
b) a treated or untreated fecal flora sample,
c) a complete or partial fecal flora sample, optionally isolated and/or stored in a partially, substantially or completely anaerobic environment,
d) a fecal flora substantially or completely purified of non-fecal floral fecal material, wherein optionally the fecal flora is separated from a rough particulate matter in a fecal sample by: homogenizing, centrifuging and/or filtering a rough particulate matter or a non-floral matter of the fecal material, or by plasmapheresis, centrifugation, celltrifuge, column chromatography or by immunoprecipitation, and optionally the substantially or completely purified fecal flora has no greater than about 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material,
e) a partially, substantially or completely isolated or purified fecal flora or fecal flora filtrate, wherein optionally the purification process comprises filtering a fecal sample with a filter medium, wherein optionally the filter medium includes at least one sieve size of no greater than about 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, or 0.01 mm, or a sieve size of 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm, to result in or to generate a filtrate, f) a disease screened fresh homologous feces, optionally substantially or completely purified of non-fecal floral fecal material, or optionally isolated and/or stored in a partially, substantially or completely anaerobic environment, and optionally the fecal flora is initially derived from an individual screened or tested for a disease or an infection, and/or the fecal flora is initially derived from an individual screened to have a normal, healthy or wild type population of fecal flora, g) a reconstituted feces, optionally reconstituted using cultured viable non-pathogenic or attenuated microorganisms, h) a synthetic fecal composition of predetermined flora, i) a synthetic or reconstituted fecal composition comprising a preparation of viable flora in proportional content that resembles a normal healthy human fecal flora, which does not include antibiotic resistant populations, j) a composition comprising viable, non-pathogenic colonic bacterial cells selected from the group consisting of a *Clostridia*, a *Collinsella*, a *Bacteroides*, a *Fusobacteria*, a *Propionibacteria*, a *Lactobacilli*, an anaerobic cocci, a *Ruminococcus*, an *E. coli*, a *Gemmiger*, a *Desulfomonas*, a *Peptostreptococcus*, a *Bifidobacteria* and any combination thereof;

k) a composition comprising viable, non-pathogenic colonic bacterial components of fecal flora, wherein the bacterial components comprise *Clostridium bifermentans*, *Clostridium innocuum*, *Clostridium butyricum*, *Escherichia coli*, *Bacteroides* and *Peptostreptococcus productus*, l) a composition comprising viable, non-pathogenic colonic bacterial components of fecal flora, wherein the bacterial components comprise a *Bacteroides*, an *Escherichia coli*, and a non-pathogenic *Clostridia*, wherein optionally the non-pathogenic *Clostridia* comprise a *Clostridium innocuum*, a *Clostridium bifermentans* and a *Clostridium ramosum*, m) a composition comprising a plurality of viable non-pathogenic *Clostridia* and a plurality of viable non-pathogenic *Collinsella*, and optionally with no viable *Lactobacilli*, *Bifidobacteria* or *Eubacteria*, and optionally with no viable *Bacteroides*, *Fusobacteria*, *Propionibacteria*, *Lactobacilli*, anaerobic cocci, *Ruminococcus*, *E. coli*, *Gemmiger*, *Desulfomonas*, *Peptostreptococcus* or *Bifidobacteria*, n) a composition comprising a plurality of viable non-pathogenic *Clostridia*, wherein optionally the plurality of viable non-pathogenic *Clostridia* comprise non-pathogenic *Clostridia* spores, o) a composition comprising a plurality of viable non-pathogenic *Clostridia* and a plurality of viable non-pathogenic *Collinsella*, wherein optionally the plurality of viable non-pathogenic *Clostridia* comprise non-pathogenic *Clostridia* spores and/or the plurality of viable non-pathogenic *Clostridia* comprise non-pathogenic *Collinsella* spores, wherein optionally the plurality of viable non-pathogenic *Clostridia* and are from a first pure culture and the plurality of viable non-pathogenic *Collinsella* cells from a second pure culture, and/or p) a composition comprising viable non-pathogenic *Clostridia* spores, a viable non-pathogenic *Bacteroides*, and a viable non-pathogenic *Escherichia coli*, q) wherein optionally the composition, isolate or preparation has at least about $10^9$ viable cells cells/g, $10^{10}$ viable cells cells/g, $10^{12}$ viable cells cells/g, $10^{13}$ viable cells cells/g, or $10^{14}$ viable cells cells/g, or between about $10^8$ and $10^{14}$ viable cells cells/g, or between about $10^{10}$ and $10^{12}$ viable cells cells/g.

In alternative embodiments, the pharmaceutical compositions are formulated in a gastric acid resistant capsule.

In alternative embodiments provided are methods for treating a disorder in a subject in need thereof, the method comprising administering to the subject an amount of the pharmaceutical composition of claim 18 effective for treating the disorder, wherein the disorder is selected from the group consisting of recurrent *C. diff.* infection, autism, constipation predominant functional bowel disease (FBD), pain predominant FBD, upper abdominal FBD, non-ulcer dyspepsia (NUD), gastro-oesophageal reflux, indeterminate colitis, microscopic colitis, pseudomembranous colitis, viral gastroenteritis, Norwalk viral gastroenteritis, rotavirus gastroenteritis, AIDS related gastroenteritis, non rheumatoid factor positive arthritis, Lyme disease, systemic lupus, idiopathic thrombocytopenic purpura, Sjogren's syndrome, haemolytic uremic syndrome or scleroderrna, Gillain-Barre syndrome, Chronic Inflammatory Demyelinating Polyneuropathy, chronic depression, schizophrenia, psychotic disorders, manic depressive illness, Asbergers syndrome, Rett syndrome, attention deficit hyperactivity disorder (ADHD), and attention deficit disorder (ADD), sudden infant death syndrome (SIDS), anorexia nervosa.

In alternative embodiments provided are methods comprising storing the pharmaceutical composition as provided herein at ambient temperature, room temperature, approximately room temperature, or at between about 15° C. to 26° C., or at about 20° C., 21° C., 22° C., 23° C., 24° C., 25° C., 26° C., 27° C. or 28° C.; and optionally, at least 50%, at least 55%, at least 60%, at least 65%, at least 70%, at least 75%, at least 80%, at least 85%, at least 90%, or at least 95% microbial viability of the microflora material of the pharmaceutical composition is maintained, or between about 40% and 95% of the microflora material of the pharmaceutical composition is maintained, after about 2, about 4, about 8, about 12, about 20, about 30, about 40, about 50, or about 60 weeks of storage from (after) preparation of the pharmaceutical composition, or after between about 2 to 60 weeks from (after) preparation of the pharmaceutical composition. or after between about 1 to 12 months, or 2 to 24 months, from (after) preparation of the pharmaceutical composition.

In alternative embodiments, provided are methods and compositions facilitating prolonged viability or longer term survival of FMT, e.g., filtered fecal microbiota, at e.g., ambient temperatures, e.g., at room temperatures (including storage, including long term storage at ambient temperatures, e.g., at room temperatures); and while the invention is not limited by any particular mechanism of action, this prolonged viability or longer term survival can be achievable through the use of a cryoprotectant and/or a mix of cryoprotectants at various mix compositions, thus, storage at ambient temperature (e.g., prolonged shelf-life in pharmacy or home) may be achieved. In alternative embodiments, the cryoprotectants and associated liquids include trehalose, sucrose, normal saline, mannitol, and polysorbate(s), e.g., a polysorbate 80, in various combinations.

In alternative embodiments, provided are compositions having the ability to isolate, prepare, formulate and/or reduce the volume of the FMT product so as to store it in a delivery system, e.g., as a bottle-top of a drink, e.g., a chocolate drink, as a side compartment of yoghurt, or a two-layered aluminized top of ice-cream tub for kids, e.g., for autism, and methods of preparation of same.

In alternative embodiments, provided are compositions prepared and/or formulated in a powdered form, or equivalent; these formulations can be useful for storage in e.g., a tablet or capsule, or in an ampoule to e.g., crack open and dissolve in a liquid for, e.g., insertion, mixing or injection into e.g. a channel of a colonoscope or a naso-enteric tube, and the like; or as a powder in a bag ready to add e.g., as a solution which can be e.g., infused into an NG tube (or equivalent), or a colonoscope, or a gastroscope for e.g., stoma gastrostomy, or a PEG tube.

In alternative embodiments, provided are freeze dried or lyophilized materials, which can be formulated or manufactured into or as an edible or friable product, e.g., a biscuit-like product, which can be e.g., crushed into a powder to dissolve in a drink or to insert into a tablet or a capsule. In alternative embodiments, provided are FMT-comprising formulations that are orally ingestible, or can be a rectally applied product. In alternative embodiments, provided are FMT-comprising formulations in the form of a dry lozenge or a chewing gum or equivalent. In alternative embodiments, use of all of these formulations, foods, drinks, and products of manufacture are facilitated by the ability to manufacture, ship and store at room temperature or at an ambient temperature, as provided by this invention.

In alternative embodiments, provided herein are compositions, e.g., formulations and pharmaceutical preparations, products of manufacture, and containers and delivery vehicles, and devices and delivery materials, comprising treated and/or isolated faecal (fecal) material for faecal floral transplantation. In one embodiment, the treated and/or isolated fecal material provided herein comprise faecal floral (e.g., bacteria) transplanted between different individuals, e.g., human to human or between animals. In one embodiment, the treated fecal material provided herein is transplanted back into the same individual from which it was collected, e.g., to repopulate a colon after drug treatment (e.g., antibiotic treatment or chemotherapy) or after an orthostatic lavage, e.g., for inducing the purgation (e.g., cleansing) of a gastrointestinal (GI) tract, including a colon.

In alternative embodiments, compositions, e.g., formulations and pharmaceutical preparations, products of manufacture, and containers and delivery vehicles, and devices and delivery materials provided herein are used for the amelioration, stabilization, or treatment of a bowel disease or infection comprising use of a delivery vehicle, formulation, product of manufacture, or container or device provided herein; e.g., as a fecal bacteriotherapy, fecal transfusion, fecal transplant, or human probiotic infusion (HPI). In alternative embodiments, provided herein are methods for using compositions provided herein for e.g., ameliorating, stabilizing, treating or preventing any infection, bowel disease or condition having a bowel dysfunction component, for example, a poisoning, a pseudomembranous colitis, a *Clostridium difficile* infection, an inflammatory bowel disease (IBD), Crohn's disease, hepatic encephalopathy, enteritis, colitis, irritable bowel syndrome (IBS), fibromyalgia (FM), alopecia areata/totalis, anorexia nervosa, autism, chronic fatigue syndrome (CFS), depression, attention deficit/hyperactivity disorder (ADHD), multiple sclerosis (MS), systemic lupus erythematosus (SLE), travellers' diarrhea, small intestinal bacterial overgrowth, chronic pancreatitis, or a pancreatic insufficiency.

For example, in one embodiment, as antibiotics do not eradicate *C. difficile* and its spore, a delivery vehicle, formulation, product of manufacture, or container or device as provided herein, e.g., comprise treated and/or isolated fecal flora for use to ameliorate, stabilize or eradicate *C. difficile* (or the pseudo-membranous colitis associated with this infection) when infused into a colon of the infected or ill individual, e.g., a patient or animal. In alternative embodiments the fecal flora obtained from a donor comprises a part of, substantially all of, or all of the infected or ill recipient's missing or inadequate (e.g., in numbers or function) fecal flora, e.g., bacteria. While the invention is not limited by any particular mechanism of action, in some embodiments it is the transfer of the equivalent of: a part of, substantially all of, or all of the fecal flora of the infected individual from the donor to the recipient (e.g., from human to human) that ameliorates or eradicates the infection or the pseudo-membranous colitis associated with this infection.

In alternative embodiments, the compositions, e.g., formulations and pharmaceutical preparations, and devices, delivery materials, delivery vehicles, products of manufacture, containers and devices provided herein allow the safe transplantation of fecal flora (e.g., human flora) components to individuals in need thereof, e.g., to infected, sick and dying patients, thus providing a consistently safe yet functioning flora for delivery to a recipient or patient.

In alternative embodiments, provided herein is a reliable method for producing standardized fresh fecal flora which can have a long shelf life. In one embodiment, the delivery vehicle, formulation, pharmaceutical preparation, product of manufacture, container or device comprising the fecal flora comprises a substantially or completely oxygen-free environment. In another embodiment, nutrients such as "prebiotic nutrients" can be added (e.g., in dry or liquid forms) to a composition provided herein. A prebiotic nutrient can be any ingredient that stimulates the stability, growth and/or activity of the fecal flora, e.g., bacteria; for example, in alternative embodiments, polyols, fructooligosaccharides (FOSs), oligofructoses, inulins, galactooligosaccharides (GOSs), xylooligosaccharides (XOSs), polydextroses, monosaccharides such as tagatose, and/or mannooligosaccharides are used as prebiotics to practice this invention. In one embodiment, the prebiotics are added to prevent "shock" to the fecal flora subsequent to their isolation or purification, freezing, freeze-drying, spray-drying, reconstitution in solution and the like.

In alternative embodiments, components of the compositions, e.g., delivery vehicles, formulations and pharmaceutical preparations, products of manufacture, or containers or devices, provided herein comprise an entire (or substantially entire) microbiota, or a *Bacteroides* and/or *Firmicutes* in large numbers (e.g., a larger proportion of *Bacteroides* and/or *Firmicutes* is present that is normally found in situ), e.g., to be able to ameliorate and/or eradicate a *C. difficile* infection and/or the pseudo-membranous colitis associated with this infection. In alternative embodiments, the compositions, e.g., delivery vehicles, formulations and pharmaceutical preparations, products of manufacture, or containers or devices, provided herein can be available (e.g., formulated and/or dosaged for) for recurrent use in individuals, e.g., in patients or animals, with the more difficult to treat conditions such as colitis (e.g., the pseudo-membranous colitis of a *C. difficile* infection) and constipation.

In alternative embodiments, components of the compositions e.g., delivery vehicles, formulations and pharmaceutical preparations, products of manufacture, or containers or devices, provided herein comprise a selection of bacterial species e.g. *Bacteroides, Firmicutes, Bacillus thuringiensis* (a bacterium capable of producing peptide antibiotics for *C. difficile*). The bacterial species may be separated by celltrifugation or plasmapheresis.

In alternative embodiments the selection of bacterial species e.g. *Bacteroides, Firmicutes, Bacillus thuringiensis* may be added to components of the compositions, e.g., delivery vehicles, formulations and pharmaceutical preparations, products of manufacture, or containers or devices as fortification of concentrations comprising the bacterial species to contain wild types of bacteria.

In alternative embodiments, compositions provided herein can be re-formulated as fecal slurries, saline or buffered suspensions (e.g., for an enema, suspended in a buffer or a saline), in a drink (e.g., a milk, yoghurt, a shake, a flavoured drink or equivalent) for oral delivery, and the like.

In alternative embodiments, compositions provided herein can be formulated or re-formulated as an enema product, a spray dried product, reconstituted enema, a small capsule product, a small capsule product suitable for administration to children, a bulb syringe, a bulb syringe suitable for a home enema with a saline addition, a powder product, a powder product in oxygen deprived sachets, a powder product in oxygen deprived sachets that can be added to, for example, a bulb syringe or enema, or a spray dried product in a device that can be attached to a container with an appropriate carrier medium such as yoghurt or milk and that can be directly incorporated and given as a dosing for example for children.

In one embodiment, compositions provided herein can be delivered directly in a carrier medium via a screw-top lid wherein the fecal material is suspended in the lid and released on twisting the lid straight into the carrier medium.

In alternative embodiments provided herein include fecal slurries formulated for insertion/administration into the bowel, e.g., via an enema suspended in saline or a buffer, orally in a drink (e.g., a milk, yoghurt, a flavoured drink and the like), via a small bowel infusion via a nasoduodenal tube, via a gastrostomy, or by using a colonoscope. In some embodiment, there may be advantages delivering via a colonoscope to infuse as proximally as possible, and to detect any colonic pathology.

In alternative embodiments methods, fecal flora used in compositions provided herein are initially derived (entirely or in part) from an individual screened or tested for a disease or infection, and/or the fecal flora is initially derived from an individual screened to have a normal, healthy or normal, representative "wild type" population of fecal flora; e.g., a normal complement of a *Bacteroides* and/or *Firmicutes*, and/or other fecal flora such as *Bacillus Thuringiensis*. In one embodiment, depending on a deficiency of a floral (e.g., bacterial) specie or species in a donor fecal material, or to achieve a desired effect, one or more additional (or "supplemental") species, e.g., *Bacteroides, Firmicutes* and/or *Bacillus Thuringiensis* species, is added to (or is administered with) the delivered product either initially when the product is made, or at the time of delivery, e.g., the additional species is/are mixed in before application to the individual (e.g., patient or animal), e.g., when a powder, lyophilate, or freeze-dried composition is reconstituted for delivery; or the one or more additional (or "supplemental") species can be co-administered. These additional floral species can be directly isolated or purified from a donor, or can be expanded (cultured) for a time in vitro before addition, or can come from (be derived from) a pure culture, e.g., from an ATTC stock. For example, in some applications, e.g., to achieve a desired effect or therapeutic outcome, a delivery of an enhanced amount of one or more fecal flora (e.g., bacterial) species is used, e.g., the delivered product (e.g., an entire (or substantially entire) microbiota, or a composition comprising a complete or partial fecal flora, or a partially, substantially or completely isolated or purified fecal flora) is enhanced with (is "spiked" with") one or more additional (or "supplemental") species, e.g., *Bacteroides, Firmicutes* and/ or *Bacillus Thuringiensis* species, which can be directly isolated from a donor, or can come from a pure culture, and the like.

In some embodiments, selection of the donor is of crucial importance, e.g., to avoid infecting the recipient with a separate infection or disease. In alternative embodiments the donor is tested (screened) at least for e.g., retrovirus (e.g., human immunodeficiency virus, HIV); hepatitis A, B, and/or C; cytomegalovirus; Epstein-Barr virus, detectable parasites and/or bacterial pathogens, depending on the specie of the donor and recipient, e.g., human or animal.

In alternative embodiments, provided herein is a process for preparing fecal flora (e.g., an entire (or substantially entire) microbiota) for transplantation, first comprising a collection from one or more healthy (e.g., screened) donor (s). In alternative embodiments, a fresh stool is transported via a stool collection device, which can provide or comprises a suitably oxygen free (or substantially oxygen free) appropriate container. In alternative embodiments, the container can be made oxygen free by e.g., incorporating into the container a built in or clipped-on oxygen-scavenging mechanism, e.g., oxygen scavenging pellets as described e.g., in U.S. Pat. No. 7,541,091. In another embodiment, the container itself is made of an oxygen scavenging material, e.g., oxygen scavenging iron, e.g., as described by O2BLOCK™, or equivalents, which uses a purified and modified layered clay as a performance-enhancing carrier of oxygen-scavenging iron; the active iron is dispersed directly in the polymer. In one embodiment, oxygen-scavenging polymers are used to make the container itself or to coat the container, or as pellets to be added; e.g., as described in U.S. Pat. App. Pub. 20110045222, describing polymer blends having one or more unsaturated olefinic homopolymers or copolymers; one or more polyamide homopolymers or copolymers; one or more polyethylene terephthalate homopolymers or copolymers; that exhibit oxygen-scavenging activity. In one embodiment, oxygen-scavenging polymers are used to make the container itself or to coat the container, or as pellets to be added; e.g., as described in U.S. Pat. App. Pub. 20110008554, describing compositions comprising a polyester, a copolyester ether and an oxidation catalyst, wherein the copolyester ether comprises a polyether segment comprising poly(tetramethylene-co-alkylene ether). In one embodiment, oxygen-scavenging polymers are used to make the container itself or to coat the container, or as pellets to be added; e.g., as described in U.S. Pat. App. Pub. 201000255231, describing a dispersed iron/salt particle in a polymer matrix, and an oxygen scavenging film with oxygen scavenging particulates.

Alternatively, in addition to or in place of the oxygen-scavenging mechanism, the air in the container can be replaced (completely or substantially) with nitrogen and/or other inert non-reactive gas or gases. In alternative embodiments, the container simulates (creates) partially, substantially or completely an anaerobic environment.

In alternative embodiments, the stool (e.g., fecal sample) is held in an aesthetically acceptable container that will not leak nor smell yet maintain an anaerobic environment. In alternative embodiments, the container is sterile before receiving the fecal flora.

In alternative embodiments, the compositions provided herein are maintained at room temperature during most or all of its preparation, transportation and/or storage at e.g., a "stool bank" or at the site where the transplantation will take place. For example, once delivered to a "processing stool bank" it is stored in at ambient temperature, e.g., room temperature.

In alternative embodiments, stabilizing agents such as glycerol are added to the harvested and/or stored material.

In alternative embodiments, the stool is tested for various pathogens, as noted above. In alternative embodiments, once cleared of infective agents, it is homogenized and filtered to remove large particles of matter. In alternative embodiments, it is subdivided into desired volumes, e.g., which can be between 5 cc and 3 or more liters. For example, in one embodiment, a container comprises a 50 gram (g) stool, which can be held in an appropriate oxygen resistant plastic, e.g., a metallized polyethylene terephthalate polyester film, or a metallized MYLAR™.

In alternative embodiments, the FMT material is subject to homogenization.

In alternative embodiments, compositions provided herein are placed into a container, e.g., a bag, that can be attached to a nasogastric or naso-duodenal tube to allow the contents to be infused e.g., into either a stomach, duodenum or the distal jejunum. Alternatively it can be kept in a container, e.g., a bag, which can be attached to an enema tip to be given as an enema.

In alternative embodiments, to separate the non-bacterial components and produce a product that can be lyophilized and have a long shelf life, the stool can be homogenized and filtered from rough particulate matter. In alternative embodiments, the microscopic fiber/nonliving matter is then separated from the bacteria. Several methods can be used, including e.g., recurrent filtration with filter sizes, e.g., coming down to the size of the bacterium.

In alternative embodiments, different filters are used to isolate bacterial spp., or a technique as used by Williams in WO 2011/033310A1, which uses a crude technique of filtration with a gauze.

In one embodiment, a filtration procedure for filtering whole stool is suitably used to reach the highest concentration of almost 100% bacteria. In one embodiment, the filtering procedure is a two-step procedure suitably using glass fibre depth filters for initial clarification. In one embodiment, the stool is filtered under positive pressure. In one embodiment, this would be using a combination or sandwich configuration with a 30 micron PVDF filter. In one embodiment, this sandwich procedure will be filtering the product under positive pressure. Later, membrane concentration can, in one embodiment, be used as another step to reduce the volume of the filtrate. In one embodiment, this can be done prior to freeze drying or spray drying under nitrogen cover.

Alternative membranes that can be used for filtration include, but not limited to, nylon filters, cellulose nitrate filters, polyethersulfone (PES) filters, polytetrafluorethylene (PTFE) filers, TEFLON™ filters, mixed cellulose Ester filters, polycarbonate filters, polypropylene filters, Polyvinylchloride (PVC) filters or quartz filters. Various combinations of these can be used to achieve a high purity of bacteria with solids and liquid removed ready for freezing, spray-drying or lyophilisation.

For freeze-drying, in alternative embodiments, bacteria are held in a liquid that will prevent bursting of cells on thawing. This can include various stabilizers, e.g., glycerol and appropriate buffers, and/or ethylene glycol. In alternative embodiments, cryo-protectance uses final concentrations of stabilizer(s) of between about 10% to 80%, 20% to 70%, 30% to 60%, or 40% to 50%, depending on the stabilizer(s) used; in alternative embodiments, this helps stabilize proteins by preventing formation of ice crystals that would otherwise destroy protein structures.

In alternative embodiments, the methods and compositions of the invention comprise use of one cryoprotectant or a mixture of cryoprotectants, e.g., comprising: a dimethyl sulfoxide (DMSO) or equivalent; a glycerol, a polyethylene glycol (PEG) or equivalent; a polysaccharide; a sugar, or an amino acid, wherein the amino acid can comprise an alanine, a glycine, a proline, or the sugar can comprise a mannitol, a sucrose, a glucose, a lactose, a ribose or trehalose, or the polysaccharide can comprise a hydroxypropyl-β-cyclodextrin (HPβCD), or the cryoprotectant can comprise any combination of different cryoprotectant compounds. In one embodiment, these cryoprotectants, e.g., trehalose, also function as a component upon reconstitution or as an additional agent prior to spray-drying or freeze-drying.

In alternative embodiments, pharmaceutical compositions provided herein comprise lyophilized, cryodesiccated, freeze-dried or dehydrated microflora material from a formulation comprising one or more, two or more, three or more, four or more additives selected from the group consisting of trehalose, mannitol, sucrose, NaCl, and polysorbate 80, wherein the two or more components are effective in reducing or minimizing microbial viability loss in the microflora material. Used herein, additives include, but are not limited to, cryoprotectants, surfactants, and emulsifiers.

In alternative embodiments, additives used herein comprising trehalose, mannitol, sucrose, NaCl, polysorbate 80, or combinations thereof at concentrations effective for long term storage of lyophilized, cryodesiccated, freeze-dried or dehydrated microflora material at ambient temperature, room temperature, approximately room temperature. In some embodiments, additives used herein comprise between 2% and 4%, between 4% and 6%, between 6% and 8%, between 8% and 10%, between 10% and 12%, between 12% and 14%, between 14% and 16%, between 16% and 18%, between 18% and 20%, between 2% and 20%, between 4% and 18%, between 6% and 16%, or between 8% and 14% trehalose, sucrose, mannitol or combinations thereof. In some embodiments, additives used herein comprise between 0.001% and 0.05%, between 0.003 and 0.04%, between 0.005% and 0.03%, between 0.007% and 0.02%, about 0.005%, about 0.01%, about 0.02%, about 0.03%, about 0.04%, or about 0.05% polysorbate 80.

In alternative embodiments, additives used herein maintain at least 50%, at least 55%, at least 60%, at least 65%, at least 70%, at least 75%, at least 80%, at least 85%, at least 90%, or at least 95% microbial viability of lyophilized, cryodesiccated, freeze-dried or dehydrated microflora material disclosed herein after about 2, about 4, about 8, about 12, about 20, about 30, about 40, about 50, or about 60 weeks of storage from preparation at ambient temperature, room temperature, approximately room temperature, or at between about 15° C. to 26° C., or at about 20° C., 21° C., 22° C., 23° C., 24° C., 25° C., 26° C., 27° C. or 28° C.

In alternative embodiments, additives used herein maintain about 50%, about 55%, about 60%, about 65%, about 70%, about 75%, about 80%, about 85%, about 90%, or about 95% microbial viability of lyophilized, cryodesiccated, freeze-dried or dehydrated microflora material disclosed herein after about 2, about 4, about 8, about 12, about 20, about 30, about 40, about 50, or about 60 weeks of storage from preparation at ambient temperature, room temperature, approximately room temperature, or at between about 15° C. to 26° C., or at about 20° C., 21° C., 22° C., 23° C., 24° C., 25° C., 26° C., 27° C. or 28° C.

In alternative embodiments, additives used herein maintain about 50%, about 55%, about 60%, about 65%, about 70%, about 75%, about 80%, about 85%, about 90%, or about 95% microbial viability of lyophilized, cryodesiccated, freeze-dried or dehydrated microflora material disclosed herein after about 2, about 4, about 8, about 12, about 20, about 30, about 40, about 50, or about 60 weeks of storage from preparation at ambient temperature, room temperature, approximately room temperature, or at between about 15° C. to 26° C., or at about 20° C., 21° C., 22° C., 23° C., 24° C., 25° C., 26° C., 27° C. or 28° C.

In alternative embodiments, pharmaceutical compositions provided herein maintain at least about $10^8$ viable cells cells/g, $10^9$ viable cells cells/g, $10^{10}$ viable cells cells/g, $10^{12}$ viable cells cells/g, $10^{13}$ viable cells cells/g, or $10^{14}$ viable cells cells/g, or between about $10^7$ and $10^{12}$ viable cells cells/g, or between about $10^9$ and $10^{11}$ viable cells cells/g after about 2, about 4, about 8, about 12, about 20, about 30, about 40, about 50, or about 60 weeks of storage from preparation at ambient temperature, room temperature, approximately room temperature, or at between about 15° C. to 26° C., or at about 20° C., 21° C., 22° C., 23° C., 24° C., 25° C., 26° C., 27° C. or 28° C.

In alternative embodiments, stabilizers that help reduce destruction of living bacteria include skim milk, erythritol, arabitol, sorbitol, glucose, fructose and other polyols. Polymers such as dextran and polyethylene glycol can also be used to stabilize the fecal bacterial cells.

In alternative embodiments, an entire (or substantially entire) microbiota, or an isolated and/or treated (e.g., purified or isolated) fecal material and/or flora, is lyophilized or freeze dried, and the product is stored at ambient temperatures (e.g., room temperature). In alternative embodiments freeze-drying allows the majority of cells to remain viable, and produces a powdered form of the product that can be gently pulverized into a powder. The powder, or lyophilized or freeze-dried flora or isolate, then can be encapsulated into a carrier, e.g., a tablet, geltab, pill or capsule, e.g., an enteric-coated capsule, or placed into oil-filled capsules for ingestion. Alternatively, the freeze-dried or lyophilized product, or powder, can be reconstituted at ambient temperatures before delivery to an individual in e.g., a fluid, e.g., a sterile fluid, such as saline, a buffer or a media such as a fluid-glucose-cellobiose agar (RGCA) media.

In alternative embodiments an entire (or substantially entire) microbiota, or an isolated and/or treated (e.g., purified or isolated) fecal material and/or flora also can be spray-dried.

In alternative embodiments, the entire (or substantially entire) microbiota, or isolated and/or treated fecal material and/or flora, is supplemented with wild type bacteria which has been derived from normal animal (e.g., human) flora and/or recombinantly treated bacteria, e.g., recombinant microorganisms that can synthesize a protein, small molecule or carbohydrate that has a self-protective or ameliorative effect; or recombinant microorganisms that can self-destruct when provided with an appropriate signal, e.g., a chemical delivered by ingestion.

In some embodiments, pharmaceutical compositions provided herein include at least 4 different phyla of gut, colon or intestinal bacteria extracted or prepared from the gut, colon or intestine, and a cryoprotectant, wherein the phyla include a Bacteroidetes, a *Firmicutes*, a Proteobacteria a Tenericutes phylum, or a combination thereof, wherein optionally the phyla are chosen from Bacteroidetes, *Firmicutes*, Proteobacteria, Tenericutes, or a combination thereof, wherein the compositions, upon reconstitution with water, include no greater than about 0.05%, 0.1%, 0.2%, 0.3%, 0.4%, 0.5%, 0.6%, 0.7%, 0.8%, 0.9% 1%, 2%, 3%, 4%, 5%, 6%, 7%, 8%, 9%, or 10% weight non-living material/weight biological material, wherein the biological material includes human gut, colon or intestinal fecal microbes, and optionally the biological material includes human gut, colon or intestinal bacteria, and wherein optionally the compositions include a pharmaceutically acceptable carrier, and optionally the composition is a formulation for oral administration.

In some embodiments, pharmaceutical compositions provided herein include an extract of human feces and a cryoprotectant, wherein the composition, upon reconstitution with water, is substantially odorless, wherein the composition includes biological material, and optionally wherein the biological material includes microbes, and wherein optionally the composition includes a pharmaceutically acceptable carrier, and optionally the composition is a formulation for oral administration.

In alternative embodiments, the microflora material of a pharmaceutical composition provided herein comprises predominantly spores. In some embodiments, at least 50%, 60%, 70%, 80%, 90%, 95%, 97%, 99% of the microbes in the microflora material are in a spore form. "Spore" refers to a microbial entity, which is in a dormant, non-vegetative and non-reproductive stage. Spores are generally resistant to environmental stress including, but not limited to radiation, desiccation, enzymatic treatment, temperature variation, nutrient deprivation, and chemical disinfectants. A collection of spores may be purified from a fecal sample, e.g. via ethanol or heat treatment or other known methods in the art. Alternatively, a collection of spores may be derived through culture methods starting from isolated spore former species or from a mixture of such species, either in vegetative or spore form.

In some embodiments, pharmaceutical compositions provided herein comprise non-pathogenic *Clostridia* spores. In other embodiments, pharmaceutical compositions also comprises viable non-pathogenic *Collinsella*. In some embodiments, pharmaceutical compositions further comprise viable non-pathogenic organisms from at least one of the groups consisting of *Bacteroides, Fusobacteria, Propionibacteria, Lactobacilli, anaerobic cocci, Ruminococcus, E. coli, Gemmiger, Desulfomonas, Peptostreptococcus*, and *Bifidobacteria*. In further embodiments, pharmaceutical compositions further comprises one or more viable non-pathogenic microorganisms selected from the group consisting of a *Bacteroides fragilis* ss. *Vulgatus, Collinsella aerofaciens, Bacteroides fragilis* ss. *Thetaiotaomicron, Peptostreptococcus productus* II, *Parabacteroides distasonis Fusobacterium prausnitzii, Coprococcus eutactus, Collinsella aerofaciens* III, *Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ss. A, *Eubacterium biforme, Bifidobacterium infantis, Eubac-* terium rectale III-F, *Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ss. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Bacteroides fragilis ss. ovatus*, -ss. d, -ss. f; *Bacteroides* L-1, L-5; *Fusobacterium nucleatum, Fusobacterium mortiferum, Escherichia coli, Gemella morbillorum, Finegoldia magnus, Peptococcus* G, -AU-2; *Streptococcus intermedius, Ruminococcus lactaris, Ruminococcus* CO *Gemmiger* X, *Coprococcus* BH, -CC; *Eubacterium tenue, Eubacterium ramulus, Bacteroides clostridiiformis* ss. *clostridliformis, Bacteroides coagulans, Prevotella oralis, Prevotella ruminicola, Odoribacter splanchnicus, Desuifomonas pigra, Lactobacillus* G, *Succinivibrio* A, and a combination thereof.

In some embodiments, pharmaceutical compositions provided herein comprise non-pathogenic *Clostridia* spores and viable non-pathogenic *Collinsella* without organisms from at least one of the groups consisting of *Bacteroides, Fusobacteria, Propionibacteria, Lactobacilli*, anaerobic cocci, *Ruminococcus, E. coli, Gemmiger, Desulfomonas, Peptostreptococcus*, and *Bifidobacteria*. In other embodiments, pharmaceutical compositions comprise no viable non-pathogenic microorganisms selected from the group consisting of a *Bacteroides fragilis* ss. *Vulgatus, Collinsella aerofaciens, Bacteroides fragilis* ss. *Thetaiotaomicron, Peptostreptococcus productus* II, *Parabacteroides distasonis Fusobacterium prausnitzii, Coprococcus eutactus, Collinsella aerofaciens* III, *Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ss. A, *Eubacterium biforme, Bifidobacterium infantis, Eubacterium rectale* III-F, *Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ss. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Bacteroides fragilis ss. ovatus*, -ss. d, -ss. f; *Bacteroides* L-1, L-5; *Fusobacterium nucleatum, Fusobacterium mortiferum, Escherichia coli, Gemella morbillorum, Finegoldia magnus, Peptococcus* G, -AU-2; *Streptococcus intermedius, Ruminococcus lactaris, Ruminococcus* CO *Gemmiger* X, *Coprococcus* BH, -CC; *Eubacterium tenue, Eubacterium ramulus, Bacteroides clostridiiformis* ss. *clostridhformis, Bacteroides coagulans, Prevotella oralis, Prevotella ruminicola, Odoribacter splanchnicus, Desuifomonas pigra, Lactobacillus* G, *Succinivibrio* A, and a combination thereof.

In alternative embodiments, the transplantation product (e.g., a composition provided herein) is delivered by an infusion, e.g., through the rectum, stoma or down the upper gastrointestinal (GI) tract, or it can be used in a suppository pill, tablet or encapsulated form, e.g., with an enteric-coated graded release capsule or a tablet, e.g., with the addition of excipients. In alternative embodiments the transplantation product is administered as a suppository to give the highest concentration in the rectum.

In one embodiment, the transplantation product (e.g., a composition provided herein, e.g., comprising an isolated or purified fecal flora or an entire (or substantially entire) microbiota) is stored at room temperature before or during delivery to an individual, e.g., in a fluid, e.g., a sterile fluid, such as saline, a buffer or a media such as a fluid-glucose-cellobiose agar (RGCA) media.

In alternative embodiments, the compositions provided herein are used to ameliorate, stabilize, prevent and/or treat: various gastrointestinal conditions, e.g., *C. difficile* infection, *C. perfringens welchii* and other *Clostridium* infections, irritable bowel syndrome, constipation, pouchitis, Crohn's disease and microscopic colitis; neurological conditions such as autism, Parkinson's disease, myoclonus dystonia, autism, amyotrophic lateral sclerosis and multiple sclerosis, Grand mal seizures or petit mal seizures. In one embodiment, the neurological conditions are treated by encapsulated or frozen material. In alternative embodiments, for colitis patients, recurrent administration is required to suppress and reverse the inflammatory bowel disease and irritable bowel syndrome.

In alternative embodiments, a crude collected stool is filtered and/or homogenized, and then its bacterial cells are separated (e.g., from the "crud" which contains the fiber) by plasmapheresis, centrifugation, celltrifuge, column chromatography (e.g., affinity chromatography), immunoprecipitation (e.g., antibodies fixed to a solid surface, such as beads or a plate). Centrifugation, including use of a "celltrifuge" (e.g., a Baxter model MEDIFUGE1215™) are processes that involve centrifugal force to separate mixtures. For "celltrifugation", the densest components will then fly to the outside of the spinning plates while the rest of the components will migrate to the axis. The effect of the gravitational force will be increased by spinning the flattened product between rapidly moving glass plates. The centrifuge or celltrifuge can be set up such that the stool will be diluted adequately and set on a spinning cycle and collection of cells will occur only peripherally on the centrifuge.

In alternative embodiments, wild type bacterial cells (including e.g., an entire (or substantially entire) microbiota) separated or purified e.g., by centrifugation, celltrifugation, plasmapheresis and the like. In alternative embodiments, this material is stored at room temperature in a container, e.g., a bag, which can then be used to infuse through a colonoscope, naso-duodenal or nasogastric tube. In alternative embodiments, it can be delivered to a facility (e.g., a hospital pharmacy) to be kept at room temperature, e.g., at between about 20° C. to 26° C. In alternative embodiments compositions provided herein are used either in a solution, gels, geltabs, pills, capsules or tablets, or suppositories, e.g., to be reconstituted later as an enema or infuse set through a colonoscope.

In alternative embodiments, solutions, gels, geltabs, pills, capsules or tablets comprising compositions provided herein (e.g., isolated or purified fecal flora or an entire (or substantially entire) microbiota) can be taken long term, e.g., on a daily basis long term, e.g., for one, two, three or four weeks or months or more, to treat, stabilize, ameliorate or prevent a chronic and/or an immune condition such as e.g., autism, persistent infection, rheumatoid arthritis, systemic lupus erythematosus, autoimmune renal diseases, e.g., nephritis, severe obstruction, inflammatory bowel disease (IBD), irritable bowel syndrome (IBS), and other conditions set forth herein.

The following section contains a further list of exemplary embodiments.

Embodiment 1

A pharmaceutical composition comprising a fecal microbiota preparation in a lyophilized formulation, wherein after at least 12 weeks of storage at ambient temperature or lower the fecal microbiota preparation is capable of maintaining at least 60% cell viability relative to the initial cell viability at the start of the storage.

Embodiment 2

The pharmaceutical composition of Embodiment 1, wherein after at least 12 weeks of storage at ambient temperature or lower the fecal microbiota preparation is capable of maintaining about 60% to about 80% cell viability relative to the initial cell viability at the start of the storage.

Embodiment 3

The pharmaceutical composition of Embodiment 1 or 2, wherein the lyophilized fecal microbiota preparation comprises a non-selective and substantially complete fecal microbiota preparation from a single donor.

Embodiment 4

The pharmaceutical composition of Embodiment 3, wherein the weight ratio between fecal-derived non-living material and fecal-derived biological material in the fecal microbiota preparation is no greater than 10%.

Embodiment 5

The pharmaceutical composition of any one of Embodiments 1 to 4, wherein the lyophilized formulation comprises one or more cryoprotectants selected from the group consisting of dimethyl sulfoxide (DMSO), glycerol, polyethylene glycol (PEG), alanine, glycine, proline, mannitol, sucrose, glucose, lactose, ribose, trehalose, hydroxypropyl-β-cyclodextrin (HPβCD), and any combination thereof.

Embodiment 6

The pharmaceutical composition of any one of Embodiments 1 to 4, wherein the lyophilized formulation comprises trehalose.

Embodiment 7

The pharmaceutical composition of Embodiment 6, wherein the lyophilized formulation comprises 2% to 15% trehalose.

Embodiment 8

The pharmaceutical composition of Embodiment 6, wherein the lyophilized formulation comprises about 5% trehalose.

Embodiment 9

The pharmaceutical composition of any one of Embodiments 1 to 8, wherein the lyophilized formulation comprises trehalose and sucrose.

Embodiment 10

The pharmaceutical composition of Embodiment 1 or 2, wherein the lyophilized formulation comprises between about 8% to 12% trehalose with between about 1.5% to 3.5% sucrose and between about 0.5% to 1.5% NaCl.

Embodiment 11

The pharmaceutical composition of any one of Embodiments 1 to 10, wherein the pharmaceutical composition is for oral administration.

Embodiment 12

The pharmaceutical composition of any one of Embodiments 1 to 10, wherein the pharmaceutical composition is formulated as a geltab, pill, microcapsule, capsule, or tablet.

Embodiment 13

The pharmaceutical composition of any one of Embodiments 1 to 12, wherein every 200 mg of the pharmaceutical composition comprises a pharmacologically active dose of microbes or spores selected from the group consisting of $10^3$ to $10^{14}$, $10^4$ to $10^{14}$, $10^5$ to $10^{14}$, $10^6$ to $10^{14}$, $10^7$ to $10^{14}$, $10^8$ to $10^{14}$, $10^4$ to $10^3$, $10^5$ to $10^{12}$, $10^6$ to $10^{11}$, $10^7$ to $10^{10}$, $10^8$ to $10^9$, $10^3$ to $10^{13}$, $10^3$ to $10^{12}$, $10^3$ to $10^{11}$, $10^3$ to $10^{10}$, $10^3$ to $10^9$, $10^3$ to $10^8$, $10^3$ to $10^7$, $10^3$ to $10^6$, $10^3$ to $10^5$ and $10^3$ to $10^4$ cfu or total cell count.

Embodiment 14

The pharmaceutical composition of any one of Embodiments 1 to 13, wherein the preparation of the fecal microbiota preparation involves a treatment selected from the group consisting of ethanol treatment, detergent treatment, heat treatment, irradiation, and sonication, or a combination thereof.

Embodiment 15

The pharmaceutical composition of any one of Embodiments 1 to 13, wherein the preparation of the fecal microbiota preparation involves a separation step selected from the group consisting of filtering, sieving, density gradients, filtration, chromatography, and a combination thereof.

Embodiment 16

The pharmaceutical composition of any one of Embodiments 1 to 15, wherein the fecal microbiota preparation has at least about 20%, 30%, 40%, 50%, 60%, 70%, 80%, 85%, 90%, 95%, 99%, or 99.5% microbes in a spore form.

Embodiment 17

The pharmaceutical composition of any one of Embodiments 1 to 16, wherein the pharmaceutical composition is effective for treating one or more disorders selected from the group consisting of recurrent or primary *C. diff.* infection, autism spectrum disorder (ASD), ulcerative colitis, Crohn's disease, and irritable bowel syndrome.

Embodiment 18

The pharmaceutical composition of any one of Embodiments 1 to 16, wherein the pharmaceutical composition is effective for treating one or more disorders or conditions selected from the group consisting of Acne, AIDS Enteropathy, AIDS-related Gastroenteritis, Alopecia Totalis, Alzheimers Disease, Amyloidosis, Amyotrophic Lateral Sclerosis, Ankylosing Spondylitis, Anorexia, Antibiotic Associated Colitis, Asbergers Syndrome, Attention Deficit Disorder (ADD), Attention Deficit Hyperactivity Disorder (ADHD), Autism Spectrum Disorder (ASD), Behcet's Syndrome, Chronic *Clostridium difficile* Infection (CDI), Chronic constipation, Chronic Depression, Chronic Fatigue Syndrome (CFS), Chronic Idiopathic Pseudo Obstructive Syndrome, Chronic Inflammation Demyelinating Polyneuropathy, Chronic Nausea, Chronic Urticaria, Coeliac Disease, Collagenous Colitis, Colonic Polyps, Constipation Predominant FBD, Crohn's Disease, Cryptogenic Cirrhosis, Cyclic Vomiting, Dermatitis Herpetiformis, Diabetes, Familial Mediterranean Fever, Fatty Liver, Functional Bowel Disease (FBD), Gastro-oesophageal Reflux, Gillian-Barre Syndrome, Glomerulonephritis, Haemolytic Uraemic Syndrome, Halitosis, IBS constipation-predominant, IBS diarrhea/constipation alternating, IBS diarrhea-predominant, IBS pain-predominant, Idiopathic Thrombocytopenic Purpura (ITP), Idiopathic/Simple Constipation, Indeterminate Colitis, Inflammatory Bowel Disease (IBD), Irritable bowel syndrome (IBS), Juvenile Diabetes Mellitus, Lyme Disease, Manic Depressive Illness, Metabolic Syndrome, Microscopic Colitis, Migraine, Mixed Cryoglobulinaemia, Mucous Colitis, Multiple Sclerosis, Myasthenia Gravis, NASH (Nonalcoholic Steatohepatitis), Non-Rheumatoid Arthritis, Non-Rheumatoid Factor Positive Arthritis, Non-ulcer Dyspepsia, Norwalk Viral Gastroenteritis, Obesity, Obsessive Compulsive Disorder, Pain Predominant FBD, Parkinson's Disease, Polyarteritis, Polyposis Coli, Primary Biliary Cirrhosis, Primary *Clostridium difficile* Infection (CDI), Primary Sclerosing Cholangitis (PSC), Pseudomembranous Colitis, Psychotic Disorders, Reiter's Syndrome, Relapsing Diverticulitis, Rett Syndrome, Rheumatoid Arthritis, Rosacea, Rotavirus Gastroenteritis, Sacroiliitis, Schizophrenia, Scleroderma, Sjogren's Syndome, Small Bowel Bacterial Overgrowth, Sudden Infant Death Syndrome (SIDS), Systemic Lupus Erythematosus, Ulcerative Colitis, Upper Abdominal FBD, Vasculitic Disorders, Viral Gastroenteritis, pre-diabetic syndrome, type I diabetes, type II diabetes, depression, schizophrenia, and a mood disorder.

Embodiment 19

The pharmaceutical composition of any one of Embodiments 1 to 16, wherein the pharmaceutical composition is effective for treating one or more disorders selected from the group consisting of recurrent *C. diff.* infection, autism spectrum disorder (ASD), constipation predominant functional bowel disease (FBD), pain predominant FBD, upper abdominal FBD, non-ulcer dyspepsia (NUD), gastro-oesophageal reflux, indeterminate colitis, microscopic colitis, pseudomembranous colitis, viral gastroenteritis, Norwalk viral gastroenteritis, rotavirus gastroenteritis, AIDS related gastroenteritis, non rheumatoid factor positive arthritis, Lyme disease, systemic lupus, idiopathic thrombocytopenic purpura, Sjogren's syndrome, haemolytic uremic syndrome or scleroderma, Gillain-Barre syndrome, Chronic Inflammatory Demyelinating Polyneuropathy, chronic depression, schizophrenia, psychotic disorders, manic depressive illness, Asbergers syndrome, Rett syndrome, attention deficit hyperactivity disorder (ADHD), and attention deficit disorder (ADD), sudden infant death syndrome (SIDS), anorexia nervosa.

Embodiment 20

An oral pharmaceutical composition comprising a non-selective fecal microbiota preparation in a lyophilized formulation, wherein, after at least 12 weeks of storage at ambient temperature or lower, the fecal microbiota preparation is capable of maintaining about 60% to about 80% cell viability relative to the initial cell viability at the start of the storage, and is effective for treating one or more disorders or conditions selected from the group consisting of Acne, AIDS Enteropathy, AIDS-related Gastroenteritis, Alopecia Totalis, Alzheimers Disease, Amyloidosis, Amyotrophic Lateral Sclerosis, Ankylosing Spondylitis, Anorexia, Antibiotic Associated Colitis, Asbergers Syndrome, Attention Deficit Disorder (ADD), Attention Deficit Hyperactivity Disorder (ADHD), Autism Spectrum Disorder (ASD), Behcet's Syndrome, Chronic *Clostridium difficile* Infection (CDI), Chronic constipation, Chronic Depression, Chronic Fatigue Syndrome (CFS), Chronic Idiopathic Pseudo Obstructive Syndrome, Chronic Inflammation Demyelinating Polyneuropathy, Chronic Nausea, Chronic Urticaria, Coeliac Disease, Collagenous Colitis, Colonic Polyps, Constipation Predominant FBD, Crohn's Disease, Cryptogenic Cirrhosis, Cyclic Vomiting, Dermatitis Herpetiformis, Diabetes, Familial Mediterranean Fever, Fatty Liver, Functional Bowel Disease (FBD), Gastro-oesophageal Reflux, Gillian-Barre Syndrome, Glomerulonephritis, Haemolytic Uraemic Syndrome, Halitosis, IBS constipation-predominant, IBS diarrhea/constipation alternating, IBS diarrhea-predominant, IBS pain-predominant, Idiopathic Thrombocytopenic Purpura (ITP), Idiopathic/Simple Constipation, Indeterminate Colitis, Inflammatory Bowel Disease (IBD), Irritable bowel syndrome (IBS), Juvenile Diabetes Mellitus, Lyme Disease, Manic Depressive Illness, Metabolic Syndrome, Microscopic Colitis, Migraine, Mixed Cryoglobulinaemia, Mucous Colitis, Multiple Sclerosis, Myasthenia Gravis, NASH (Nonalcoholic Steatohepatitis), Non-Rheumatoid Arthritis, Non-Rheumatoid Factor Positive Arthritis, Non-ulcer Dyspepsia, Norwalk Viral Gastroenteritis, Obesity, Obsessive Compulsive Disorder, Pain Predominant FBD, Parkinson's Disease, Polyarteritis, Polyposis Coli, Primary Biliary Cirrhosis, Primary *Clostridium difficile* Infection (CDI), Primary Sclerosing Cholangitis (PSC), Pseudomembranous Colitis, Psychotic Disorders, Reiter's Syndrome, Relapsing Diverticulitis, Rett Syndrome, Rheumatoid Arthritis, Rosacea, Rotavirus Gastroenteritis, Sacroiliitis, Schizophrenia, Scleroderma, Sjogren's Syndome, Small Bowel Bacterial Overgrowth, Sudden Infant Death Syndrome (SIDS), Systemic Lupus Erythematosus, Ulcerative Colitis, Upper Abdominal FBD, Vasculitic Disorders, Viral Gastroenteritis, pre-diabetic syndrome, type I diabetes, type II diabetes, depression, schizophrenia, and a mood disorder.

Embodiment 21

The oral pharmaceutical composition of Embodiment 20, wherein the pharmaceutical composition is effective for treating one or more disorders selected from the group consisting of recurrent or primary C. diff. infection, autism spectrum disorder (ASD), ulcerative colitis, Crohn's disease, and irritable bowel syndrome.

The invention will be further described with reference to the following examples; however, it is to be understood that the invention is not limited to such examples.

EXAMPLES

Example 1

Exemplary Methods

One exemplary procedure comprises lyophilizing preparations consisted of homogenized stool, and storing at room temperature (RT), or ambient temperature. This study was designed to determine the viability of microorganisms in frozen and lyophilized fecal microbiota preparations stored for 12 weeks at room temperature (RT), or ambient temperature.

Methods: Frozen fecal microbiota preparations from the FOCUS clinical trial (NCT01896635) consisted of stool homogenized 1:3 (w/w) in saline and glycerol. Lyophilized preparations consisted of stool homogenized 1:4 (w/w) in a mixture of saline, trehalose and sucrose, and then freeze-dried to achieve a final water activity (aw) of <0.3. Frozen preparations were stored at −80° C.

Lyophilized preparations were stored at ambient temperature, as well as at 4° C. and −80° C. Microbial viability and total counts were determined at preparation, and after 4 and 12 weeks storage. Assessments were undertaken on triplicate samples at each timepoint, using fluorescence microscopy or flow cytometry and BacLight™ Live/Dead and Counting kits.

Results: Fecal microbiota preparations stored frozen had an average microbial viability of 64.1±5.0% (standard error of the mean (SEM)) at preparation, decreasing to 54.2±3.9% and 57.7±1.2% after 4 and 12 weeks storage. Thus, after 12 weeks storage 90% viability was maintained, and the viable count was $9.5 \times 10^9$ cells/mL. Preparations used for lyophilization had an average viability of 45.6±2.2% prior to lyophilization, decreasing to 42.6±4.1% immediately after freeze drying. At −80° C., viability declined to 31.7±7.8% and 37.5±5.5% after 4 and 12 weeks storage. Thus, after 12 weeks of storage at −80° C., 82% viability was maintained, and the viable count was $1.5 \times 10^{11}$ cells/g lyophilized powder. After 12 weeks storage at ambient and 4° C., 70% and 81% viabilities were maintained and viable counts were $1.4 \times 10^{11}$ and $1.6 \times 10^{11}$ cells/g, respectively.

Conclusions: Both frozen and lyophilized fecal microbiota preparations experienced losses in viability over 12 weeks, but these losses were not more than 20% compared with initial viability, except for lyophilized preparations stored at ambient temperature. Irrespective of storage temperature however, large numbers of viable cells, approximately $10^{11}$ cells/g, were present in lyophilized preparations at the end of the storage period. This storage trial demonstrates strong potential for lyophilization as a process to improve the availability of fecal microbiota material.

Provided herein are lyophilized preparations that do not require refrigeration, and method for producing them. These lyophilized preparations can be incorporated into capsules for oral administration.

Example 2

Exemplary Methods

This example describes exemplary methods for making, storing and using composition provided herein. A summary of the phases of a exemplary freeze-drying process is provided in Table A.

Pre-Preparation Summary

Once stool has been homogenized, aliquot 35 mL into 50 mL centrifuge tubes. Centrifuge at low speed (1000 RPM) 100.62×g for 5 minutes, remove supernatant and place into a sterile container or bag. Discard the pellet. Aliquot 35 mL of the supernatant into 50 mL centrifuge tubes as per previous step and centrifuge the tubes at (6145 RPM) 3800×g for 20 minutes at 4° C. Once the run is finished, remove most of the supernatant (or as much as possible before the pellet is disturbed) and re-suspend the pellet using a vortex. Fresh saline can be used if not enough liquid is left in the tube.

Measure the remaining slurry and using a syringe, collect the slurry and pour into a freeze dryer tray.

Protocol:

Stage 1—Material/Freeze Dryer Set-Up

1. Turn Freeze Dryer on in Manual Mode with cooling ON and vacuum valve OFF. Set shelf temperature to −80° C. Note: the dryer should be started up the day before freeze drying is to commence. Shelves can take up to 5 hours to achieve extra low temperatures.
2. Ensure the condenser and shelves are at temperature, Load the shelves with full trays. No more than 150 mL volume in each tray.
3. Pre-freeze material for 2 h at −55° C.

Note: See stage 2, step 1 at this point.

Stage 2—Freeze Dryer Start-Up & Primary Drying

1. Turn the pump on with valve closed at least 30 minutes before the run is due to commence to allow the pump to warm up. Record time on in pump log book.
2. Once the pump has been running for at least 30 minutes and the shelf temperature is at
   −55° C., open the pump valve and set the 'pressure' setting on the freeze dryer (manual mode) to ON.
3. Once the pressure stabilizes to 0.13 hPa, change the shelf temperature to −20° C. in 10° increments every 10 minutes (i.e. over 35 minutes).

Stage 3—Secondary Drying

1. Perform the pressure decay test after 15, 20, 25 hours. Once the pressure decay test is 'positive' or pressure stabilizes in the chamber when the pump is cut off, the sample has finished primary drying.
   Hold at −20° C. for approximately 24 hours (this time is a variable that can be determined by the pressure rise test results. When the pressure rise test indicates that drying has stopped add 50% more time.
2. Ramp the shelf temperature from −20° C. to +30° C. at 10° C. per 10 min (i.e. over 50 mins). Hold at 30° C. for 4 hours.
3. After 4 h, lower the shelf temperature to 5° C. and hold for 15 minutes. Raise the pressure to ambient (stage 4, step 1). See FIG. 1.

Stage 4—Unloading & Temporary Storage
1. Isolate the pump by closing the valve and open the release valve on the freeze dryer.
2. Once the freeze dryer release valve is opened, the condenser will appear to fill with vapor and the samples need to be taken out immediately. Lift the rack out of the dryer and place each tray in a blue air tight container with a 5 gram (g) silica gel pouch and close the lid.
3. Place freeze dryer in 'stop' mode and store the shelves out of the chamber so the ice sheet can melt and drain.
4. Allow pump to run for a further 45 minutes after the drying is finished to remove impurities and switch off. Record time off in pump log book.

TABLE A

A summary of the phases of a exemplary freeze-drying process.

| Phase | Pressure (hPa) | Time (hh:mm) | Chamber Temp (° C.) | Shelf Temp (° C.) |
|---|---|---|---|---|
| Freezing (to cool | Ambient | — | −98 | −80 |
| Pre-Freeze | Ambient | 02:00 | −98 | −55 |
| 1° Drying | 0.13 | 36:00 | −98 | −20 |
| 2° Drying | 0.13-Ambient | 05:05 | −98 | 30 |

Viability and count results for frozen and freeze-dried FMT samples are summarized in Table 1 (FIG. 3) for samples formulated with;
1. 10% trehalose with 2.5% sucrose and 0.9% NaCl (3 replicates)
2. 10% trehalose with 2.5% sucrose, 0.9% NaCl and 0.01% polysorbate 80 (3 replicates)
3. 5% trehalose with 0.9% NaCl and 0.01% polysorbate 80 (5 replicates)
4. 10% mannitol with 0.9% NaCl and 0.01% polysorbate 80 (6 replicates)
5. 5% mannitol with 0.9% NaCl and 0.01% polysorbate 80 (3 replicates)
6. 5% trehalose and 5% mannitol with 0.9% NaCl and 0.01% polysorbate 80 (2 replicates).

Viability after Freeze-Drying

To date, the average % losses in viability (absolute and proportional) are least for: 10% trehalose with 2.5% sucrose and 0.9% NaCl
<10% mannitol with 0.9% NaCl and 0.01% polysorbate 80
<10% trehalose with 2.5% sucrose, 0.9% NaCl and 0.01% polysorbate 80
~5% mannitol with 0.9% NaCl and 0.01% polysorbate 80
<5% trehalose with 0.9% NaCl and 0.01% polysorbate 80
<5% trehalose and 5% mannitol with 0.9% NaCl and 0.01% polysorbate 80.
Average counts (live cells/g) are ~$1 \times 10^{11}$ for all formulations.

Water Activity

Water activity results for all freeze-dried samples are summarized in Table 2 (FIG. 4). On average, water activity results are best (lowest) for:
10% trehalose with 2.5% sucrose, 0.9% NaCl and 0.01% polysorbate 80
<10% trehalose with 2.5% sucrose and 0.9% NaCl
10% mannitol with 0.9% NaCl and 0.01% polysorbate 80
<5% trehalose and 5% mannitol with 0.9% NaCl and 0.01% polysorbate 80
<5% trehalose with 0.9% NaCl and 0.01% polysorbate 80
<5% mannitol with 0.9% NaCl and 0.01% polysorbate 80.

4 Week Stored Samples

Viability losses after 4 weeks storage of freeze-dried FMT at ambient, 4° C. and −80° C. are summarized in Table 3 (FIG. 5 and FIG. 6).

Based on available data to date, as expected viability maintenance was improved at lower storage temperatures with viability losses minimised at −80° C. compared with 4° C. or ambient temperature storage, irrespective of the cryoprotectant used.

To date, the average % losses in viability (absolute and proportional) with storage for 4 weeks at −80° C. are least for:
10% trehalose with 2.5% sucrose, 0.9% NaCl and 0.01% polysorbate 80
<10% trehalose with 2.5% sucrose and 0.9% NaCl
<5% mannitol with 0.9% NaCl and 0.01% polysorbate 80
~(about) 10% mannitol with 0.9% NaCl and 0.01% polysorbate 80
<5% trehalose with 0.9% NaCl and 0.01% polysorbate 80
5% trehalose and 5% mannitol with 0.9% NaCl and 0.01% polysorbate 80.

12 Week Stored Samples

Viability losses after 12 weeks storage of freeze-dried FMT at ambient, 4° C. and −80° C. are summarized in Table 4 (FIG. 7 and FIG. 8). Note that 12 week viability results for a number of samples are pending.

Based on available data to date, it is clear that viability maintenance continues to be best at lower storage temperatures, irrespective of the cryoprotectant used.

To date, the average % losses in viability (absolute and proportional) with storage for 12 weeks at −80° C. are least for:
10% trehalose with 2.5% sucrose, 0.9% NaCl and 0.01% polysorbate 80
<5% mannitol with 0.9% NaCl and 0.01% polysorbate 80
<10% mannitol with 0.9% NaCl and 0.01% polysorbate 80.

Conclusions

Overall proportional losses for the six formulations tested are summarized in FIG. 2. Considering losses both after freeze-drying, and after storage under the specified conditions, the exemplary formulations based on 10% trehalose with 2.5% sucrose, 0.9% NaCl+/−0.01% polysorbate 80, provided the best results.

Example 3

Exemplary Clinical Methods

The exemplary freeze-dried FMT product described above based on (comprising) trehalose, sucrose, NaCl and polysorbate 80 cryoprotective agents, was prepared in a delay-release capsule to open in the small intestine of patients. The capsules were stored at ambient temperature, i.e., room temperature, or about 21° C. to 22° C. Four capsules each containing approx. $10^{10}$ viable donor gut microbiome bacteria were used for patient ingestion.

Three patients with microbiologically-proven chronic relapsing *Clostridium difficile* infection who had failed standard therapy with metronidazole and vancomycin, were given two capsules in the morning followed by two capsules at night. Having presented with recurrent diarrhea 6 to 25 times per day and at times at night, malaise, nausea and one patient with vomiting, were given the capsules as described.

Within 2-3 days of ingestion and on no other therapy, each of the three patients reported rapid reduction in the frequency of diarrhea. By day 7 all had 3-5 formed or semi-formed stools, greater control of urgency, minimal then absent nausea, allowing better food ingestion. They regained their original weight loss of between 6 and 17 kg over the next 3-4 months. Numerous improvements in symptoms took place, and the result paralleled the type of results obtained with transcolonoscopic infusion of FMT material in the past.

In conclusion, these results demonstrate that the oral treatment with the lyophilized full spectrum microbiota was clinically successful. At stool retesting 6 weeks later there was no evidence of cultured *C. difficile* and it's toxin was absent from stool.

A number of embodiments of the invention have been described. Nevertheless, it will be understood that various modifications may be made without departing from the spirit and scope of the invention. Accordingly, other embodiments are within the scope of the following claims.

What is claimed is:

1. A pharmaceutical composition comprising a microbial preparation in a lyophilized formulation comprising one or more cryoprotectants selected from the group consisting of trehalose, mannitol, sucrose, and any combination thereof,
    wherein said microbial preparation comprises viable purified microorganisms from two or more genera selected from the group consisting of *Akkermansia, Anaerotruncus, Blautia, Clostridium*, and *Dorea*,
    wherein after at least 4 weeks of storage at room temperature, said microbial preparation is capable of maintaining at least 50% cell viability relative to the initial cell viability immediately prior to storage.

2. The pharmaceutical composition of claim 1, wherein said microbial preparation comprises viable purified microorganisms from three or more genera selected from the group consisting of *Akkermansia, Anaerotruncus, Blautia, Clostridium*, and *Dorea*.

3. The pharmaceutical composition of claim 1, wherein said microbial preparation comprises viable purified microorganisms from *Anaerotruncus, Blautia, Clostridium*, and *Dorea*.

4. The pharmaceutical composition of claim 3, wherein said microbial preparation further comprises viable purified microorganisms from two or more genera selected from the group consisting of *Eubacterium, Ruminococcus*, and *Subdoligranulum*.

5. The pharmaceutical composition of claim 1, wherein said microbial preparation comprises viable purified *Clostridium* selected from the group consisting of *Clostridium innocuum* and *Clostridium symbiosum*.

6. The pharmaceutical composition of claim 1, wherein said microbial preparation comprises viable purified *Dorea longicatena*.

7. The pharmaceutical composition of claim 1, wherein said microbial preparation comprises viable purified *Blautia producta*.

8. The pharmaceutical composition of claim 1, wherein said microbial preparation comprises viable purified microorganisms from *Blautia producta, Clostridium innocuum, Clostridium symbiosum*, and *Dorea longicatena*.

9. The pharmaceutical composition of claim 8, wherein said microbial preparation further comprises viable purified microorganisms from two or more genera selected from the group consisting of *Eubacterium, Ruminococcus*, and *Subdoligranulum*.

10. The pharmaceutical composition of claim 1, wherein said microbial preparation further comprises viable purified microorganisms from one or more genera selected from the group consisting of *Eubacterium, Ruminococcus*, and *Subdoligranulum*.

11. The pharmaceutical composition of claim 10, wherein said microbial preparation comprises viable purified *Eubacterium*.

12. The pharmaceutical composition of claim 10, wherein said microbial preparation comprises viable purified *Ruminococcus torques*.

13. The pharmaceutical composition of claim 1, wherein said microbial preparation further comprises viable purified microorganisms from two or more genera selected from the group consisting of *Eubacterium, Ruminococcus*, and *Subdoligranulum*.

14. The pharmaceutical composition of claim 1, wherein said one or more cryoprotectants are also lyoprotectants.

15. The pharmaceutical composition of claim 1, wherein said lyophilized formulation comprises trehalose.

16. The pharmaceutical composition of claim 15, wherein said lyophilized formulation comprises 6% to 10% trehalose.

17. The pharmaceutical composition of claim 15, wherein said lyophilized formulation comprises at least 5% trehalose.

18. The pharmaceutical composition of claim 1, wherein said lyophilized formulation comprises trehalose and sucrose.

19. The pharmaceutical composition of claim 1, wherein said pharmaceutical composition is for oral administration.

20. The pharmaceutical composition of claim 1, wherein said pharmaceutical composition is formulated as a geltab, pill, microcapsule, capsule, or tablet.

21. The pharmaceutical composition of claim 1, wherein every 200 mg of said pharmaceutical composition comprises a pharmacologically active dose of microbes or spores of $10^5$ to $10^{12}$ colony forming units (CFU) or total cell count.

22. The pharmaceutical composition of claim 1, wherein every 200 mg of said pharmaceutical composition comprises a pharmacologically active dose of microbes or spores of $10^6$ to $10^{11}$ colony forming units (CFU) or total cell count.

23. The pharmaceutical composition of claim 1, wherein said pharmaceutical composition is effective for treating recurrent or primary *C. difficile* infection.

24. The pharmaceutical composition of claim 1, wherein said pharmaceutical composition further comprises an amino acid.

25. The pharmaceutical composition of claim 24, wherein said amino acid is histidine.

26. The pharmaceutical composition of claim 1, wherein said one or more cryoprotectants comprise sucrose.

27. The pharmaceutical composition of claim 1, wherein said one or more cryoprotectants are at least 10% trehalose.

28. The pharmaceutical composition of claim 1, wherein said one or more cryoprotectants are at least 2.5% sucrose.

29. The pharmaceutical composition of claim 1, wherein said one or more cryoprotectants are trehalose and mannitol.

30. The pharmaceutical composition of claim 1, wherein said one or more cryoprotectants are at least 5% mannitol.

31. The pharmaceutical composition of claim 1, wherein said one or more cryoprotectants are at least 10% mannitol.

32. The pharmaceutical composition of claim 1, wherein said viable purified microorganisms comprise spore-forming bacteria.

33. The pharmaceutical composition of claim 32, wherein said spore-forming bacteria are one or more *Clostridium* species.

34. The pharmaceutical composition of claim 1, wherein the viable purified microorganisms are cultured.

35. A capsule comprising a pharmaceutical composition comprising a microbial preparation in a lyophilized formulation comprising one or more cryoprotectants selected from the group consisting of trehalose, mannitol, sucrose, and any combination thereof,
wherein said microbial preparation comprises viable purified microorganisms from two or more genera selected from the group consisting of *Akkermansia, Anaerotruncus, Blautia, Clostridium*, and *Dorea*,
wherein after at least 4 weeks of storage at room temperature, said microbial preparation is capable of maintaining at least 50% cell viability relative to the initial cell viability immediately prior to storage.

36. The pharmaceutical composition of claim 35, wherein said viable purified microorganisms comprise spore-forming bacteria.

37. The pharmaceutical composition of claim 35, wherein said viable purified microorganisms comprise spore-forming bacteria of at least two or more of said genera.

38. The pharmaceutical composition of claim 35, wherein said one or more cryoprotectants are trehalose and mannitol.

39. The pharmaceutical composition of claim 35, wherein said one or more cryoprotectants are trehalose and sucrose.

40. The pharmaceutical composition of claim 35, wherein said one or more cryoprotectants are at least 5% trehalose.

41. The pharmaceutical composition of claim 35, wherein the viable purified microorganisms are cultured.

* * * * *